United States Patent
Bjore et al.

(10) Patent No.: US 7,354,917 B2
(45) Date of Patent: Apr. 8, 2008

(54) OXABISPIDINE COMPOUNDS AND THEIR USE IN THE TREATMENT OF CARDIAC ARRHYTHMIAS

(75) Inventors: Annika Bjore, Molndal (SE); Ulrik Gran, Molndal (SE); Gert Strandlund, Molndal (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 11/570,439

(22) PCT Filed: Jun. 13, 2005

(86) PCT No.: PCT/SE2005/000890

§ 371 (c)(1), (2), (4) Date: Dec. 12, 2006

(87) PCT Pub. No.: WO2005/123747

PCT Pub. Date: Dec. 29, 2005

(65) Prior Publication Data

US 2007/0259864 A1 Nov. 8, 2007

(30) Foreign Application Priority Data

Jun. 15, 2004 (SE) .................................. 0401540

(51) Int. Cl.
*C07D 498/08* (2006.01)
*A61K 31/5386* (2006.01)

(52) U.S. Cl. .................................. 514/230.5; 544/105

(58) Field of Classification Search ................ 544/105; 514/230.5

See application file for complete search history.

(56) References Cited

U.S. PATENT DOCUMENTS

| 3,962,449 | A | 6/1976 | Binnig et al. |
| 4,459,301 | A | 7/1984 | Binnig et al. |
| 4,550,112 | A | 10/1985 | Schoen et al. |
| 4,556,662 | A | 12/1985 | Binnig et al. |
| 5,468,858 | A | 11/1995 | Berlin et al. |
| 7,217,708 | B2 * | 5/2007 | Barnwell et al. ......... 514/230.5 |

FOREIGN PATENT DOCUMENTS

| EP | 0306871 A2 | 3/1989 |
| EP | 0308843 A2 | 3/1989 |
| EP | 0655228 A1 | 5/1995 |
| WO | 91/07405 A1 | 5/1991 |
| WO | 99/31100 A1 | 6/1999 |
| WO | 01/28992 A2 | 4/2001 |
| WO | 02/28863 A1 | 4/2002 |
| WO | 02/28864 A1 | 4/2002 |
| WO | 02/83690 A1 | 4/2002 |
| WO | 02/83691 AW | 4/2002 |

OTHER PUBLICATIONS

Preliminary Report: Effect of Encainide and Flecainide on Mortality in a Randomized Trial of Arrhythmia Suppression After Myocardial Infarction, New England Journal of Medicine, Aug. 10, 1989, pp. 406-412, vol. 321, No. 6.
Bogousslavsky, Julien et al., Pure midbrain infarction: Clinical syndromes, MRI, and etiologic patterns, Neurology, 1994, pp. 2032-2040, vol. 44.
Yoshidome, Toshifumi et al., Infrared Spectroscopic Analyses of Transformations of Chemical Species on the Silica Highly-Reacted with Gaseous BF3, Analytical Sciences, Mar. 2003, pp. 429-435, vol. 19.
Paroczai, M. and Karpati, E., Investigations to Characterize A New antiarrthymic Drug Bisaramil, Pharamcological Research, 1991, pp. 149-162, vol. 24; No. 2.
Garrison, Gregory L. et al., Novel 3,7-Diheterabicyclo [3.3.1]nonanes That Possess Predominant Class III Antiarrhythmic Activity in 1-4 Day Post Infarction Dog Models: X-ray Diffraction Analysis of 3-[4-(1h-Imidazol-1-yl) benzoyl]-7-isopropyl-3,7-diazabicyclo[3.3.1]nonane Dihydroperchlorate, Journal of Medicinal Chemistry, 1986, pp. 2559-2570, vol. 39, No. 13.
Weinges, Klaus et al., [Uber den mechanismus der saurekatalysierten Kondensations-reaktionen der Hydroxy-flavane und Hydroxy-flavanole-(3)], Chem. Ber., 1963, pp. 2870-2878, vol. 96.

* cited by examiner

*Primary Examiner*—Kahsay T. Habte
(74) *Attorney, Agent, or Firm*—Pepper Hamilton LLP

(57) ABSTRACT

There is provided compounds of formula I, wherein $R^1$, $R^2$, $R^4$, $R^{41}$ to $R^{46}$, A, B and G have meanings given in the description, which are useful in the prophylaxis and in the treatment of arrhythmias, in particular a trial and ventricular arrhythmias.

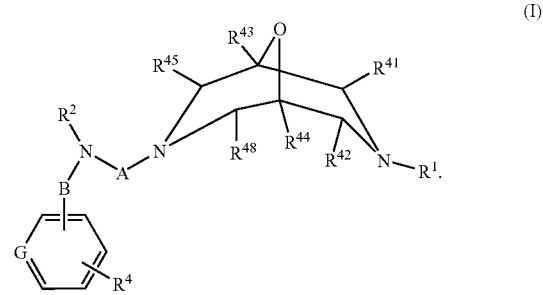

(I)

34 Claims, No Drawings

OXABISPIDINE COMPOUNDS AND THEIR USE IN THE TREATMENT OF CARDIAC ARRHYTHMIAS

CROSS-REFERENCE TO RELATED APPLICATIONS

This application is the U.S. National Stage filing of International Application Ser. No. PCT/SE05/00890 filed Jun. 13, 2005, which claims priority to Swedish Applaction Ser. No. 0401540-0 filed Jun. 15, 2004, each of which is incorporated herein by reference in its entirety.

FIELD OF THE INVENTION

This invention relates to novel pharmaceutically useful compounds, in particular compounds which are useful in the treatment of cardiac arrhythmias.

BACKGROUND AND PRIOR ART

Cardiac arrhythmias may be defined as abnormalities in the rate, regularity, or site of origin of the cardiac impulse or as disturbances in conduction which causes an abnormal sequence of activation. Arrhythmias may be classified clinically by means of the presumed site of origin (i.e. as supraventricular, including atrial and atrioventricular, arrhythmias and ventricular arrhythmias) and/or by means of rate (i.e. bradyarrhythmias (slow) and tachyarrhythmias (fast)).

In the treatment of cardiac arrhythmias, the negative outcome in clinical trials (see, for example, the outcome of the Cardiac Arrhythmia Suppression Trial (CAST) reported in *New England Journal of Medicine,* 321, 406 (1989)) with "traditional" antiarrhythmic drugs, which act primarily by slowing the conduction velocity (class I antiarrhythmic drugs), has prompted drug development towards compounds which selectively delay cardiac repolarization, thus prolonging the QT interval. Class III antiarrhythmic drugs may be defined as drugs which prolong the trans-membrane action potential duration (which can be caused by a block of outward $K^+$ currents or from an increase of inward ion currents) and refractoriness, without affecting cardiac conduction.

One of the key disadvantages of hitherto known drugs which act by delaying repolarization (class III or otherwise) is that they all are known to exhibit a unique form of proarrhythmia known as torsades de pointes (turning of points), which may, on occasion be fatal. From the point of view of safety, the minimisation of this phenomenon (which has also been shown to be exhibited as a result of administration of non-cardiac drugs such as phenothiazines, tricyclic antidepressants, antihistamines and antibiotics) is a key problem to be solved in the provision of effective antiarrhythmic drugs.

Antiarrhythmic drugs based on bispidines (3,7-diazabicyclo[3.3.1]nonanes), are known from inter alia international patent applications WO 91/07405 and WO 99/31100, European patent applications 306 871, 308 843 and 655 228 and U.S. Pat. Nos. 3,962,449, 4,556,662, 4,550,112, 4,459,301 and 5,468,858, as well as journal articles including, inter alia, *J. Med. Chem.* 39, 2559, (1996), *Pharmacol. Res.,* 24, 149 (1991), *Circulation,* 90, 2032 (1994) and *Anal. Sci.* 9, 429, (1993).

Certain oxabispidine compounds are disclosed as chemical curiosities in *Chem. Ber.,* 96, 2872 (1963). The use of certain other oxabispidine compounds in the treatment of cardiac arrhythmias is disclosed in WO 01/28992. Methods for the preparation of such oxabispidine compounds are disclosed in WO 02/28863, WO 02/28864, WO 02/83690 and WO 02/83691. Oxabispidine compounds of formula I, as defined below, are neither disclosed nor suggested by any of these documents.

We have surprisingly found that a novel group of oxabispidine-based compounds exhibit electrophysiological activity, and are therefore expected to be useful in the treatment of cardiac arrhythmias. The novel group of oxabispidine-based compounds has advantageous properties compared to compounds of the prior art, such as enhanced potency, enhanced selectivity, and/or reduction of total clearance. These advantageous properties can distinguish the use of such compounds as pharmaceutical agents by lowering the daily clinical dose, lengthening the duration of action, and/or improving the side effect profile.

DISCLOSURE OF THE INVENTION

According to the invention there is provided compounds of formula I,

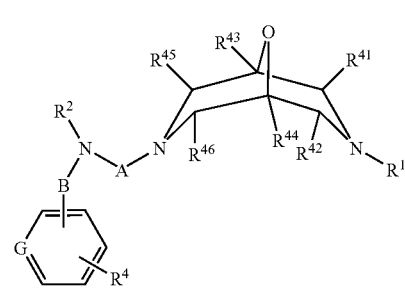

wherein $R^1$ represents $C_{1-12}$ alkyl (which alkyl group is optionally substituted by one or more groups selected from halo, cyano, nitro, aryl, Het$^1$, —C(O)R$^{5a}$, —OR$^{5b}$, —N(R$^6$)R$^{5c}$, —C(O)XR$^7$, —C(O)N(R$^{8a}$)R$^{5d}$, —OC(O)N(R$^{8b}$)R$^{5e}$, —S(O)$_2$R$^{9a}$, —S(O)$_2$N(R$^{9b}$)R$^{9c}$ and —N(R$^{9b}$)S(O)$_2$R$^{9d}$) or $R^1$ represents —C(O)XR$^7$, —C(O)N(R$^{8a}$)R$^{5d}$ or —S(O)$_2$R$^{9a}$;

$R^{5a}$ to $R^{5e}$ independently represent, at each occurrence when used herein, H, $C_{1-6}$ alkyl (which latter group is optionally substituted by one or more substituents selected from —OH, halo, cyano, nitro, aryl, aryloxy, Het$^2$, —S(O)$_2$N(R$^{9b}$)R$^{9c}$ and —N(R$^{9b}$)S(O)$_2$R$^{9d}$), aryl or Het$^3$, or R$^{5d}$ or R$^{5e}$, together with, respectively, R$^{8a}$ or R$^{8b}$, may represent $C_{3-6}$ alkylene (which alkylene group is optionally interrupted by an O atom and/or is optionally substituted by one or more $C_{1-3}$ alkyl groups);

$R^6$ represents H, $C_{1-6}$ alkyl (optionally substituted by one or more substituents selected from —OH, halo, cyano, nitro, aryl, —S(O)$_2$N(R$^{9b}$)R$^{9c}$ and —N(R$^{9b}$)S(O)$_2$R$^{9d}$), aryl, —C(O)R$^{10a}$, —C(O)OR$^{10b}$, —C(O)N(R$^{10c}$)R$^{10d}$ or —S(O)$_2$R$^{10e}$;

$R^{10a}$ to $R^{10e}$ independently represent $C_{1-6}$ alkyl (optionally substituted by one or more substituents selected from —OH, halo, cyano, nitro and aryl), aryl, or R$^{10a}$, R$^{10c}$ or R$^{10d}$ represents H;

$R^7$ represents, at each occurrence when used herein, $C_{1-12}$ alkyl (optionally substituted by one or more substituents selected from —OH, halo, cyano, nitro, aryl, $C_{1-6}$ alkoxy, Het$^4$, —S(O)$_2$N(R$^{9b}$)R$^{9c}$ and —N(R$^{9b}$)S(O)$_2$R$^{9d}$);

$R^{8a}$ and $R^{8b}$ independently represent H, $C_{1-12}$ alkyl, $C_{1-6}$ alkoxy (which latter two groups are optionally substituted by one or more substituents selected from —OH, halo, cyano, nitro, $C_{1-4}$ alkyl, $C_{1-4}$ alkoxy, —S(O)$_2$N(R$^{9b}$)R$^{9c}$ and —N(R$^{9b}$)S(O)$_2$R$^{9d}$), -D-aryl, -D-aryloxy, -D-Het$^5$, -D-N(H) C(O)R$^{11a}$, -D-S(O)$_2$R$^{12a}$, -D-C(O)R$^{11b}$, -D-C(O)OR$^{12b}$, -D-C(O)N(R$^{11c}$)R$^{11d}$, or $R^{8a}$ or $R^{8b}$, together with, respectively, $R^{5d}$ or $R^{5e}$, may represent $C_{3-6}$ alkylene (which alkylene group is optionally interrupted by an O atom and/or is optionally substituted by one or more $C_{1-3}$ alkyl groups);

$R^{11a}$ to $R^{11d}$ independently represent H, $C_{1-6}$ alkyl (optionally substituted by one or more substituents selected from —OH, halo, cyano, nitro and aryl), aryl, or $R^{11c}$ and $R^{11d}$ together represent $C_{3-6}$ alkylene;

$R^{12a}$ and $R^{12b}$ independently represent $C_{1-6}$ alkyl (optionally substituted by one or more substituents selected from —OH, halo, cyano, nitro and aryl) or aryl;

D represents, at each occurrence when used herein, a direct bond or $C_{1-6}$ alkylene;

X represents O or S;

$R^{9a}$ represents, at each occurrence when used herein, $C_{1-6}$ alkyl (optionally substituted by one or more substituents selected from —OH, halo, cyano, nitro, aryl, —S(O)$^2$N(R$^{9b}$) R$^{9c}$ and —N(R$^{9b}$)S(O)$_2$R$^{9d}$) or aryl;

$R^{9b}$ represents, at each occurrence when used herein, H or $C_{1-6}$ alkyl;

$R^{9c}$ and $R^{9d}$ independently represent, at each occurrence when used herein, $C_{1-6}$ alkyl (optionally substituted by one or more substituents selected from —OH, halo, cyano, nitro, aryl and Het$^6$), aryl or Het$^7$, or $R^{9c}$ represents H;

$R^2$ represents S(O)R$^{3a}$, —C(O)OR$^{3b}$, —C(O)R$^{3c}$, —C(O) N(R$^{3d}$)(R$^{3e}$) or —S(O)$_2$N(R$^{3f}$)(R$^{3g}$);

$R^{3a}$ to $R^{3g}$ independently represent $C_{1-6}$ alkyl (optionally substituted by one or more substituents selected from halo, -E-aryl, -E-Het$^8$, —C(O)R$^{16a}$, —C(O)OR$^{16b}$ and —C(O)N (R$^{16c}$)R$^{16d}$), aryl or Het$^9$, or $R^{3c}$ and $R^{3d}$ to $R^{3g}$ independently represent H;

$R^{16a}$ to $R^{16d}$ independently represent, at each occurrence when used herein, H, $C_{1-6}$ alkyl (optionally substituted by one or more substituents selected from halo, aryl and Het$^{10}$), aryl, Het$^{11}$, or $R^{16c}$ and $R^{16d}$ together represent $C_{3-6}$ alkylene, optionally interrupted by an O atom;

E represents, at each occurrence when used herein, a direct bond or $C_{1-4}$ alkylene;

Het$^1$ to Het$^{11}$ independently represent five- to twelve-membered heterocyclic groups containing one or more heteroatoms selected from oxygen, nitrogen and/or sulfur, which groups are optionally substituted by one or more substituents selected from —OH, oxo, halo, cyano, nitro, $C_{1-6}$ alkyl, $C_{1-6}$ alkoxy, aryl, aryloxy, —N(R$^{17a}$)R$^{17b}$, —C(O) R$^{17c}$, —C(O)OR$^{17d}$, —C(O)N(R$^{17e}$)R$^{17f}$, —N(R$^{17g}$)C(O) R$^{17h}$, —S(O)$_2$N(R$^{17i}$)R$^{17j}$ and —N(R$^{17k}$)S(O)$_2$R$^{17l}$;

$R^{17a}$ to $R^{17l}$ independently represent $C_{1-6}$ alkyl, aryl or $R^{17a}$ to $R^{17k}$ independently represent H;

A represents $C_{2-6}$ alkylene optionally interrupted by —S(O)$_2$N(R$^{18a}$)— or —N(R$^{18b}$)S(O)$_2$— and/or optionally substituted by one or more substituents selected from —OH, halo and amino;

B represents -Z$^1$-{[C(O)]$_a$C(H)(R$^{19a}$)}$_b$—, -Z$^2$-[C(O)]$_c$N (1$^{19b}$)—, -Z$^2$-S(O)$_n$—, -Z$^2$-N(R$^{18c}$)S(O)$_2$—, -Z$^2$-S(O)$_2$N (R$^{18d}$)— or -Z$^2$-O— (in which six groups Z$^1$ or Z$^2$ is attached to the nitrogen atom bearing R$^2$);

$Z^1$ represents a direct bond or $C_{1-4}$ alkylene, optionally interrupted by —N(R$^{18e}$)S(O)$_2$— or —S(O)$_2$N(R$^{18f}$)—;

$Z^2$ represents, at each occurrence when used herein, $C_{2-4}$ alkylene, optionally interrupted by —N(R$^{18g}$)S(O)$_2$— or —S(O)$_2$N(R$^{18h}$)—;

a, b and c independently represent 0 or 1;

n represents 0, 1 or 2;

$R^{18a}$ to $R^{18h}$ independently represent H or $C_{1-6}$ alkyl;

$R^{19a}$ represents H or, together with a single $R^4$ substituent at a position on the phenyl or pyridyl group that is ortho- to the position at which the group B is attached, $R^{19a}$ represents $C_{2-4}$ alkylene optionally interrupted or terminated by O, S or N(R$^{20}$);

$R^{19b}$ represents H, $C_{1-6}$ alkyl or, together with a single $R^4$ substituent at a position on the phenyl or pyridyl group that is ortho- to the position at which the group B is attached, $R^{19b}$ represents $C_{2-4}$ alkylene;

$R^{20}$ represents H or $C_{1-6}$ alkyl;

G represents CH or N;

$R^4$ represents one or more optional substituents selected from —OH, cyano, halo, nitro, $C_{1-6}$ alkyl (optionally terminated by —N(H)C(O)OR$^{21a}$), $C_{1-6}$ alkoxy, —N(R$^{22a}$)R$^{22b}$, —C(O)R$^{22c}$, —C(O)OR$^{22d}$, —C(O)N(R$^{22e}$)R$^{22f}$, —N(R$^{22g}$) C(O)R$^{22h}$, —N(R$^{22i}$)C(O)N(R$^{22j}$)R$^{22k}$, —N(R$^{22m}$)S(O)$_2$ R$^{21b}$, —S(O)$_2$N(R$^{22n}$)R$^{22o}$, —S(O)$_2$R$^{21c}$, —OS(O)$_2$R$^{21d}$ and aryl, and an $R^4$ substituent in a position on the phenyl or pyridyl group that is ortho- to the position at which the group B is attached may (i) together with $R^{19a}$, represent $C_{2-4}$ alkylene optionally interrupted or terminated by O, S or N(R$^{20c}$), or (ii) together with $R^{19b}$, represent $C_{2-4}$ alkylene;

$R^{21a}$ to $R^{21d}$ independently represent $C_{1-6}$ alkyl;

$R^{22a}$ and $R^{22b}$ independently represent H, $C_{1-6}$ alkyl or together represent $C_{3-6}$ alkylene, resulting in a four- to seven-membered nitrogen-containing ring;

$R^{22c}$ to $R^{22o}$ independently represent H or $C_{1-6}$ alkyl; and $R^{41}$ to $R^{46}$ independently represent H or $C_{1-3}$ alkyl;

wherein each aryl and aryloxy group, unless otherwise specified, is optionally substituted;

or a pharmaceutically acceptable derivative thereof;

which compounds are referred to hereinafter as "the compounds of the invention".

For the avoidance of doubt it is to be understood that where in this specification a group is qualified by 'hereinbefore defined', 'defined hereinbefore' or 'defined above' the said group encompasses the first occurring and broadest definition as well as each and all of the other definitions for that group.

Unless otherwise specified, alkyl groups and alkoxy groups as defined herein may be straight-chain or, when there is a sufficient number (i.e. a minimum of three) of carbon atoms be branched-chain, and/or cyclic. Further, when there is a sufficient number (i.e. a minimum of four) of carbon atoms, such alkyl and alkoxy groups may also be part cyclic/acyclic. Such alkyl and alkoxy groups may also be saturated or, when there is a sufficient number (i.e. a minimum of two) of carbon atoms, be unsaturated and/or interrupted by one or more oxygen and/or sulfur atoms. Unless otherwise specified, alkyl and alkoxy groups may also be substituted by one or more halo, and especially fluoro, atoms.

Unless otherwise specified, alkylene groups as defined herein may be straight-chain or, when there is a sufficient number (i.e. a minimum of two) of carbon atoms, be branched-chain. Such alkylene chains may also be saturated or, when there is a sufficient number (i.e. a minimum of two) of carbon atoms, be unsaturated and/or interrupted by one or more oxygen and/or sulfur atoms. Unless otherwise specified, alkylene groups may also be substituted by one or more halo atoms.

The term "aryl", when used herein, includes $C_{6-10}$ aryl groups such as phenyl, naphthyl and the like. The term "aryloxy", when used herein includes $C_{6-10}$ aryloxy groups such as phenoxy, naphthoxy and the like. For the avoidance of doubt, aryloxy groups referred to herein are attached to the rest of the molecule via the O-atom of the oxy-group. Unless otherwise specified, aryl and aryloxy groups may be substituted by one or more substituents including —OH, halo, cyano, nitro, $C_{1-6}$ alkyl, $C_{1-6}$ alkoxy, $N(R^{22a})R^{22b}$, —$C(O)R^{22c}$, —$C(O)OR^{22d}$, —$C(O)N(R^{22e})R^{22f}$, —$(R^{22g})C(O)R^{22h}$, —$N(R^{22m})S(O)_2R^{21b}$, —$S(O)_2N(R^{22n})R^{22o}$, —$S(O)_2R^{21c}$, and/or —$OS(O)_2R^{21d}$ (wherein $R^{21b}$ to $R^{21d}$ and $R^{22a}$ to $R^{22o}$ are as hereinbefore defined). When substituted, aryl and aryloxy groups are preferably substituted by between one and three substituents.

The term "halo", when used herein, includes fluoro, chloro, bromo and iodo.

Het ($Het^1$, $Het^2$, $Het^3$, $Het^4$, $Het^5$, $Het^6$, $Het^7$, $Het^8$, $Het^9$, $Het^{10}$ and $Het^{11}$) groups that may be mentioned include those containing 1 to 4 heteroatoms (selected from the group oxygen, nitrogen and/or sulfur) and in which the total number of atoms in the ring system are between five and twelve. Het ($Het^1$, $Het^2$, $Het^3$, $Het^4$, $Het^5$, $Het^6$, $Het^7$, $Het^8$, $Het^9$, $Het^{10}$ and $Het^{11}$) groups may be fully saturated, wholly aromatic, partly aromatic and/or bicyclic in character. Heterocyclic groups that may be mentioned include 1-azabicyclo[2.2.2]octanyl, benzimidazolyl, benzisoxazolyl, benzodioxanyl, benzodioxepanyl, benzodioxolyl, benzofuranyl, benzofurazanyl, benzo-morpholinyl, 2,1,3-benzoxadiazolyl, benzoxazinonyl, benzoxazolidinyl, benzoxazolyl, benzopyrazolyl, benzo[e]pyrimidine, 2,1,3-benzothiadiazolyl, benzothiazolyl, benzothienyl, benzotriazolyl, chromanyl, chromenyl, cinnolinyl, 2,3-dihydrobenzimidazolyl, 2,3-dihydrobenzo[b]furanyl, 1,3-dihydrobenzo[c]furanyl, 2,3-dihydropyrrolo[2,3-b]pyridinyl, dioxanyl, furanyl, hexahydropyrimidinyl, hydantoinyl, imidazolyl, imidazo[1,2-a]pyridinyl, imidazo[2,3-b]thiazolyl, indolyl, isoquinolinyl, isoxazolyl, maleimido, morpholinyl, oxadiazolyl, 1,3-oxazinanyl, oxazolyl, phthalazinyl, piperazinyl, piperidinyl, purinyl, pyranyl, pyrazinyl, pyrazolyl, pyridinyl, pyrimidinyl, pyrrolidinonyl, pyrrolidinyl, pyrrolinyl, pyrrolo[2,3-b]pyridinyl, pyrrolo[5,1-b]pyridinyl, pyrrolo[2,3-c]pyridinyl, pyrrolyl, quinazolinyl, quinolinyl, sulfolanyl, 3-sulfolenyl, 4,5,6,7-tetrahydrobenzimidazolyl, 4,5,6,7-tetrahydrobenzopyrazolyl, 5,6,7,8-tetrahydrobenzo[e]-pyrimidine, tetrahydrofuranyl, tetrahydropyranyl, 3,4,5,6-tetrahydro-pyridinyl, 1,2,3,4-tetrahydropyrimidinyl, 3,4,5,6-tetrahydropyrimidinyl, thiadiazolyl, thiazolidinyl, thiazolyl, thienyl, thieno[5,1-c]pyridinyl, thiochromanyl, triazolyl, 1,3,4-triazolo[2,3-b]pyrimidinyl and the like.

Values of $Het^1$ that may be mentioned include 2,3-dihydrobenzo[b]furanyl, furanyl, imidazolyl, isoxazolyl, pyridinyl and thiazolyl.

Substituents on Het ($Het^1$, $Het^2$, $Het^3$, $Het^4$, $Het^5$, $Het^6$, $Het^7$, $Het^8$, $Het^9$, $Het^{10}$ and $Het^{11}$) groups may, where appropriate, be located on any atom in the ring system including a heteroatom. The point of attachment of Het ($Het^1$, $Het^2$, $Het^3$, $Het^4$, $Het^5$, $Het^6$, $Het^7$, $Het^8$, $Het^9$, $Het^{10}$ and $Het^{11}$) groups may be via any atom in the ring system including (where appropriate) a heteroatom, or an atom on any fused carbocyclic ring that may be present as part of the ring system. Het ($Het^1$, $Het^2$, $Het^3$, $Het^4$, $Het^5$, $Het^6$, $Het^7$, $Het^8$, $Het^9$, $Het^{10}$ and $Het^{11}$) groups may also be in the N— or S-oxidised form.

Pharmaceutically acceptable derivatives include salts and solvates. Salts which may be mentioned include acid addition salts. Pharmaceutically acceptable derivatives also include, at the oxabispidine or (when G represents N) pyridyl nitrogens, $C_{1-4}$ alkyl quaternary ammonium salts and N-oxides, provided that when a N-oxide is present:

(a) no Het ($Het^1$, $Het^2$, $Het^3$, $Het^4$, $Het^5$, $Het^6$, $Het^7$, $Het^8$, $Het^9$, $Het^{10}$ and $Het^{11}$) group contains an unoxidised S-atom; and/or (b) n does not represent 0 when B represents $-Z^2-S(O)_n-$.

The compounds of the invention may exhibit tautomerism. All tautomeric forms and mixtures thereof are included within the scope of the invention.

The compounds of the invention may also contain one or more asymmetric carbon atoms and may therefore exhibit optical and/or diastereoisomerism.

Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation, or by derivatisation, for example with a homochiral acid followed by separation of the diastereomeric esters by conventional means (e.g. HPLC, chromatography over silica). All stereoisomers are included within the scope of the invention.

Abbreviations are listed at the end of this specification.

Preferred values of each variable group are as follows. Such values may be used where appropriate with any of the values, definitions, claims, aspects or embodiments defined hereinbefore or hereinafter. In particular, each may be used as an individual limitation on the broadest definition of formula (I).

Particular values of each variable group are as follows. Such values may be used where appropriate with any of the values, definitions, claims, aspects or embodiments defined hereinbefore or hereinafter. In particular, each may be used as an individual limitation on the broadest definition of formula (I). $R^1$ represents $C_{1-4}$ alkyl, which alkyl group is substituted by at least one—phenyl or phenoxy group (both optionally substituted by one or more halo, cyano, methyl, methoxy, fluromethoxy, difluoromethoxy or trifluromethoxy groups);

A represents a direct bond or $C_{1-3}$ alkylene (such as a $C_2$ alkylene);

B represents a direct bond, $C_{1-3}$ alkylene (such as a $C_2$ alkylene), or $C_{1-3}$ alkoxy (such as a $C_2$ alkoxy, in which the oxygen is attached to the phenyl group that is optionally substituted with $R^4$);

$R^2$ represents $—S(O)_2R^{3a}$, $—C(O)OR^{3b}$, $—C(O)R^{3c}$ or $—C(O)N(R^{3d})R^{3e}$;

$R^{3a}$ to $R^{3b}$ each independently represent hydrogen or $C_{1-3}$ alkyl (such as methyl, ethyl, isopropyl or propyl);

G represents carbon;

$R^{41}$ to $R^{46}$ represents hydrogen; and $R^4$ represents one or more optional substituents selected from cyano and/or halo (such as fluoro) and an $R^4$ substituent is in a position on the phenyl group that is ortho- and/or para- to the position at which the group B is attached.

Preferred compounds of the invention include those in which:

$R^1$ represents $C_{1-8}$ alkyl (which alkyl group is optionally substituted by one or more groups selected from halo, aryl (which latter group is optionally substituted by one or more substituents selected from —OH, halo, cyano, nitro, $C_{1-5}$ alkyl, $C_{1-4}$ alkoxy (which latter two groups are optionally substituted by one or more halo atoms), —$C(O)R^{22c}$ and —S(O)$_2$R$^{21c}$), Het$^1$, —C(O)R$^{5a}$, —OR$^{5b}$, —N(R$^6$)R$^{5c}$, —C(O)N(R$^{8a}$)R$^{5d}$, —OC(O)N(R$^{8b}$)R$^{5e}$, —S(O)$_2$R$^{9a}$, —S(O)$_2$N(H)R$^{9c}$ and —N(H)S(O)$_2$R$^{9d}$) or R$^1$ represents —C(O)OR$^7$, —C(O)N(R$^{8a}$)R$^{5d}$ or —S(O)$_2$R$^{9a}$;

R$^{5a}$ to R$^{5e}$ independently represent, at each occurrence when used herein, H, C$_{1-6}$ alkyl (which latter group is optionally substituted by one or more substituents selected from cyano, nitro, optionally substituted aryl and optionally substituted aryloxy), aryl (which latter group is optionally substituted by one or more substituents selected from —OH, halo, cyano, nitro, N(R$^{22a}$)R$^{22b}$ (in which latter group R$^{22a}$ and R$^{22b}$ together represent C$_{3-6}$ alkylene), C$_{1-5}$ alkyl and C$_{1-5}$ alkoxy (which latter two groups are optionally substituted by one or more halo atoms)), Het$^3$, or R$^{5d}$, together with R$^{8a}$, represents C$_{4-5}$ alkylene (which alkylene group is optionally interrupted by an O atom);

R$^6$ represents H, C$_{1-6}$ alkyl, optionally substituted aryl —C(O)R$^{10a}$, —C(O)OR$^{10b}$, —C(O)N(R$^{10c}$)R$^{10d}$ or —S(O)$_2$R$^{10e}$;

R$^{10a}$, R$^{10b}$ and R$^{10e}$ independently represent C$_{1-5}$ alkyl (optionally substituted by one or more substituents selected from halo and optionally substituted aryl) or optionally substituted aryl;

R$^{10c}$ and R$^{10d}$ independently represent H or C$_{1-4}$ alkyl;

R$^7$ represents C$_{1-6}$ alkyl (optionally substituted by one or more substituents selected from halo, optionally substituted aryl, C$_{1-4}$ alkoxy and Het$^4$);

R$^{8a}$ and R$^{8b}$ independently represent H, C$_{1-6}$ alkyl (which latter group is optionally substituted by one or more substituents selected from halo, cyano and nitro), -D-(optionally substituted aryl), -D-(optionally substituted aryloxy), -D-Het, -D-N(H)C(O)R$^{11a}$, -D-C(O)R$^{11b}$, or R$^{8a}$, together with R$^{5d}$ represents C$_{4-5}$ alkylene (which alkylene group is optionally interrupted by an O atom);

R$^{11a}$ and R$^{11d}$ independently represent C$_{1-4}$ alkyl (optionally substituted by one or more substituents selected from halo, cyano, nitro and optionally substituted aryl) or optionally substituted aryl;

D represents, at each occurrence when used herein, a direct bond or C$_{1-4}$ alkylene;

R$^{9a}$ represents, C$_{1-6}$ alkyl (optionally substituted by one or more halo groups) or optionally substituted aryl;

R$^{9c}$ and R$^{9d}$ independently represent, at each occurrence when used herein, C$_{1-5}$ alkyl (optionally substituted by one or more substituents selected from halo, optionally substituted aryl and Het$^6$), optionally substituted aryl or Het$^7$, or R$^{9c}$ represents H;

R$^2$ represents —S(O)$_2$R$^{3a}$, —C(O)OR$^{3b}$, —C(O)R$^{3c}$ or —C(O)N(R$^{3d}$)R$^{3e}$;

R$^{3a}$ to R$^{3e}$ independently represent C$_{1-5}$ alkyl (optionally substituted by one or more substituents selected from halo, optionally substituted aryl and Het$^8$), optionally substituted aryl or Het$^9$, or R$^{3d}$ represents H;

Het$^1$ and Het$^3$ to Het$^9$ independently represent four- to ten-membered heterocyclic groups containing one to four heteroatoms selected from oxygen, nitrogen and/or sulfur, which groups are optionally substituted by one or more substituents selected from —OH, oxo, halo, cyano, C$_{1-4}$ alkyl, C$_{1-4}$ alkoxy, phenyl, —N(H)R$^{17a}$, —C(O)R$^{17c}$, —N(H)C(O)R$^{17h}$ and —N(H)S(O)$_2$R$^{17j}$;

R$^{17a}$, R$^{17c}$, R$^{17h}$ and R$^{17j}$ independently represent C$_{1-4}$ alkyl or optionally substituted aryl or R$^{17a}$, R$^{17c}$ and R$^{17h}$ independently represent H;

A represents C$_{2-4}$ alkylene optionally substituted by one or more substituents selected from —OH and amino;

B represents -Z$^1$-, -Z$^2$-N(H)—, -Z$^2$-C(O)N(R$^{19b}$)—, -Z$^2$-S(O)$_2$—, -Z$^2$-N(H)S(O)$_2$—, -Z$^2$-S(O)$_2$N(H)— or -Z$^2$-O— (in which latter six groups, Z$^2$ is attached to the nitrogen atom bearing R$^2$);

Z$^1$ represents a direct bond or C$_{1-4}$ alkylene;

Z$^2$ represents C$_{2-4}$ alkylene;

R$^{19b}$ represents H, C$_{1-4}$ alkyl, or, together with a single R$^4$ substituent at a position on the phenyl or pyridyl group that is ortho- to the position at which the group B is attached, R$^{19b}$ represents C$_{2-4}$ alkylene;

when G represents N, G is in the ortho- or, in particular, the para-position relative to the point of attachment of B;

when G represents N, R$^4$ is absent or represents a single cyano group;

R$^4$ is absent (i.e. represents H) or represents one or more substituents selected from —OH, cyano, halo, nitro, C$_{1-6}$ alkyl, C$_{1-6}$ alkoxy, —C(O)N(R$^{22e}$)R$^{22f}$, and —N(R$^{22m}$)S(O)$_2$—C$_{1-4}$ alkyl, or an R$^4$ substituent in a position on the phenyl or pyridyl group that is ortho- to the position at which the group B is attached may, together with R$^{19b}$, represent C$_{2-4}$ alkylene;

R$^{21c}$ represents C$_{1-4}$ alkyl;

R$^{22c}$, R$^{22e}$, R$^{22f}$ and R$^{22m}$ independently represent H or C$_{1-4}$ alkyl;

R$^{41}$ to R$^{46}$ independently represent H;

optional substituents on aryl and aryloxy groups are, unless otherwise stated, one or more substituents selected from halo, cyano, nitro, C$_{1-4}$ alkyl, C$_{1-4}$ alkoxy (which latter two groups are optionally substituted by one or more halo atoms), —N(H)S(O)$_2$R$^{21b}$ and —S(O)$_2$N(H)R$^{22o}$.

More preferred compounds of the invention include those in which:

R$^1$ represents straight- or branched-chain or part cyclic/acyclic C$_{1-6}$ alkyl, which alkyl group is optionally interrupted by oxygen and/or substituted by: (i) one or more halo or OR$^{5b}$ groups; and/or (ii) one group selected from phenyl (which latter group is optionally substituted by one or more (e.g. one to three) substituents selected from halo, cyano, C$_{1-4}$ alkyl, C$_{1-3}$ alkoxy (which latter two groups are optionally substituted by one or more halo (e.g. fluoro) atoms), —C(O)—C$_{1-3}$ alkyl and —S(O)$_2$—C$_{1-4}$ alkyl), Het$^1$, —C(O)R$^{5a}$, —N(R$^6$)R$^{5c}$, —C(O)N(R$^{8a}$)R$^{5d}$, —OC(O)N(H)R$^{8b}$ and —S(O)$_2$—C$_{1-4}$ alkyl, or R$^1$ represents —C(O)OR$^7$, —C(O)N(R$^{8a}$)R$^{5d}$ or —S(O)$_2$—C$_{1-5}$ alkyl;

Het$^1$ represents a four- (e.g. five-) to ten-membered heterocyclic group containing one to three heteroatoms selected from oxygen, nitrogen and/or sulfur, which group is optionally substituted by one or more (e.g. one to three) substituents selected from halo, C$_{1-3}$ alkyl, C$_{1-3}$ alkoxy and —C(O)—C$_{1-4}$ alkyl;

R$^{5a}$, R$^{5b}$ and R$^{5d}$ independently represent H, C$_{1-5}$ alkyl, phenyl (which latter group is optionally substituted by one or more substituents selected from —OH, halo, cyano, pyrrolidin-1-yl, C$_{1-4}$ alkyl and C$_{1-5}$ alkoxy (which latter group is optionally substituted by one or more halo (e.g. fluoro) atoms)) or Het$^3$;

R$^{5c}$ represents H or C$_{1-5}$ alkyl (optionally substituted by phenyl or phenoxy, which latter two groups are optionally substituted by one to three substituents selected from halo, cyano and C$_{1-2}$ alkyl);

Het$^3$ represents a five- to ten-membered heterocyclic group containing one or two heteroatoms selected from oxygen and nitrogen, which group is optionally substituted by one or more substituents selected from oxo, C$_{1-2}$ alkyl and —C(O)—C$_{1-4}$ alkyl;

$R^6$ represents H, $C_{1-4}$ alkyl, phenyl (which latter group is optionally substituted by one or more cyano groups), —C(O)O—$C_{1-5}$ alkyl, —C(O)N($R^{10c}$)$R^{10d}$ or —S(O)$_2$$R^{10e}$;

$R^{10c}$ and $R^{10d}$ independently represent H or $C_{1-3}$ alkyl;

$R^{10e}$ represents $C_{1-5}$ alkyl (optionally substituted by one or more fluoro atoms) or phenyl (optionally substituted by one or more substituents selected from halo, $C_{1-3}$ alkyl and $C_{1-3}$ alkoxy);

$R^7$ represents $C_{1-5}$ alkyl optionally substituted by $Het^4$;

$Het^4$ represents a five- to ten-membered heterocyclic group containing one or two heteroatoms selected from oxygen and nitrogen, which group is optionally substituted by one or more substituents selected from $C_{1-2}$ alkyl and —C(O)—$C_{1-4}$ alkyl;

$R^{8a}$ and $R^{8b}$ independently represent H, $C_{1-5}$ alkyl or -D-(phenyl), the phenyl part of which latter group is optionally substituted by one or more (e.g. one to three) substituents selected from halo, $C_{1-3}$ alkyl and $C_{1-3}$ alkoxy; D represents $C_{1-3}$ alkylene (e.g. $CH_2$ or $C(CH_3)_2$);

$R^2$ represents —S(O)$_2$$R^{3a}$ or —C(O)N($R^{3d}$)$R^{3e}$;

$R^{3a}$ represents $C_{1-4}$ alkyl (optionally substituted by phenyl or one or more halo (e.g. fluoro) atoms), phenyl (which latter group is optionally substituted by or more (e.g. one to three) substituents selected from halo, $C_{1-3}$ alkyl and $C_{1-3}$ alkoxy) or $Het^9$;

$Het^9$ represents a five- to ten-membered heterocyclic group containing one to three heteroatoms selected from oxygen, nitrogen and/or sulfur, which group is optionally substituted by one to three substituents selected from halo, $C_{1-2}$ alkyl and $C_{1-2}$ alkoxy;

$R^{3d}$ and $R^{3e}$ independently represent H or $C_{1-3}$ alkyl (which latter group is by phenyl or one or more halo (e.g. fluoro) atoms), phenyl (which latter group is optionally substituted by or more (e.g. one to three) substituents selected from halo, $C_{1-3}$ alkyl and $C_{1-3}$ alkoxy);

A represents $C_2$ n-alkylene or $C_3$ n-alkylene, which latter group is optionally substituted, in the 2-position relative to the point of attachment to the oxabispidine N-atom, by —OH;

B represents -$Z^1$-, -$Z^2$-N(H)-, -$Z^2$-C(O)N($R^{19b}$)—, -$Z^2$-S(O)$_2$— or -$Z^2$-O— (in which latter four groups, $Z^2$ is attached to the nitrogen atom bearing $R^2$);

$Z^1$ represents $C_{1-4}$ alkylene;

$Z^2$ represents $C_{2-3}$ alkylene;

$R^{19b}$, together with a single $R^4$ substituent at a position on the phenyl or pyridyl group that is ortho- to the position at which the group B is attached, represents $C_{2-3}$ alkylene;

G represents CH;

$R^4$ is absent (i.e. represents H) or represents one or two cyano groups in the ortho- and/or, particularly, the para-position relative to the point of attachment of the group B, or alternatively, when B represents -$Z^2$-C(O)N($R^{19b}$)—, (i) an $R^4$ substituent in a position on the phenyl or pyridyl group that is ortho- to the position at which the group B is attached may, together with $R^{19b}$, represent $C_{2-3}$ alkylene, and (ii) $R^4$ may further represent a nitro group in the para-position relative to the point of attachment of the group B.

Particular compounds of the invention include, for example, compounds of the Formula I, or pharmaceutically-acceptable salts thereof, wherein, unless otherwise stated, each of each variable group has any of the meanings defined hereinbefore or in paragraphs (a) to (d) hereinafter:—

(a) $R^1$ represents a $C_1$-$C_5$ alkyl group, (such as methyl, ethyl, propyl, butyl, propyl or pentyl), which is optionally substituted by a group selected from phenyl, 2-cyanophenyl, 4-cyanophenyl, 2,4-dicyano-phenyl, 2,6-dimethylphenyl, 3-methoxyphenyl, 4-methoxyphenyl, 4-acetylphenyl, 2-fluorophenyl, 3-fluorophenyl, 4-fluorophenyl, 4-chlorophenyl, 2,4-difluorophenyl, 3-pyridine, 4-pyridine, 2-chloro-3-pyridine, 6-methoxy-3-pyridine, 2,6-dichloro-4-pyridine, 4,5-dimethyl-2-furane, 3-trifluoromethylphenyl, 4-trifluoromethylphenyl, 4-chloro-phenyl, 4-(difluoromethoxy)phenyl, 4-(methylsulfonyl)phenyl, 2,5-dichlorophenyl, 3,5-dimethyl-4-isoxazole, 2,4-dimethyl-5-(1,3-thiazole), (1-methyl-2-(1H-imidazole), 2,6-dinethylphenyl, 4-tert-butylphenyl, or 2-fluoro-4-(trifluoromethyl)phenyl;

and/or optionally interrupted or terminated by an oxygen atom;

(b) $R^{41}$ to $R^{46}$ are hydrogen;

(c) $R^2$ represents methylsulfonyl, aminocarbonyl, N,N-dimethylaminocarbonyl, phenylsulfonyl, ethylsulfonyl, N-methylaminocarbonyl, trifluoromethylsulfonyl, acetyl, or isopropylsulfonyl;

(d) the group

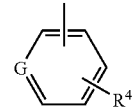

represents phenyl, 2-cyanophenyl, 3-cyanophenyl, 4-cyanophenyl, 2-fluorophenyl, 3-fluorophenyl, 4-flurophenyl, 4-(difluoromethoxy)phenyl, 2-chlorophenyl, 3-chlorophenyl, or 4-chlorophenyl.

Particularly preferred compounds of the invention include those in which:

$R^1$ represents straight- or branched-chain or part cyclic/acyclic $C_{1-6}$ alkyl, which alkyl group is optionally interrupted by oxygen and/or substituted by: (i) one or more halo or $OR^{5b}$ groups; and/or (ii) one group selected from phenyl (which latter group is optionally substituted by one or more (e.g. one to three) substituents selected from halo, cyano, $C_{1-4}$ alkyl (e.g. methyl or $C_4$ alkyl such as tert-butyl), $C_{1-2}$ alkoxy (which $C_{1-4}$ alkyl and $C_{1-2}$ alkoxy groups are optionally substituted by one or more halo (e.g. fluoro) atoms), —C(O)—$C_{1-2}$ alkyl and —S(O)$_2$—$C_{1-2}$ alkyl), $Het^1$, —C(O)$R^{5a}$, —N($R^6$)$R^{5c}$, —C(O)N(H)$R^{8a}$ and —S(O)$_2$—$C_{1-4}$ alkyl;

$Het^1$ represents a five- or six-membered heterocyclic group containing one or two heteroatoms selected from oxygen, nitrogen and/or sulfur, which group is optionally substituted by one or more (e.g. one or two) substituents selected from halo (e.g. chloro), $C_{1-2}$ alkyl and $C_{1-2}$ alkoxy;

$R^{5a}$ and $R^{5b}$ independently represent phenyl optionally substituted by one to three substituents selected from halo, $C_{1-2}$ alkyl and $C_{1-2}$ alkoxy;

$R^{5c}$ represents $C_{1-3}$ alkyl substituted by phenyl or phenoxy (which latter two groups are optionally substituted by one or two cyano groups);

$R^6$ represents H, $C_{1-4}$ alkyl, —C(O)O—$C_{1-5}$ alkyl —C(O)N($R^{10c}$)$R^{10d}$ or —S(O)$_2$$R^{10e}$;

$R^{10c}$ and $R^{10d}$ independently represent H or $C_{1-2}$ alkyl (e.g. methyl);

$R^{10e}$ represents $C_{1-3}$ alkyl (optionally substituted by one or more fluoro atoms);

$R^{8a}$ represents $C_{1-4}$ alkyl (e.g. tert-butyl) or -D-(phenyl);

$R^2$ represents —S(O)$_2$R or —C(O)N($R^{3d}$)$R^{3e}$;

$R^{3a}$ represents $C_{1-2}$ alkyl (optionally substituted by phenyl or one or more halo (e.g. fluoro) atoms);

$R^{3d}$ and $R^{3e}$ independently represent H or $C_{1-2}$ alkyl (e.g. methyl);

A represents $C_2$ or $C_3$ n-alkylene;

B represents -$Z^1$- or -$Z^2$-O— (in which latter group $Z^2$ is attached to the nitrogen atom bearing $R^2$);

$Z^1$ represents $C_{1-3}$ alkylene;

$Z^2$ represents $C_{2-3}$ n-alkylene (e.g. $C_2$ n-alkylene);

$R^4$ is absent (i.e. represents H) or represents a cyano group in the para-position relative to the point of attachment of the group B.

Especially preferred compounds of the invention include those in which:

$R^1$ represents straight- or branched-chain $C_{1-3}$ alkyl substituted by $OR^{5b}$, phenyl (which latter group is optionally substituted by one or two substituents selected from halo (e.g. fluoro or chloro), cyano, tert-butyl, methyl, methoxy (which latter two groups are optionally substituted by one to three fluoro atoms), —C(O)CH$_3$ and —S(O)$_2$CH$_3$), Het$^1$, —C(O)R$^{5a}$, —N(R$^6$)R$^{5c}$, —N(H)C$_{3-4}$ alkyl or —C(O)N(H)R$^{8a}$;

Het$^1$ represents an aromatic five- or six-membered heterocyclic group containing one or two heteroatoms selected from oxygen, nitrogen and/or sulfur, which group is optionally substituted by one or two substituents selected from chloro, methyl and methoxy;

$R^{5a}$ and $R^{5b}$ independently represent phenyl optionally substituted by one or two methyl or methoxy groups;

$R^{5c}$ represents H or benzyl;

$R^6$ represents —C(O)O—C$_{3-4}$ alkyl, —C(O)N(R$^{10c}$)R$^{10d}$ or —S(O)$_2$CH$_3$;

$R^{10c}$ and $R^{10d}$ independently represent methyl or, preferably, H;

$R^{8a}$ represents tert-butyl, CH$_2$-phenyl or C(CH$_3$)$_2$-phenyl;

$R^2$ represents —C(O)N(CH$_3$)$_2$, —C(O)N(H)CH$_3$, —C(O)NH$_2$, or, particularly, —S(O)$_2$CH$_3$;

A represents —(CH$_2$)$_2$—;

B represents —(CH$_2$)$_{1-3}$— (e.g. —CH$_2$— or —(CH$_2$)$_3$—) or —(CH$_2$)$_2$—O— (in which latter group, the —(CH$_2$)$_2$— part is attached to the nitrogen atom bearing $R^2$).

Preferred compounds of the invention include the compounds of the Examples disclosed hereinafter. In this respect, preferred compounds of the invention that might be mentioned include:

(i) tert-butyl [2-(7-{2-[[2-(4-cyanophenoxy)ethyl](methylsulfonyl)-amino]ethyl}-9-oxa-3,7-diazabicyclo[3.3.1]non-3-yl)ethyl]-carbamate;

(ii) tert-butyl {2-[7-(2-{(aminocarbonyl)[2-(4-cyanophenoxy)ethyl]-amino}ethyl)-9-oxa-3,7-diazabicyclo[3.3.1]non-3-yl]ethyl}-carbamate;

(iii) N-[2-(4-cyanophenoxy)ethyl]-N-(2-{7-[2-(4-methoxyphenyl)-2-oxoethyl]-9-oxa-3,7-diazabicyclo[3.3.1]non-3-yl}ethyl)-methanesulfonamide;

(iv) N-[2-(4-cyanophenoxy)ethyl]-N-(2-{7-[2-(4-methoxyphenyl)-2-oxoethyl]-9-oxa-3,7-diazabicyclo[3.3.1]non-3-yl}ethyl)urea;

(v) N-[2-(7-benzyl-9-oxa-3,7-diazabicyclo[3.3.1]non-3-yl)ethyl]-N-[2-(4-cyanophenoxy)ethyl]methanesulfonamide;

(vi) N-[2-(7-benzyl-9-oxa-3,7-diazabicyclo[3.3.1]non-3-yl)ethyl]-N-[2-(4-cyanophenoxy)ethyl]urea;

(vii) 2-[7-(2-{(aminocarbonyl)[2-(4-cyanophenoxy)ethyl]amino}ethyl)-9-oxa-3,7-diazabicyclo[3.3.1]non-3-yl]-N-(tert-butyl)acetamide;

(viii) 2-[7-(2-{(aminocarbonyl)[2-(4-cyanophenoxy)ethyl]amino}ethyl)-9-oxa-3,7-diazabicyclo[3.3.1]non-3-yl]-N-benzylacetamide;

(ix) 2-[7-(2-{(aminocarbonyl)[2-(4-cyanophenoxy)ethyl]amino}ethyl)-9-oxa-3,7-diazabicyclo[3.3.1]non-3-yl]-N-(1-methyl-1-phenylethyl)acetamide;

(x) N-(tert-butyl)-2-(7-{2-[[2-(4-cyanophenoxy)ethyl](methylsulfonyl)-amino]ethyl}-9-oxa-3,7-diazabicyclo[3.3.1]non-3-yl)acetamide;

(xi) N-benzyl-2-(7-{2-[[2-(4-cyanophenoxy)ethyl](methylsulfonyl)-amino]ethyl}-9-oxa-3,7-diazabicyclo[3.3.1]non-3-yl)acetamide;

(xii) 2-(7-{2-[[2-(4-cyanophenoxy)ethyl](methylsulfonyl)amino]ethyl}-9-oxa-3,7-diazabicyclo[3.3.1]non-3-yl)-N-(1-methyl-1-phenyl-ethyl)acetamide;

(xiii) tert-butyl [2-(7-{2-[[3-(4-cyanophenyl)propyl](methylsulfonyl)-amino]ethyl}-9-oxa-3,7-diazabicyclo[3.3.1]non-3-yl)ethyl]-carbamate;

(xiv) N-(tert-butyl)-2-(7-{2-[[3-(4-cyanophenyl)propyl](methylsulfonyl)-amino]ethyl}-9-oxa-3,7-diazabicyclo[3.3.1]non-3-yl)acetamide;

(xv) N-[2-(7-benzyl-9-oxa-3,7-diazabicyclo[3.3.1]non-3-yl)ethyl]-N-[3-(4-cyanophenyl)propyl]methanesulfonamide;

(xvi) N-[2-(4-cyanophenoxy)ethyl]-N-(2-{7-[2-(2,6-dimethylphenoxy)-ethyl]-9-oxa-3,7-diazabicyclo[3.3.1]non-3-yl}ethyl)urea;

(xvii) N-[2-(4-cyanophenoxy)ethyl]-N-(2-{7-[2-(4-cyanophenyl)ethyl]-9-oxa-3,7-diazabicyclo[3.3.1]non-3-yl}ethyl)urea;

(xviii) N-[2-(4-cyanophenoxy)ethyl]-N-(2-{7-[2-(4-methoxyphenyl)ethyl]-9-oxa-3,7-diazabicyclo[3.3.1]non-3-yl}ethyl)urea;

(xix) N-(2-{7-[2-(4-acetylphenyl)ethyl]-9-oxa-3,7-diazabicyclo-[3.3.1]non-3-yl}ethyl)-N-[2-(4-cyanophenoxy)ethyl]urea;

(xx) N-[2-(4-cyanophenoxy)ethyl]-N-{2-[7-(2-phenylethyl)-9-oxa-3,7-diazabicyclo[3.3.1]non-3-yl]ethyl}urea;

(xxi) N-[2-(4-cyanophenoxy)ethyl]-N-(2-{7-[2-(3-fluorophenyl)ethyl]-9-oxa-3,7-diazabicyclo[3.3.1]non-3-yl}ethyl)urea;

(xxii) N-(2-{7-[(2-chloropyridin-3-yl)methyl]-9-oxa-3,7-diazabicyclo-[3.3.1]non-3-yl}ethyl)-N-[2-(4-cyanophenoxy)ethyl]methane-sulfonamide;

(xxiii) N-[2-(4-cyanophenoxy)ethyl]-N-(2-{7-[(6-methoxypyridin-3-yl)methyl]-9-oxa-3,7-diazabicyclo[3.3.1]non-3-yl}ethyl)-methanesulfonamide;

(xxiv) N-[2-(4-cyanophenoxy)ethyl]-N-(2-{7-[(4,5-dimethyl-2-furyl)-methyl]-9-oxa-3,7-diazabicyclo[3.3.1]non-3-yl}ethyl)-methanesulfonamide;

(xxv) N-[2-(4-cyanophenoxy)ethyl]-N-{2-[7-(4-fluorobenzyl)-9-oxa-3,7-diazabicyclo[3.3.1]non-3-yl]ethyl}methanesulfonamide;

(xxvi) N-[2-(4-cyanophenoxy)ethyl]-N-(2-{7-[4-(trifluoromethyl)benzyl]-9-oxa-3,7-diazabicyclo[3.3.1]non-3-yl}ethyl)methanesulfonamide;

(xxvii) N-{2-[7-(4-chlorobenzyl)-9-oxa-3,7-diazabicyclo[3.3.1]non-3-yl]ethyl}-N-[2-(4-cyanophenoxy)ethyl]methanesulfonamide;

(xxviii) N-[2-(4-cyanophenoxy)ethyl]-N-(2-{7-[4-(difluoromethoxy)-benzyl]-9-oxa-3,7-diazabicyclo[3.3.1]non-3-yl}ethyl)-methanesulfonamide;

(xxix) N-[2-(4-cyanophenoxy)ethyl]-N-(2-{7-[4-(methylsulfonyl)benzyl]-9-oxa-3,7-diazabicyclo[3.3.1]non-3-yl}ethyl)methanesulfonamide;

(xxx) N-[2-(4-cyanophenoxy)ethyl]-N-{2-[7-(2-fluorobenzyl)-9-oxa-3,7-diazabicyclo[3.3.1]non-3-yl]ethyl}methanesulfonamide;

(xxxi) N-[2-(4-cyanophenoxy)ethyl]-N-{2-[7-(2,4-difluorobenzyl)-9-oxa-3,7-diazabicyclo[3.3.1]non-3-yl]ethyl}methanesulfonamide;

(xxxii) N-[2-(4-cyanophenoxy)ethyl]-N-{2-[7-(2,5-dichlorobenzyl)-9-oxa-3,7-diazabicyclo[3.3.1]non-3-yl]ethyl}methanesulfonamide;

(xxxiii) N-[2-(4-cyanophenoxy)ethyl]-N-(2-{7-[3-(trifluoromethyl)benzyl]-9-oxa-3,7-diazabicyclo[3.3.1]non-3-yl}ethyl)methanesulfonamide;

(xxxiv) N-{2-[7-(4-cyanobenzyl)-9-oxa-3,7-diazabicyclo[3.3.1]non-3-yl]ethyl}-N-[2-(4-cyanophenoxy)ethyl]methanesulfonamide;

(xxxv) N-{2-[7-(2-cyanobenzyl)-9-oxa-3,7-diazabicyclo[3.3.1]non-3-yl]ethyl}-N-[2-(4-cyanophenoxy)ethyl]methanesulfonamide;

(xxxvi) N-[2-(4-cyanophenoxy)ethyl]-N-(2-{7-[(2,6-dichloropyridin-4-yl)methyl]-9-oxa-3,7-diazabicyclo[3.3.1]non-3-yl}ethyl)-methanesulfonamide;

(xxxvii) N-[2-(4-cyanophenoxy)ethyl]-N-{2-[7-(pyridin-4-ylmethyl)-9-oxa-3,7-diazabicyclo[3.3.1]non-3-yl]ethyl}methanesulfonamide;

(xxxviii) N-[2-(4-cyanophenoxy)ethyl]-N-{2-[7-(pyridin-3-ylmethyl)-9-oxa-3,7-diazabicyclo[3.3.1]non-3-yl]ethyl}methanesulfonamide;

(xxxix) N-[2-(4-cyanophenoxy)ethyl]-N-(2-{7-[(3,5-dimethylisoxazol-4-yl)methyl]-9-oxa-3,7-diazabicyclo[3.3.1]non-3-yl}ethyl)-methanesulfonamide;

(xl) N-[2-(4-cyanophenoxy)ethyl]-N-(2-{7-[(2,4-dimethyl-1,3-thiazol-5-yl)methyl]-9-oxa-3,7-diazabicyclo[3.3.1]non-3-yl}ethyl)methane-sulfonamide;

(xli) N-[2-(4-cyanophenoxy)ethyl]-N-(2-{7-[(1-methyl-1H-imidazol-2-yl)methyl]-9-oxa-3,7-diazabicyclo[3.3.1]non-3-yl}ethyl)-methanesulfonamide;

(xlii) N-benzyl-N-{2-[7-(4-cyanobenzyl)-9-oxa-3,7-diazabicyclo-[3.3.1]non-3-yl]ethyl}methanesulfonamide;

(xliii) N-[2-(4-cyanophenoxy)ethyl]-N-{2-[7-(3-phenylpropyl)-9-oxa-3,7-diazabicyclo[3.3.1]non-3-yl]ethyl}methanesulfonamide;

(xliv) N-[2-(4-cyanophenoxy)ethyl]-N-(2-{7-[3-(4-cyanophenyl)propyl]-9-oxa-3,7-diazabicyclo[3.3.1]non-3-yl}ethyl)methanesulfonamide;

(xlv) N-[2-(4-cyanophenoxy)ethyl]-N-(2-{7-[3-(3-methoxyphenyl)-propyl]-9-oxa-3,7-diazabicyclo[3.3.1]non-3-yl}ethyl)methane-sulfonamide;

(xlvi) N-[2-(4-cyanophenoxy)ethyl]-N-{2-[7-(2,6-dimethylbenzyl)-9-oxa-3,7-diazabicyclo[3.3.1]non-3-yl]ethyl}methanesulfonamide;

(xlvii) N-{2-[7-(4-tert-butylbenzyl)-9-oxa-3,7-diazabicyclo[3.3.1]non-3-yl]ethyl}-N-[2-(4-cyanophenoxy)ethyl]methanesulfonamide;

(xlviii) N-[2-(7-benzyl-9-oxa-3,7-diazabicyclo[3.3.1]non-3-yl)ethyl]-N-[2-(4-cyanophenoxy)ethyl]-N',N'-dimethylurea;

(xlix) N-{2-[7-(4-cyanobenzyl)-9-oxa-3,7-diazabicyclo[3.3.1]non-3-yl]ethyl}-N-[2-(4-cyanophenoxy)ethyl]-N',N'-dimethylurea;

(l) N-[2-(4-cyanophenoxy)ethyl]-N-(2-{7-[2-fluoro-4-(trifluoro-methyl)benzyl]-9-oxa-3,7-diazabicyclo[3.3.1]non-3-yl}ethyl)-N',N'-dimethylurea;

(li) N-[2-(4-cyanophenoxy)ethyl]-N-{2-[7-(4-fluorobenzyl)-9-oxa-3,7-diazabicyclo[3.3.1]non-3-yl]ethyl}-N',N'-dimethylurea;

(lii) N-[2-(4-cyanophenoxy)ethyl]-N-(2-{7-[4-(difluoromethoxy)-benzyl]-9-oxa-3,7-diazabicyclo[3.3.1]non-3-yl}ethyl)-N',N'-dimethylurea;

(liii) N-[2-(4-cyanophenoxy)ethyl]-N',N'-dimethyl-N-{2-[7-(2-phenyl-ethyl)-9-oxa-3,7-diazabicyclo[3.3.1]non-3-yl]ethyl}urea;

(liv) N-[2-(4-cyanophenoxy)ethyl]-N-(2-{7-[2-(4-cyanophenyl)ethyl]-9-oxa-3,7-diazabicyclo[3.3.1]non-3-yl}ethyl)-N',N'-dimethylurea;

(lv) N-[2-(4-cyanophenoxy)ethyl]-N-(2-{7-[2-(3-fluorophenyl)ethyl]-9-oxa-3,7-diazabicyclo[3.3.1]non-3-yl}ethyl)-N',N'-dimethylurea;

(lvi) N-[2-(4-cyanophenoxy)ethyl]-N',N'-dimethyl-N-{2-[7-(3-phenyl-propyl)-9-oxa-3,7-diazabicyclo[3.3.1]non-3-yl]ethyl}urea;

(lvii) N-[2-(4-cyanophenoxy)ethyl]-N-{2-[7-(2-phenyl-ethyl)-9-oxa-3,7-diazabicyclo[3.3.1]non-3-yl]ethyl}methanesulfonamide;

(lviii) N-[2-(4-cyanophenoxy)ethyl]-N-(2-{7-[2-(4-cyanophenyl)ethyl]-9-oxa-3,7-diazabicyclo[3.3.1]non-3-yl}ethyl)methanesulfonamide;

(lix) N-[2-(4-cyanophenoxy)ethyl]-N-(2-{7-[2-(4-fluorophenyl)ethyl]-9-oxa-3,7-diazabicyclo[3.3.1]non-3-yl}ethyl)methanesulfonamide;

(lx) N-benzyl-N-(2-{7-[2-(4-cyanophenoxy)ethyl]-9-oxa-3,7-diazabicyclo[3.3.1]non-3-yl}ethyl)methanesulfonamide;

(lxi) N-(2-{7-[2-(4-cyanophenoxy)ethyl]-9-oxa-3,7-diazabicyclo-[3.3.1]non-3-yl}ethyl)-N-(2-phenylethyl)methanesulfonamide;

(lxii) N-(2-{7-[3-(4-cyanophenoxy)propyl]-9-oxa-3,7-diazabicyclo-[3.3.1]non-3-yl}ethyl)-N-(2-phenylethyl)methanesulfonamide;

(lxiii) N-(2-{7-[2-(4-cyanophenoxy)ethyl]-9-oxa-3,7-diazabicyclo-[3.3.1]non-3-yl}ethyl)-N-(2-phenoxyethyl)methanesulfonamide;

(lxiv) N-{2-[7-(4-cyanobenzyl)-9-oxa-3,7-diazabicyclo[3.3.1]non-3-yl]ethyl}-N-(2-phenoxyethyl)methanesulfonamide;

(lxv) N-{2-[7-(4-cyanobenzyl)-9-oxa-3,7-diazabicyclo[3.3.1]non-3-yl]ethyl}-N-(2-phenylethyl)methanesulfonamide;

(lxvi) N-(2-{7-[3-(4-cyanophenoxy)propyl]-9-oxa-3,7-diazabicyclo-[3.3.1]non-3-yl}ethyl)-N-(2-phenoxyethyl)methanesulfonamide;

(lxvii) N-benzyl-N-{2-[7-(4-fluorobenzyl)-9-oxa-3,7-diazabicyclo-[3.3.1]non-3-yl]ethyl}methanesulfonamide;

(lxviii) N-benzyl-N-{2-[7-(4-chlorobenzyl)-9-oxa-3,7-diazabicyclo-[3.3.1]non-3-yl]ethyl}methanesulfonamide;

(lxix) N-benzyl-N-{2-[7-(4-cyanobenzyl)-9-oxa-3,7-diazabicyclo-[3.3.1]non-3-yl]ethyl}benzenesulfonamide;

(lxx) N-(4-cyanobenzyl)-N-{2-[7-(4-cyanobenzyl)-9-oxa-3,7-diazabicyclo[3.3.1]non-3-yl]ethyl}methanesulfonamide;

(lxxi) N-(2-cyanobenzyl)-N-{2-[7-(4-cyanobenzyl)-9-oxa-3,7-diazabicyclo[3.3.1]non-3-yl]ethyl}methanesulfonamide;

(lxxii) N-{2-[7-(4-cyanobenzyl)-9-oxa-3,7-diazabicyclo[3.3.1]non-3-yl]ethyl}-N-(4-fluorobenzyl)methanesulfonamide;

(lxxiii) N-{2-[7-(4-cyanobenzyl)-9-oxa-3,7-diazabicyclo[3.3.1]non-3-yl]ethyl}-N-(3-fluorobenzyl)methanesulfonamide;

(lxxiv) N-{2-[7-(4-cyanobenzyl)-9-oxa-3,7-diazabicyclo[3.3.1]non-3-yl]ethyl}-N-[4-(difluoromethoxy)benzyl]methanesulfonamide;

(lxxv) N-(4-chlorobenzyl)-N-{2-[7-(4-cyanobenzyl)-9-oxa-3,7-diazabicyclo[3.3.1]non-3-yl]ethyl}methanesulfonamide;

(lxxvi) N-benzyl-N-{2-[7-(4-cyanobenzyl)-9-oxa-3,7-diazabicyclo-[3.3.1]non-3-yl]ethyl}ethanesulfonamide;

(lxxvii) N-benzyl-N-{2-[7-(4-cyanobenzyl)-9-oxa-3,7-diazabicyclo-[3.3.1]non-3-yl]ethyl}-N'-methylurea;

(lxxviii) N-benzyl-N-{2-[7-(4-cyanobenzyl)-9-oxa-3,7-diazabicyclo-[3.3.1]non-3-yl]ethyl}-N',N'-dimethylurea;

(lxxix) N-benzyl-N-(2-{7-[2-(4-cyanophenyl)ethyl]-9-oxa-3,7-diazabicyclo[3.3.1]non-3-yl}ethyl)methanesulfonamide;

(lxxx) N-benzyl-N-(2-{7-[2-(2,4-dicyanophenoxy)ethyl]-9-oxa-3,7-diazabicyclo[3.3.1]non-3-yl}ethyl)methanesulfonamide;

(lxxxi) N-benzyl-N-(2-{7-[3-(4-cyanophenoxy)propyl]-9-oxa-3,7-diazabicyclo[3.3.1]non-3-yl}ethyl)methanesulfonamide;

(lxxxii) N-benzyl-N-{2-[7-(4-cyanobenzyl)-9-oxa-3,7-diazabicyclo-[3.3.1]non-3-yl]ethyl}-1,1,1-trifluoromethanesulfonamide;

(lxxxiii) N-benzyl-N-{2-[7-(4-cyanobenzyl)-9-oxa-3,7-diazabicyclo-[3.3.1]non-3-yl]ethyl}acetamide;

(lxxxiv) N-benzyl-N-{2-[7-(4-cyanobenzyl)-9-oxa-3,7-diazabicyclo-[3.3.1]non-3-yl]ethyl}urea;

(lxxxv) N-benzyl-N-{2-[7-(4-cyanobenzyl)-9-oxa-3,7-diazabicyclo-[3.3.1]non-3-yl]ethyl}propane-2-sulfonamide; and (lxxxvi) N-{2-[7-(4-cyanobenzyl)-9-oxa-3,7-diazabicyclo[3.3.1]non-3-yl]ethyl}-N-(4-fluorobenzyl)urea;

or a pharmaceutically acceptable derivative thereof.

Preparation

According to the invention there is also provided a process for the preparation of compounds of formula I which comprises:

(a) reaction of a compound of formula II,

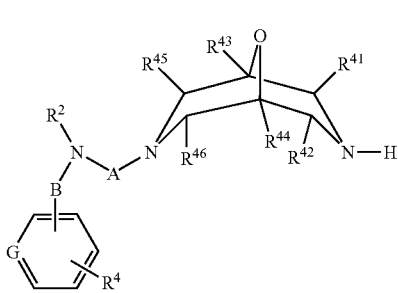

wherein $R^2$, $R^4$, $R^{41}$ to $R^{46}$, A, B and G are as hereinbefore defined, with a compound of formula III, $R^1$-$L^1$  III wherein $L^1$ represents a leaving group such as halo, alkanesulfonate, perfluoroalkanesulfonate, arenesulfonate, —OC(O)$XR^7$, imidazole or $R^{23}$O— (wherein $R^{23}$ represents, for example, $C_{1-10}$ alkyl or aryl, which groups are optionally substituted by one or more halo or nitro groups) and X, $R^1$ and $R^7$ are as hereinbefore defined, for example at between room and reflux temperature in the presence of a suitable base (e.g. triethylamine, potassium carbonate or a bicarbonate, such as sodium bicarbonate) and an appropriate solvent (e.g. dichloromethane, chloroform, acetonitrile, N,N-dimethylformamide, TBIF, toluene, water, a lower alkyl alcohol (e.g. ethanol) or mixtures thereof);

(b) for compounds of formula I in which $R^1$ represents —C(O)$XR^7$ or —C(O)N($R^{8a}$)$R^{5d}$, reaction of a compound of formula IV,

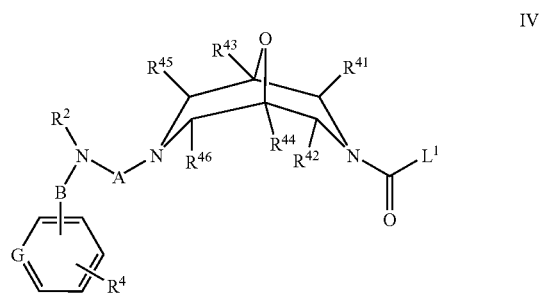

wherein $R^2$, $R^4$, $R^{41}$ to $R^{46}$, A, B, G and $L^1$ are as hereinbefore defined, with a compound of formula V, $R^{24}$—H  V wherein $R^{24}$ represents —$XR^7$ or —N($R^{8a}$)$R^{5d}$ and $R^{5d}$, $R^7$, $R^{8a}$ and X are as hereinbefore defined, for example under similar conditions to those described hereinbefore (process step (a));

(c) for compounds in which $R^1$ represents —C(O)N(H)$R^{8a}$, reaction of a compound of formula II, as hereinbefore defined, with a compound of formula VI, $R^{8a}$—N=C=O  VI wherein $R^{8a}$ is as hereinbefore defined, for example at between 0° C. and reflux temperature in the presence of an appropriate organic solvent (e.g. dichloromethane), or via solid phase synthesis under conditions known to those skilled in the art;

(d) reaction of a compound of formula VII,

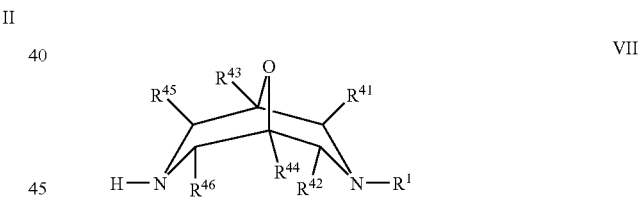

wherein $R^1$ and $R^{41}$ to $R^{46}$ are as hereinbefore defined, with a compound of formula VIII,

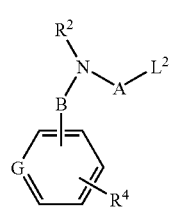

wherein $L^2$ represents a leaving group such as halo, alkanesulfonate (e.g. mesylate), perfluoroalkanesulfonate or arenesulfonate (e.g. benzenesulfonate, 2- or 4-nitrobenzenesulfonate or, particularly, toluenesulfonate) and $R^2$, $R^4$, A, B and G are as hereinbefore defined, for example at elevated temperature (e.g. between 35° C. and reflux temperature) in the presence of a suitable base (e.g. triethylamine or potassium carbonate) and an appropriate organic solvent (e.g. acetonitrile, dichloromethane, chloroform, dimethylsulfoxide, N,N-dimethylformamide, a lower alkyl alcohol (e.g. ethanol), isopropyl acetate or mixtures thereof);

(e) for compounds of formula I in which A represents $C_{3-6}$ alkylene substituted in the 2-position (relative to the oxabispidine N-atom) by —OH or amino, reaction of a compound of formula VII, as hereinbefore defined, with a compound of formula IX,

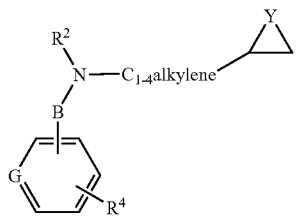

IX or a protected derivative thereof, wherein Y represents O or NH and $R^2$, $R^4$, B and G are as hereinbefore defined, for example at elevated temperature (e.g. 60° C. to reflux) in the presence of a suitable solvent (e.g. a lower alkyl alcohol (e.g. IPA), acetonitrile, or a mixture of a lower alkyl alcohol and water);

(f) for compounds of formula I in which B represents $-Z^2$-Q-, reaction of a compound of formula X,

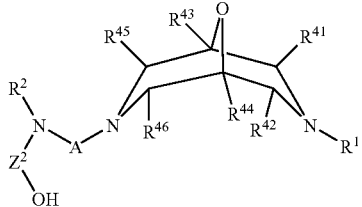

X wherein $R^1$, $R^2$, $R^{41}$ to $R^{46}$, A and $Z^2$ are as hereinbefore defined, with a compound of formula XI,

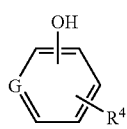

XI wherein $R^4$ and G are as hereinbefore defined, for example under Mitsunobu-type conditions e.g. at between ambient (e.g. 25° C.) and reflux temperature in the presence of a tertiary phosphine (e.g. tributylphosphine or triphenylphosphine), an azodicarboxylate derivative (e.g. diethylazodicarboxylate or 1,1'-(azodicarbonyl)dipiperidine) and an appropriate organic solvent (e.g. dichloromethane or toluene);

(g) for compounds of formula I in which G represents N and B represents $-Z^2$-O—, reaction of a compound of formula X, as hereinbefore defined, with a compound of formula XII,

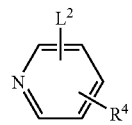

XII wherein $R^4$ and $L^2$ are as hereinbefore defined, for example at between 10° C. and reflux temperature in the presence of a suitable base (e.g. sodium hydride) and an appropriate solvent (e.g. N,N-dimethylformamide);

(h) for compounds of formula I in which B is as hereinbefore defined, except that it does not represent a direct bond, reaction of a compound of formula XIII.

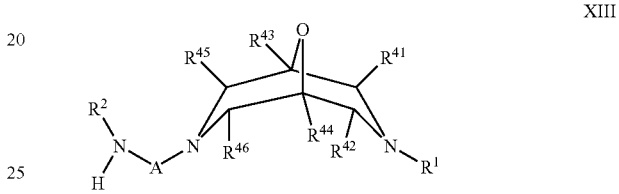

XIII wherein $R^1$, $R^2$, $R^{41}$ to $R^{46}$ and A are as hereinbefore defined, with a compound of formula XIV,

XIV wherein $B^a$ represents B as hereinbefore defined, except that it does not represent a direct bond, and $R^4$, G, and $L^2$ are as hereinbefore defined, for example at elevated temperature (e.g. between 35° C. and reflux temperature) in the presence of a suitable base (e.g. triethylamine or potassium carbonate) and an appropriate organic solvent (e.g. acetonitrile, dichloromethane, chloroform, dimethylsulfoxide, N,N-dimethylformamide, a lower alkyl alcohol (e.g. ethanol), isopropyl acetate or mixtures thereof);

(i) reaction of a compound of formula XV,

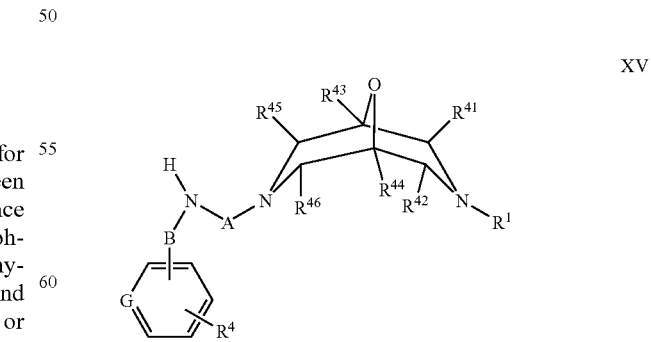

XV wherein $R^1$, $R^4$, $R^{41}$ to $R^{46}$, A, B and G are as hereinbefore defined, with a compound of formula XVI, $R^2$-$L^3$

XVI wherein $L^3$ represents a suitable leaving group (such as halo, $-OS(O)_2R^{3a}$, $-OC(O)OR^{3b}$, $-OC(O)R^{3c}$ or $-NH_2$), and $R^2$ is as hereinbefore defined, for example under conditions known to those skilled in the art (such as: (1) when $R^2$ represents $-S(O)_2R^{3a}$, $-C(O)N(R^{3d})(R^{3e})$ or $S(O)_2N(R^{3f})(R^{3g})$ and $L^3$ represents halo or $-OS(O)_2R^{3a}$, reaction at between sub-ambient temperature (e.g. 0 to 10° C.) and ambient temperature (e.g. 20 to 30° C.) in the presence of a suitable base (e.g. triethylamine) and an appropriate solvent (e.g. DCM); and (2) when $R^2$ represents $-C(O)N(R^{3d})(R^{3e})$ and $L^3$ represents $-N(R^{3d})(R^{3e})$, reaction at elevated temperature (e.g. 110 to 150° C., such as 130° C.));

(j) for compounds of formula I in which $R^2$ represents $-C(O)N(H)R^{3d}$, reaction of a compound of formula XV, as hereinbefore defined, with a compound of formula XVII

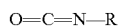  XVII wherein R represents a monovalent metal cation (e.g. an alkali metal cation, such as a potassium ion) or R represents $R^{3d}$ as hereinbefore defined, except that it does not represent H, for example under conditions known to those skilled in the art (such as when R represents a potassium ion, reaction at ambient temperature (e.g. 15 to 30° C.) in the presence of a suitable acid (e.g. acetic acid) and an appropriate solvent (e.g. 1,4-dioxane, water, or a mixture thereof);

(k) for compounds of formula I in which $R^1$ represents $C_{1-12}$ alkyl substituted by one or more substituents as defined above in respect of $R^1$, which substituent(s) is/include a $-N(R^{9b})S(O)_2R^{9d}$ group, reaction of a compound of formula XVIII,

XVIII

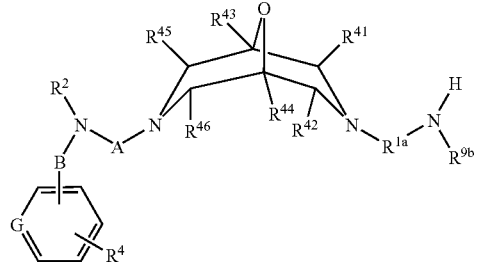

wherein $R^{1a}$ represents $C_{1-12}$ alkylene, which group is optionally substituted by one or more substituents as defined above in respect of $R^1$, and $R^2$, $R^4$, $R^{9b}$, $R^{41}$ to $R^{46}$, A, B and G are as hereinbefore defined, with a compound of formula XIX,

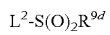  XIX wherein $R^{9d}$ and $L^2$ are as hereinbefore defined, for example under conditions that are know to those skilled in the art (e.g. at ambient temperature (such as from 15 to 30° C.) in the presence of a suitable base (such as such as triethylamine, potassium carbonate or sodium hydrogencarbonate) and an appropriate solvent (such as DCM, CHCl$_3$, acetonitrile, DMF, THF, toluene, or mixtures thereof);

(l) for compounds of formula I in which $R^1$ represents $C_{1-12}$ alkyl substituted by one or more substituents as defined above in respect of $R^1$, which substituent(s) is/include a $-S(O)_2N(R^{9b})R^{9c}$ or $-N(R^{9b})S(O)_2R^{9d}$ group, reaction of a compound of formula II, as hereinbefore defined, with a compound of formula XIXA or XIXB,

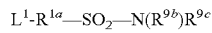  XIXA

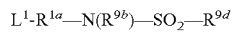  XIXB wherein $L^1$, $R^{1a}$, $R^{9b}$, $R^{9c}$ and $R^{9d}$ are as hereinbefore defined, for example under conditions that are know to those skilled in the art (e.g. at ambient temperature to reflux in the presence of a suitable base (such as such as triethylamine, potassium carbonate or sodium hydrogencarbonate) and an appropriate solvent (such as DCM, CHCl$_3$, acetonitrile, DMF, THF, toluene, or mixtures thereof);

(m) for compounds of formula I in which $R^1$ represents $-C(O)XR^7$, $-C(O)N(R^{8a})R^{5d}$ or $-S(O)_2R^{9a}$, reaction of a compound of formula XX,

XX

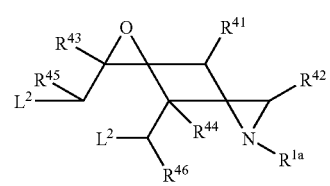

wherein $R^{1a}$ represents $-C(O)XR^7$, $-C(O)N(R^{5a})R^{5d}$ or $-S(O)_2R^{9a}$ and $R^{5d}$, $R^7$, $R^{8a}$, $R^{9a}$, $R^{41}$ to $R^{46}$ and $L^2$ are as hereinbefore defined, with a compound of formula XXI,

XXI

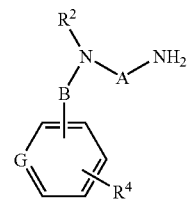

wherein $R^2$, $R^4$, A, B and G are as hereinbefore defined, for example at between room and reflux temperature in the presence of a suitable base (e.g. sodium hydrogencarbonate or potassium carbonate) and an appropriate organic solvent (e.g. acetonitrile);

(n) for compounds of formula I which are oxabispidine-nitrogen N-oxide derivatives, oxidation of the corresponding oxabispidine nitrogen of a corresponding compound of formula I, in the presence of a suitable oxidising agent (e.g. MCPBA), for example at 0° C. in the presence of a suitable organic solvent (e.g. dichloromethane);

(o) for compounds of formula I which are $C_{1-4}$ alkyl quaternary ammonium salt derivatives, in which the alkyl group is attached to a oxabispidine nitrogen, reaction, at the oxabispidine nitrogen, of a corresponding compound of formula I with a compound of formula XXII,

  XXII wherein $R^{25}$ represents $C_{1-4}$ alkyl and $L^4$ is a leaving group such as halo, alkanesulfonate or arenesulfonate, for example at room temperature in the presence of an appropriate organic solvent (e.g. N,N-dimethylformamide), followed by purification (using e.g. HPLC) in the presence of a suitable counter-ion provider (e.g. NH$_4$OAc);

(o) conversion of one $R^4$ substituent to another using techniques well known to those skilled in the art;

(p) introduction of one or more (further) $R^4$ substituents to the aromatic ring using techniques well known to those skilled in the art (e.g. chlorination);

(q) for compounds of formula I in wherein $R^1$ represents $C_{1-12}$ alkylene, which group is optionally substituted by one or more substituents as defined above in respect of $R^1$, reaction of a compound of formula II

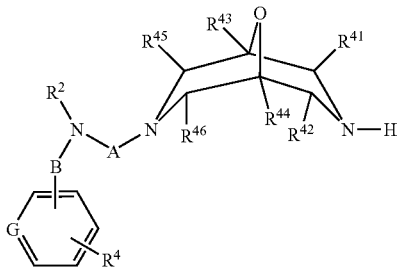

II wherein $R^2$, $R^4$, $R^{41}$ to $R^{46}$, A, B and G are as hereinbefore defined, with the appropriate aldehyde, for example under conditions that are known to those skilled in the art (e.g. at room temperature, such as from 15 to 30° C.) in the presence of a reducing agent (such as sodium cyanoborohydride, sodium triacetoxyborohydride, or similar compounds) and an appropriate solvent (such as 1,2-dichloroethane, dichloroethane, methanol, ethanol or mixtures thereof);

(r) reaction of a compound with formula VII

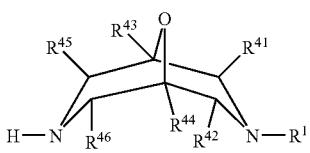

VII wherein $R^1$ and $R^{41}$ to $R^{46}$ are as hereinbefore defined, with a compound of formula XXIII

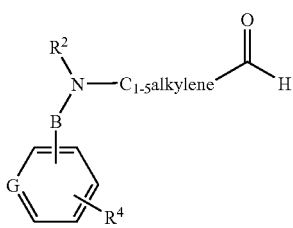

XXIII wherein $R^2$, $R^4$, B and G are as hereinbefore defined, for example under conditions that are known to those skilled in the art (e.g. at room temperature, such as from 15 to 30° C.) in the presence of a reducing agent (such as sodium cyanoborohydride, sodium triacetoxyborohydride, or similar hydride donating compounds) and an appropriate solvent (such as 1,2-dichloroethane, dichloroethane, methanol, ethanol or mixtures thereof); or (s) deprotection of a protected derivative of a compound of formula I as defined above.

Compounds of formulae II, IV, VII, VIII, IX, X, XIII, XV, XVIII, XX and XXI may be prepared according to or by analogy with the procedures described or referred to in WO 01/28992, WO 02/28863, WO 02/28864, WO 02/83690 and WO 02/83691, the disclosures of which documents are hereby incorporated by reference.

Compounds of formulae III, V, VI, XI, XII, XIV, XVI, XVII, XIX, XIXA, XIXB, XXII and derivatives thereof, are either commercially available, are known in the literature, or may be obtained either by analogy with the processes described herein, or by conventional synthetic procedures, in accordance with standard techniques, from readily available starting materials using appropriate reagents and reaction conditions.

Substituents on the aryl (e.g. phenyl), and (if appropriate) heterocyclic, group(s) in compounds defined herein may be converted to other claimed substituents using techniques well known to those skilled in the art. For example, hydroxy may be converted to alkoxy, phenyl may be halogenated to give halophenyl, nitro may be reduced to give amino, halo may be displaced by cyano, etc.

The skilled person will also appreciate that various standard substituent or functional group interconversions and transformations within certain compounds of formula I will provide other compounds of formulae I. For example, carbonyl may be reduced to hydroxy or alkylene, and hydroxy may be converted to halo.

The compounds of the invention may be isolated from their reaction mixtures using conventional techniques.

It will be appreciated by those skilled in the art that, in the process described above, the functional groups of intermediate compounds may be, or may need to be, protected by protecting groups.

Functional groups which it is desirable to protect include hydroxy, amino and carboxylic acid. Suitable protecting groups for hydroxy include trialkylsilyl and diarylalkylsilyl groups (e.g. tert-butyldimethylsilyl, tert-butyldiphenylsilyl or trimethylsilyl), tetrahydropyranyl and alkylcarbonyl groups (e.g. methyl- and ethylcarbonyl groups). Suitable protecting groups for amino include benzyl, sulfonamido (e.g. benzenesulfonamido), tert-butyloxycarbonyl, 9-fluorenyl-methoxycarbonyl or benzyloxycarbonyl. Suitable protecting groups for amidino and guanidino include benzyloxycarbonyl. Suitable protecting groups for carboxylic acid include $C_{1-6}$ alkyl or benzyl esters.

The protection and deprotection of functional groups may take place before or after any of the reaction steps described hereinbefore. Protecting groups may be removed in accordance with techniques which are well known to those skilled in the art and as described hereinafter.

The use of protecting groups is fully described in "Protective Groups in Organic Chemistry", edited by J. W. F. McOmie, Plenum Press (1973), and "Protective Groups in Organic Synthesis", $3^{rd}$ edition, T. W. Greene & P. G. M. Wutz, Wiley-Interscience (1999).

Persons skilled in the art will appreciate that, in order to obtain compounds of the invention in an alternative, and, on some occasions, more convenient, manner, the individual process steps mentioned herein may be performed in a different order, and/or the individual reactions may be performed at a different stage in the overall route (i.e. substituents may be added to and/or chemical transformations performed upon, different intermediates to those associated hereinbefore with a particular reaction). This will depend inter alia on factors such as the nature of other functional groups present in a particular substrate, the availability of key intermediates and the protecting group strategy (if any) to be adopted. Clearly, the type of chemistry involved will influence the choice of reagent that is used in the said synthetic steps, the need, and type, of protecting groups that are employed, and the sequence for accomplishing the synthesis.

It will also be appreciated by those skilled in the art that, although certain protected derivatives of compounds of formula I, which may be made prior to a final deprotection stage, may not possess pharmacological activity as such, they may be administered parenterally or orally and thereafter metabolised in the body to form compounds of the invention which are pharmacologically active. Such derivatives may therefore be described as "prodrugs". Moreover, certain compounds of formula I may act as prodrugs of other compounds of formula I.

All prodrugs of compounds of formula I are included within the scope of the invention.

Some of the intermediates referred to hereinbefore are novel. According to a further aspect of the invention there is thus provided: (a) a compound of formula II, as hereinbefore defined, or a protected derivative thereof; (b) a compound of formula IV, or a protected derivative thereof; (c) a compound of formula VIII, or a protected derivative thereof; (d) a compound of formula IX, or a protected derivative thereof; (e) a compound of formula X, or a protected derivative thereof; (f) a compound of formula XIII, or a protected derivative thereof; (g) a compound of formula XV, or a protected derivative thereof, provided that A is interrupted by $-S(O)_2N(R^{18a})-$ or $-N(R^{18b})S(O)_2-$ and/or B represents $-Z^1-[C(O)]_aC(H)(R^{19a})-$, $-Z^2-[C(O)]_cN(R^{19b})-$, $-Z^2-N(R^{18c})S(O)_2-$ $-Z^2-S(O)_2N(R^{18d})-$, wherein $R^{19a}$ is other than H and $R^{19b}$ is other than H or $C_{1-6}$ alkyl; (h) a compound of formula XVIII, or a protected derivative thereof; and (i) a compound of formula XXI, or a protected derivative thereof.

Medical and Pharmaceutical Use

Compounds of the invention are useful because they possess pharmacological activity. They are therefore indicated as pharmaceuticals.

Thus, according to a further aspect of the invention there is provided the compounds of the invention for use as pharmaceuticals.

In particular, the compounds of the invention exhibit myocardial electrophysiological activity, for example as demonstrated in the test described below.

The compounds of the invention are thus expected to be useful in both the prophylaxis and the treatment of arrhythmias, and in particular atrial and ventricular arrhythmias.

The compounds of the invention are thus indicated in the treatment or prophylaxis of cardiac diseases, or in indications related to cardiac diseases, in which arrhythmias are believed to play a major role, including ischaemic heart disease, sudden heart attack, myocardial infarction, heart failure, cardiac surgery and thromboembolic events.

In the treatment of arrhythmias, compounds of the invention have been found to selectively delay cardiac repolarization and increase refractoriness.

According to a further aspect of the invention, there is provided a method of treatment of an arrhythmia which method comprises administration of a therapeutically effective amount of a compound of the invention to a person suffering from, or susceptible to, such a condition.

Pharmaceutical Preparations

The compounds of the invention will normally be administered orally, subcutaneously, intravenously, intraarterially, transdermally, intranasally, by inhalation, or by any other parenteral route, in the form of pharmaceutical preparations comprising the active ingredient either as a free base or a non-toxic organic or inorganic acid addition salt, in a pharmaceutically acceptable dosage form. Depending upon the disorder and patient to be treated, as well as the route of administration, the compositions may be administered at varying doses.

The compounds of the invention may also be combined with any other drugs useful in the treatment of arrhythmias and/or other cardiovascular disorders. In particular the compounds of the invention may be combined with an anticoagulant.

When used herein, the term "an anticoagulant" includes references to one a substance selected from the group consisting of aspirin, warfarin, enoxaparin, heparin, low molecular weight heparin, cilostazol, clopidogrel, ticlopidine, tirofiban, abciximab, dipyridamole, plasma protein fraction, human albumin, low molecular weight dextran, hetastarch, reteplase, alteplase, streptokinase, urokinase, dalteparin, filgrastin, immunoglogulin, ginkolide B, hirudins, foropafant, rocepafant, bivalirudin, dermatan sulfate mediolanum, eptilibatide, tirofiban, thrombomodulin, abcxmab, low molecular weight dermatan sulfate-opocrin, eptacog alfa, argatroban, fondaparinux sodium, tifacogin, lepirudin, desirudin, OP2000, roxifiban, parnaparin sodium, human hemoglobin (Hemosol), bovine hemoglobin (Biopure), human hemoglobin (Northfield), antithrombin III, RSR 13, heparin-oral (Emisphere) transgenic antithrombin III, H37695, enoxaparin sodium, mesoglycan, CTC 111, bivalirudin, and any derivatives and/or combinations thereof.

Particular anticoagulants that may be mentioned include aspirin and warfarin.

The term "an anticoagulant" also includes references to thrombin inhibitors. Thrombin inhibitors that may be mentioned include low molecular weight thrombin inhibitors. The term "low molecular weight thrombin inhibitors" will be understood by those skilled in the art, and includes references to any composition of matter (e.g. chemical compound) that inhibits thrombin to an experimentally determinable degree (as determined by in vivo and/or in vitro tests), and which possesses a molecular weight of below about 2,000, preferably below about 1,000.

Preferred low molecular weight thrombin inhibitors include low molecular weight peptide-based, amino acid-based, and/or peptide analogue-based, thrombin inhibitors, as well as derivatives thereof.

The term "low molecular weight peptide-based, amino acid-based, and/or peptide analogue-based, thrombin inhibitors" will be well understood by one skilled in the art to include references to low molecular weight thrombin inhibitors with one to four peptide linkages, and includes those described in the review paper by Claesson in Blood Coagul. Fibrin. 5, 411 (1994), as well as those disclosed in U.S. Pat. No 4,346,078, International Patent Applications WO 93/11152, WO 93/18060, WO 93/05069, WO 94/20467, WO 94/29336, WO 95/35309, WO 95/23609, WO 96/03374, WO 96/06832, WO 96/06849, WO 96/25426, WO 96/32110, WO 97/01338, WO 97/02284, WO 97/15190, WO 97/30708, WO 97/40024, WO 97/46577, WO 98/06740, WO 97/49404, WO 97/11693, WO 97/24135, WO 97/47299, WO 98/01422, WO 98/57932, WO 99/29664, WO 98/06741, WO 99/37668, WO 99/37611, WO 98/37075, WO 99/00371, WO 99/28297, WO 99/29670, WO 99/40072, WO 99/54313, WO 96/31504, WO 00/01704 and WO 00/08014; and European Patent Applications 648 780, 468 231, 559 046, 641 779, 185 390, 526 877,542 525, 195 212, 362 002, 364 344, 530

167, 293 881, 686 642, 669 317, 601 459 and 623 596, the disclosures in all of which documents are hereby incorporated by reference.

In the present application, derivatives of thrombin inhibitors include chemical modifications, such as esters, prodrugs and metabolites, whether active or inactive, and pharmaceutically acceptable salts and solvates, such as hydrates, of any of these, and solvates of any such salt.

Preferred low molecular weight peptide-based thrombin inhibitors include those known collectively as the "gatrans". Particular gatrans which may be mentioned include HOOC—CH$_2$—(R)Cha-Pic-Nag-H (known as inogatran) and HOOC—CH$_2$—(R)Cgl-Aze-Pab-H (known as melagatran) (see International Patent Application WO 93/11152 and WO 94/29336, respectively, and the lists of abbreviations contained therein).

International Patent Application WO 97/23499 discloses a number of compounds which have been found to be useful as prodrugs of thrombin inhibitors. Said prodrugs have the general formula

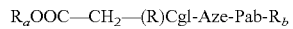

$R_a$OOC—CH$_2$—(R)Cgl-Aze-Pab-R$_b$ wherein $R_a$ represents H, benzyl or $C_{1-10}$ alkyl, $R_b$ (which replaces one of the hydrogen atoms in the amidino unit of Pab-H) represents OH, OC(O)R$_c$ or C(O)OR$_d$, R$_c$ represents $C_{1-7}$ alkyl, phenyl or 2-naphthyl and R$_d$ represents $C_{1-12}$ alkyl, phenyl, $C_{1-3}$ alkylphenyl, or 2-naphthyl. Preferred compounds include $R_a$OOC—CH$_2$—(R)Cgl-Aze-Pab-OH, wherein $R_a$ represents benzyl or $C_{1-10}$ alkyl, e.g. ethyl or isopropyl, especially EtOOC—CH$_2$—(R)Cgl-Aze-Pab-OH. The active thrombin inhibitors themselves are disclosed in WO 94/29336.

According to a further aspect of the invention there is thus provided a pharmaceutical formulation including a compound of the invention in admixture with a pharmaceutically acceptable adjuvant, diluent or carrier.

Suitable daily doses of the compounds of the invention in therapeutic treatment of humans are about 0.005 to 50.0 mg/kg body weight at oral administration and about 0.005 to 15.0 mg/kg body weight at parenteral administration. Preferable ranges of daily doses of the compounds of the invention in therapeutic treatment of humans are about 0.005 to 20.0 mg/kg body weight at oral administration and about 0.005 to 5.0 mg/kg body weight at parenteral administration.

The compounds of the invention have the advantage that they are effective against cardiac arrhythmias.

Compounds of the invention may also have the advantage that they may be more efficacious than, be less toxic than, have a broader range of activity (including exhibiting any combination of class I, class II, class III and/or class IV activity (especially class I and/or class IV activity in addition to class III activity)) than, be more potent than, be longer acting than, produce fewer side effects (including a lower incidence of proarrhythmias such as torsades de pointes) than, be more easily absorbed than, or that they may have other useful pharmacological properties over, compounds known in the prior art.

Biological Tests

Test A

Primary Electrophysiological Effects in Anaesthetised Guinea Pigs

Guinea pigs weighing between 500 and 1000 g were used. The animals were housed for at least one week before the experiment and had free access to food and tap water during that period.

Anaesthesia was induced by an intraperitoneal injection of pentobarbital (50 to 60 mg/kg) and catheters were introduced into one carotid artery (for blood pressure recording and blood sampling) and into one jugular vein (for drug infusions). Needle electrodes were placed on the limbs for recording of ECGs (lead II). A thermistor was placed in the rectum and the animal was placed on a heating pad, set to a rectal temperature of between 37.5 and 38.5° C.

A tracheotomy was performed and the animal was artificially ventilated with room air by use of a small animal ventilator, set to keep blood gases within the normal range for the species. In order to reduce autonomic influences both vagi were cut in the neck, and 0.5 mg/kg of propranolol was given intravenously, 15 minutes before the start of the experiment.

The left ventricular epicardium was exposed by a left-sided thoracotomy, and a custom-designed suction electrode for recording of the monophasic action potential (MAP) was applied to the left ventricular free wall. The electrode was kept in position as long as an acceptable signal could be recorded, otherwise it was moved to a new position. A bipolar electrode for pacing was clipped to the left atrium. Pacing (1 ms duration, twice the diastolic threshold) was performed with a custom-made constant current stimulator. The heart was paced at a frequency just above the spontaneous sinus rate during 30 s every fifth minute throughout the study.

The MAP signal, the blood pressure signal and the lead II ECG were collected (the sampling frequency was 1000 Hz and each sampling period 10 s) on a personal computer during the last 10 s of each 30 s pacing sequence and the last 10 s of the following min of sinus rhythm. The signals were processed using a custom-designed computer program (PharmLab v 4.0).

The test procedure consisted of two basal control recordings, 3 minutes apart, during both pacing and sinus rhythm. After the second control recording, the first dose of the test substance was infused in a volume of 0.2 mL/kg into the jugular vein catheter for 30 seconds. Three minutes later, pacing was started and a new recording was made. Five minutes after the previous dose, the next dose of test substance was administered. Six to ten consecutive doses were given during each experiment.

Data Analysis

Of the numerous variables measured in this analysis, three were selected as the most important for comparison and selection of active compounds. The three variables selected were the MAP duration at 75 percent repolarization during pacing, the atrio-ventricular (AV) conduction time (defined as the interval between the atrial pace pulse and the start of the ventricular MAP) during pacing, and the heart rate (defined as the RR interval during sinus rhythm). Systolic and diastolic blood pressure were measured in order to judge the haemodynamic status of the anaesthetised animal. Further, the ECG was checked for arrhythmias and/or morphological changes.

The mean of the two control recordings was set to zero and the effects recorded after consecutive doses of test substance were expressed as percentage changes from this value. By plotting these percentage values against the cumulative dose administered before each recording, it was possible to construct dose-response curves. In this way, each experiment generated three dose-response curves, one for MAP duration, one for AV-conduction time and one for the sinus frequency (RR interval). A mean curve of all experiments performed with a test substance was calculated, and potency values were derived from the mean curve. All dose-response curves in these experiments were constructed by linear connection of the data points obtained. The cumulative dose prolonging the MAP duration by 10% from the baseline was used as an index to assess the class III electrophysiological potency of the agent under investigation ($D_{10}$).

Test B

Rb$^+$-Efflux Assay for Detection of HERG Channel Blockers

The human ether-a-go-go related gene (HERG) encodes the voltage-gated K$^+$ channel underlying the cardiac rapid delayed rectifier current $I_{Kr}$. The IC50 value for HERG channel blockade was determined using a high throughput functional assay based on depolarisation-induced Rb$^+$-efflux from Chinese hamster ovary cells stably expressing the HERG-channel.

Cells were grown in Ham F12 (Life Technologies 31765-027) supplemented with 10% FBS and 0.6 mg/mL hygromycin B and were routinely passaged twice-weekly. For experimental studies, cells were plated at a density of 15,000 cells/well in Falcon, 384-well tissue culture-treated black-walled clear-bottomed plates and were thereafter incubated overnight at 37° C. in a cell culture incubator.

Following incubating overnight, cell plates were washed and a Rb$^+$-Load buffer (a physiological buffer containing Rb$^+$) was added. Cell plates were then incubated for 3 hours and were thereafter washed. Following this wash, the test compounds were added. The cell plates were then incubated for another 10 minutes and, following this incubation period, external K$^+$ concentration was increased in order to depolarize the cells and activate HERG channels. After a ten minute exposure period to the increased K$^+$ concentration, supernatants were transferred to new microplates for subsequent determination of Rb$^+$ content, using Atomic Absorption Spectrometry analysis.

The basal Rb$^+$ efflux (content of Rb$^+$ (mg/L) in supernatants of wells receiving only wash buffer) was defined as 100% inhibition and the stimulated Rb$^+$efflux (content of Rb$^+$ (mg/L) in supernatants of wells exposed only to increased external potassium concentration) was defined as 0% inhibition.

Compound activity was expressed as:

$$100 \times \left[1 - \frac{A-B}{C-B}\right]$$

A: Rb$^+$ content in wells receiving test compound+increased external K$^+$.
B: Basal Rb$^+$ efflux.
C: Stimulated Rb$^+$ efflux.

The invention is illustrated by way of the following examples.

EXAMPLES

General Experimental Procedures

Mass spectra were recorded on one of the following instruments: MUX(8)-LCT, ZQ Masspectrometer and Quattro micro, all from Waters Micromass.

LC-MS:

Separation was performed using Agilent 1100 Series Modules or Waters 1525 pump on a ACT (Advanced Chromatography Technologies) ACE C8 3×50 mm 3 μm with gradient elution.

Samples were injected using Waters 2700 Sample Manager.

Mobile phases:

Generic gradients were applied from 5% to 95% acetonitrile.

Buffers containing 10 mM ammonium acetate or 5 mM ammonium formate/5 mM formic acid were used.

The mass spectra were recorded with a Waters ZQ2000 or Waters ZMD equipped with an electrospray interface, switching positive and negative ionization mode. UV spectra were collected by a Agilent 1100 PDA or Waters 2996 DAD and the evaporative light scattering (ELS) signal by a Sedere Sedex 55 or 75.

Data collection and evaluation were performed using the MassLynx software.

$^1$H NMR and $^{13}$C NMR measurements were performed on a BRUKER ACP 300 and Varian 300, 400, 500 and 600 Mercury, Unity plus and Inova spectrometers, operating at $^1$H frequencies of 300, 400, 500 and 600 MHz respectively and at $^{13}$C frequencies of 75.4, 100.6, 125.7 and 150.9 MHz respectively.

Rotamers may or may not be denoted in spectra depending upon ease of interpretation of spectra. Unless otherwise stated, chemical shifts are given in ppm with the solvent as internal standard.

Synthesis of Intermediates

The following intermediates were not commercially available, and were therefore prepared by the methods described below.

Preparation A

Methanesulfonic acid 2-{[3-(4-cyanophenol)propyl]methanesulfonyl-amino}ethyl ester (i) 3-(4-Cyanophenyl)acrylic acid ethyl ester To a solution of 4-bromobenzonitrile (50 g, 0.275 mol) and ethyl acrylate (35.4 g, 0.412 mol) in dry DMF (250 mL), palladium acetate (0.61 g, 0.0027 mol), tris-o-tolylphosphine (3.34 g, 0.011 mol) and triethylamine (57.3 mL, 0.412 mol) were added and refluxed at 95-100° C. for 2 h under an argon atmosphere. The reaction was quenched by adding water (250 mL) and extracted with ether (3×250 mL). The combined extract was washed with 1.5 N HCl (250 mL), water and brine and dried over sodium sulfate (anhydrous). Solvent evaporation under reduced pressure and purification by column chromatography over neutral alumina, using ethyl acetate in petroleum ether as eluent, yielded 55 g (90%) of the sub-title compound as an off-white solid.

(ii) 3-(4-Cyanophenyl)propionic acid ethyl ester

Pd/C (5 g, 10%) was added to a solution of 3-(4-cyanophenyl)acrylic acid ethyl ester (50 g, 0.25 mol; see step (i) above) in dry ethyl acetate (500 mL) under a nitrogen atmosphere, followed by triethylamine (50.3 g, 0.5 mol) and formic acid (57.2 g, 1.24 mol). The mixture was refluxed overnight under a nitrogen atmosphere. After the completion of the reaction (monitored by TLC), the mixture was filtered and the filtrate then washed with water, 5% NaHCO$_3$ solution and brine, before being dried over sodium sulfate. Solvent evaporation under reduced pressure yielded 50 g (99%) of the sub-title compound as a pale yellow oil.

(iii) 4-(3-Hydroxypropyl)benzonitrile

To a solution of LiBH$_4$ (14 g, 0.65 mol) in dry ether (400 mL) was added 3-(4-cyanophenyl)propionic acid ethyl ester (50 g, 0.249 mol; see step (ii) above), followed by methanol (27 mL) dropwise. The reaction mixture was refluxed for 3 h. After completion (monitored by TLC), the reaction was quenched by adding cold, saturated ammonium chloride solution (100 mL), followed by water (300 mL). The layers were then separated. The aqueous layer was extracted with ether (2×100 mL) and the combined organic layers were washed with brine. After drying over anhydrous sodium sulfate, the organic layer was concentrated to give the crude product. This crude product was purified by column chromatography over silica gel, using ethyl acetate in petroleum ether as eluent. This yielded 16.5 g (42%) of the sub-title compound as a pale yellow liquid.

(iv) 4-(3-Bromopropyl)benzonitrile

To a solution of 4-(3-hydroxypropyl)benzonitrile (13 g, 0.081 mol; see step (iii) above) and triphenylphosphine (42.3 g, 0.16 mol) in DCM (150 mL) was added, dropwise at 0-5° C., a solution of CBr$_4$ (53.5 g, 0.16 mol) in DCM (100 mL). The resulting mixture was stirred at room temperature overnight. The reaction mixture was concentrated and the product was purified by column chromatography over silica gel, using petroleum ether in ethyl acetate as eluent, to yield 12.5 g (69%) of the sub-title compound as a yellow liquid.

(v) 4-[3-(2-Hydroxyethylamino)propyl]benzonitrile

To a solution 4-(3-bromopropyl)benzonitrile (8 g, 0.0357 mol; see step (iv) above) in dry acetonitrile (150 mL) were added anhydrous K$_2$CO$_3$ (7.4 g, 0.0535 mol) and ethanolamine (10.9 g, 0.179 mol). The resulting reaction mixture was then stirred overnight at room temperature, after which it was filtered and concentrated. The crude product thus obtained was purified by column chromatography over silica gel, using methanol in chloroform as eluent, to yield 4.2 g (57.5%) of the sub-title compound as a pale yellow solid.

(vi) Methanesulfonic acid 2-{[3-(4-cyanophenyl)propyl]methanesulfonyl-amino}ethyl ester To a solution of 4-[3-(2-hydroxyethylamino)propyl]benzonitrile (4 g, 0.0196 mol; see step (v) above) in dry DCM (80 mL) were added, at 0-5° C., triethylamine (5.9 g, 0.0588 mol) and mesyl chloride (5.6 g, 0.049 mol). The resulting mixture was then stirred at room temperature for 30 min, after which the reaction was quenched by addition of water (50 mL). The resulting aqueous layer was extracted with DCM (2×50 mL) and the combined organic layers were washed with brine. Solvent was removed under reduced pressure and the crude product was recrystallised from methanol to yield 4.2 g (62%) of the title compound as a white solid.

Preparation B

N-[3-(4-Cyanophenyl)propyl]-N-[2-(9-oxa-3,7-diazabicyclo[3.3.1]non-3-yl)ethyl]methanesulfonamide, hydrochloride salt

(i) 7-(2-{[3-(4-Cyanophenyl)propyl]methanesulfonylamino}ethyl)-9-oxa-3,7-diazabicyclo[3.3.1]nonane-3-carboxylic acid tert-butyl ester A mixture of 9-oxa-3,7-diaza-bicyclo[3.3.1]nonane-3-carboxylic acid tert-butyl ester (2.35 g, 0.01 mol; see WO 01/28992), methanesulfonic acid 2-{[3-(4-cyanophenyl)propyl]methanesulfonylamino}ethyl ester (3.7 g, 0.01 mol; see Preparation A above) and anhydrous K$_2$CO$_3$ (2.1 g, 0.015 mol) in dry acetonitrile (70 mL) was stirred under nitrogen atmosphere at 55-60° C. for 3 days. After filtration and concentration, the crude product was purified by column chromatography (silica gel: 60-120 mesh, eluent: petroleum ether-ethyl acetate, 50:50). Yield: 3.25 g (66%).

(ii) N-[3-(4-Cyanophenyl)propyl]-N-[2-(9-oxa-3,7-diazabicyclo[3.3.1]non-3-yl)ethyl]methanesulfonamide, hydrochloride salt 7-(2-{[3-(4-cyanophenyl)propyl]methanesulfonylamino}ethyl)-9-oxa-3,7-di-azabicyclo[3.3.1]nonane-3-carboxylic acid tert-butyl ester (3.8 g, 0.0095 mol; see step (i) above) was added to a saturated solution of HCl$_{(g)}$ in ethyl acetate (50 mL) and the resultant mixture was then stirred overnight. On completion of the reaction (as determined by TLC), ethyl acetate was decanted and the product was dried under high vacuum to give the title compound. Yield: 1.5 g (54%).

Preparation C

N-(2-Bromoethyl)-N-[2-(4-cyanophenoxy)ethyl]methanesulfonamide

(i) 4-(2-Bromoethoxy)benzonitrile

Anhydrous potassium carbonate (233 g, 1.68 mol) was added to a solution of 4-hydroxybezonitrile (100 g, 0.84 mol) in DMF (700 mL), and the resultant mixture was stirred for 1 h under a N$_2$ atmosphere. 1,2-Dibromo-ethane (362 mL, 4.2 mol) was added slowly to the reaction mixture, which was then stirred at 55-60° C. overnight. The reaction mixture was diluted with water and extracted with ethyl acetate (3×750 mL). The combined organic layer was washed with water and then concentrated. The crude product was purified by column chromatography (silica gel: 60-120 mesh, eluent: petroleum ether-ethyl acetate, 90:10). Yield: 60 g (32%).

(ii) 4-[2-(2-Hydroxyethylamino)ethoxy]benzonitrile 4-(2-Bromoethoxy)benzonitrile (30 g, 0.133 mol; see step (i) above) and ethanolamine (48 mL, 0.78 mol) were mixed and refluxed, under a nitrogen atmosphere, at about 120° C. for 3 h. The reaction was quenched by addition of a sodium hydroxide solution to the mixture. The sub-title compound was extracted using DCM (2×250 mL), which was dried over anhydrous sodium sulfate and then concentrated. Yield: 13.1 g (48%).

(iii) Methanesulfonic acid 2-{[2-(4-cyanophenoxy)ethyl]methanesulfonyl-amino}ethyl ester To a solution of 4-[2-(2-hydroxyethylamino)ethoxy]benzonitrile (14 g, 0.068 mol; see step (ii) above) in dry DCM (200 mL) was added triethylamine (28.4 mL, 0.2 mol), followed by methanesulfonyl chloride (13 mL, 0.17 mol) at 0-5° C. The reaction mixture was stirred at room temperature for 1 h. After completion of the reaction (by TLC), water (250 mL) was added and the organic layer was separated. The aqueous layer was extracted with DCM (2×100 mL) and the combined organic layers were washed with water. After concentration, the crude product was further purified by column chromatography (silica gel: 60-120 mesh, eluent: chloroform-methanol, 98.5:1.5). Yield: 18.2 g (74%).

(iv) N-(2-Bromoethyl)-N-[2-(4-cyanophenoxy)ethyl]methanesulfonamide

To a solution of methanesulfonic acid 2-{[2-(4-cyanophenoxy)ethyl]-methanesulfonylamino}ethyl ester (10 g, 0.028 mol; see step (iii) above) in dry acetone (100 mL), was added lithium bromide (4.8 g, 0.055 mol). The reaction mixture was added refluxed overnight under a nitrogen atmosphere, before being filtered and concentrated to give the title compound. Yield: 10 g (97%).

Preparation D

Toluene-4-sulfonic acid 2-{1-[2-(4-cyanophenoxy)ethyl]ureido}ethyl ester (i) N-[2-(4-Cyanophenoxy)ethyl]-N-(2-hydroxyethyl)urea To a solution of 4-[2-(2-hydroxyethylamino)ethoxy]benzonitrile (5 g, 0.0242 mol; see Preparation C(ii) above) in dioxane (65 mL) and water (65 mL) was added, at rt, potassium cyanate (4.92 g, 0.0606 mol), followed by acetic acid (4.36 g, 0.0726 mol). The reaction mixture was then stirred at rt overnight, before being concentrated under reduced pressure. The resulting residue was partitioned between water and dichloromethane. The organic layer was separated, washed with water and brine, dried over sodium sulfate and then concentrated. The crude product was further purified by column chromatography. Yield: 3.5 g.

(ii) Toluene-4-sulfonic acid 2-{1-[2-(4-cyanophenoxy)ethyl]ureido}ethyl ester

To a solution of intermediate 1-[2-(4-cyanophenoxy)ethyl]-1-(2-hydroxy-ethyl)urea (4.7 g, 0.0188 mol; see step (i) above) in dry THF (150 mL) was added n-butyllithium (18.89 mL, 1.1 M) at −78° C. The reaction mixture was stirred at −78° C. for 1 h, after which a solution of freshly crystallised p-toluenesulfonyl chloride (4.3 g, 0.023 mol) in THF (50 mL) was added dropwise. The reaction mixture was then stirred at −78° C. for a further 30 min, before being warmed to −30° C., and stirred for 2 h more. The reaction mixture was quenched with water and extracted with ethyl acetate. The organic layer was washed with brine, dried over $Na_2SO_4$, concentrated and the residue was recrystallised in ethyl acetate/hexane to yield the title compound as an off-white solid. Yield: 3.5 g.

Preparation E

N-[2-(4-Cyanophenoxy)ethyl]-N-[2-(9-oxa-3,7-diazabicyclo[3.3.1]non-3-yl)ethyl]urea (i) 7-(2-{1-[2-(4-Cyanophenoxy)ethyl]ureido}ethyl)-9-oxa-3,7-diazabicyclo-[3.3.1]nonane-3-carboxylic acid tert-butyl ester A mixture of toluene-4-sulfonic acid 2-{1-[2-(4-cyanophenoxy)ethyl]-ureido}ethyl ester (15 g, 0.0372 mol, 1.0 eq.; see Preparation D above), 9-oxa-3,7-diaza-bicyclo [3.3.1]nonane-3-carboxylic acid tert-butyl ester (8.525 g, 0.0372 mol, 1.0 eq.; see WO 01/28992), fused $K_2CO_3$ (7.7 g, 0.0558 mol, 1.5 eq.) and lithium bromide (9.6 g, 0.1116 mol, 3.0 eq.) in dry acetonitrile (350 mL) was heated to 40° C. under $N_2$ for 4 days. The reaction was cooled to rt, filtered and the filtrate was concentrated under reduced pressure. The resulting residue was purified by column chromatography over silica gel, using 3% methanol and DCM as eluent, to yield the sub-title compound as a white solid. Yield: 7 g, 40.9%.

(ii) N-[2-(4-Cyanophenoxy)ethyl]-N-[2-(9-oxa-3,7-diazabicyclo[3.3.1]non-3-yl)ethyl]urea 7-(2-{1-[2-(4-Cyanophenoxy)ethyl]ureido}ethyl)-9-oxa-3,7-diazabicyclo-[3.3.1]nonane-3-carboxylic acid tert-butyl ester (6.44 g; see step (i) above) was added to a solution of HCl-saturated, dry dioxane (300 mL) at 0° C. The reaction was then stirred at rt for 1 hr. The resulting precipitate was filtered under $N_2$, washed with dry ether and then dried under vacuum to provide the title compound. Yield: 6 g.

Preparation F

Toluene-4-sulfonic acid 2-{1-[3-(4-cyanophenyl)propyl]ureido}ethyl ester (i) 1-[3-(4-Cyanophenyl)propyl]-1-(2-hydroxyethyl)urea 4-[3-(2-Hydroxyethylamino)propyl]benzonitrile (6.7 g, 0.0328 mol; see Preparation A(v) above) and urea (2 g, 0.0328 mol) were mixed and heated at 130° C. for 2 h. The reaction mixture was cooled to room temperature and water was added. The resulting solid was filtered and dried to give 5.9 g (72%) of the sub-title compound as a white solid.

(ii) Toluene-4-sulfonic acid 2-{1-[3-(4-cyanophenyl)propyl]ureido}ethyl ester

1-[3-(4-Cyanophenyl)propyl]-1-(2-hydroxyethyl)urea (5.9 g, 0.0238 mol; see step (i) above) was taken in dry pyridine (20 mL). Freshly prepared p-toluenesulfonyl chloride (4.9 g, 0.02627 mol) was then added portion-wise at 0° C. The reaction mixture was stirred at 0° C. for 3 h, after which ethyl acetate was added (to remove pyridine from product) and the resulting solid was filtered. The product was then purified by column chromatography, using methanol in dichloromethane as the eluent, followed by crystallisation from isopropanol. This yielded 2.7 g (62%) of the title compound as a colourless, crystalline solid.

$^1$H NMR (300 MHz; $CD_3OD$) δ 7.76-7.70 (m, 4H), 7.45 (d, 2H), 7.27 (d, 2H), 4.75 (t, 2H), 3.95 (t, 2H), 3.52 (t, 2H), 2.83 (t, 2H), 2.41 (s, 3H), 2.0 (m, 2H);

$^{13}$C NMR (75.5 MHz, $CD_3OD$) δ 163.46, 148.78, 144.13, 142.18, 133.91, 131.06, 130.34, 127.41, 120.34, 111.47, 70.52, 48.65, 46.13, 34.05, 29.20, 21.81.

Preparation G

1-[2-(4-Cyanophenoxy)ethyl]-3,3-dimethyl-1-(2-oxoethyl)urea (i) 1-[2-(4-Cyanophenoxy)ethyl]-1-(2-hydroxyethyl)-3,3-dimethylurea 4-{2-[(2-Hydroxyethyl)amino]ethoxy}benzonitrile (5 g, 0.0242 mol; see Preparation C, step (ii) above) was taken in dry dichloromethane (50 mL) and cooled to 0° C. Triethylamine (4 mL, 0.03 mol), followed by N,N-dimethylcarbamoyl chloride (3.9 g, 0.03 mol), was added, and the reaction mixture was stirred at room temperature overnight. The reaction mixture was diluted with water and extracted with dichloromethane. The organic layer was washed with water and brine and dried over sodium sulfate. The solvent was evaporated under reduced pressure. Purification by column chromatography using dichloromethane in methanol yielded 6 g of the sub-title compound as pale yellow liquid.

(ii) 1-[2-(4-Cyanophenoxy)ethyl]-3,3-dimethyl-1-(2-oxoethyl)urea

Oxalyl chloride (6.3 g, 0.0497 mol) was added dropwise to a stirred solution of DMSO (7.6 g, 0.094 mol) and dichloromethane (100 mL) at −78° C. After stirring for 15 min at the same temperature, 1-[2-(4-cyanophenoxy)ethyl]-1-(2-hydroxyethyl)-3,3-dimethylurea (6 g, 0.0325 mol; see step (i) above) in dichloromethane was added and stirring continued for 3 h under a nitrogen atmosphere. Triethylamine (16.4 mL, 0.1625 mol) was added dropwise and the reaction mixture was then warmed slowly to −30° C. The reaction mixture was quenched with an aqueous solution of citric acid, and the resulting mixture extracted with dichloromethane. The organic layer was washed with water and brine and dried over sodium sulfate. Solvent evaporation under reduced pressure yielded 4.5 g of the crude title compound, which was used without further purification.

Preparation H

1-[2-(4-Cyanophenoxy)ethyl]-3,3-dimethyl-1-[2-(9-oxa-3,7-diaza-bicyclo[3.3.1]non-3-yl)ethyl]urea 7-(2-{1-[2-(4-Cyanophenoxy)ethyl]-3,3-dimethylureido}ethyl)-9-oxa-3,7-di-azabicyclo[3.3.1]nonane-3-carboxylic acid tert-butyl ester (6.5 g; see Example 5 below) was taken in HCl in dioxane (50 mL) and stirred for 30 min. The reaction mixture was decanted and the solid was taken in a biphasic mixture of dichloromethane and aqueous NaHCO₃. The organic layer was separated, washed with water, dried over sodium sulfate and concentrated. Purification by column chromatography yielded 1.3 g of the title compound as pale yellow solid.

Preparation I

Toluene-4-sulfonic acid 2-{1-[2-(4-cyanophenoxy)ethyl]-3-methylureido}-ethyl ester (i) 1-[2-(4-Cyanophenoxy)ethyl]-1-(2-hydroxyethyl)-3-methylurea 4-[2-(2-Hydroxyethylamino)ethoxy]benzonitrile (1 g, 0.009 mol; see Preparation C, step (ii) above) and N,N'-dimethylurea (0.43 g, 0.0049 mol) were heated with stirring at 130° C. for 4 h. The reaction was directly purified by column chromatography to yield 0.7 g of the sub-title product as an off white solid.

(ii) Toluene-4-sulfonic acid 2-{1-[2-(4-cyanophenoxy)ethyl]-3-methyl-ureido}ethyl ester To a well-stirred solution of 1-[2-(4-cyanophenoxy)ethyl]-1-(2-hydroxy-ethyl)-3-methylurea (6.6 g, 0.0257 mol; see step (i) above) in dry THF (70 mL) was added n-BuLi (2.85 N, 1.766 g, 0.0276 mol) at −78° C., dropwise under a nitrogen atmosphere. After stirring at the same temperature for 45 min, p-toluenesulfonyl chloride (5.25 g, 0.0276 mol) in dry THF was added (drop by drop) and the reaction mixture was then stirred at −40° C. for 2 h. The reaction was quenched with 50 mL water and warmed to room temperature. The product was extracted with ethyl acetate, washed with brine solution and dried over sodium sulfate. Solvent evaporation under reduced pressure, followed by column chromatography over silica gel (using 15-25% methanol in chloroform) yielded 1.36 g of the title compound as a brown gummy liquid.

Preparation J

1-[2-(4-Cyanophenoxy)ethyl]-3-methyl-1-[2-(9-oxa-3,7-diazabicyclo[3.3.1]-non-3-yl)ethyl]urea, hydrogen chloride salt 7-(2-{1-[2-(4-Cyanophenoxy)ethyl]-3-methylureido}ethyl)-9-oxa-3,7-diaza-bicyclo[3.3.1]nonane-3-carboxylic acid tert-butyl ester (920 mg; see Example 6 below) was dissolved in 10 mL of dry dioxane, to which was added 10 mL of dioxane saturated with HCl. The reaction mixture was stirred at room temperature for 1 h. The solid that formed was filtered, washed with dry diethyl ether and then dried under vacuum to yield 400 mg of the title compound as a yellow solid.

Preparation K

1-[3-(4-Cyanophenyl)propyl]-3,3-dimethyl-1-(2-oxoethyl)urea (i) 4-[3-(2-Hydroxyethylamino)propyl]benzonitrile 4-(3-Bromopropyl)benzonitrile (20 g, 0.089 mol) in acetonitrile was added to a vigorously stirred mixture of ethanolamine (27.2 g, 0.447 mol) and potassium carbonate (18.5 g, 0.133 mol) in 300 mL of dry acetonitrile. Stirring was then continued at room temperature overnight under a nitrogen atmosphere. The reaction mixture was filtered and concentrated under reduced pressure. The crude product thereby obtained was purified by column chromatography (using methanol in chloroform) to yield 15 g of the sub-title compound.

(ii) 1-[3-(4-Cyanophenyl)propyl]-1-(2-hydroxyethyl)-3,3-dimethylurea

N,N-Dimethylcarbamoyl chloride (3.9 g, 0.0368 mol) was added to a mixture of 4-[3-(2-hydroxyethylamino)propyl]benzonitrile (5 g, 0.025 mol; see step (i) above) and triethylamine (3.7 g, 0.368 mol) in dichloromethane (100 mL) at 0° C. Stirring was then continued at room temperature overnight. The reaction mixture was diluted with water and extracted with dichloromethane. The organic layer was washed with water and brine and dried over sodium sulfate. Solvent evaporation under reduced pressure, followed by purification by column chromatography (using 4% methanol in dichloromethane) yielded 7 g of the sub-title compound as a pale yellow, gummy liquid.

(iii) 1-[3-(4-Cyanophenyl)propyl]-3,3-dimethyl-1-(2-oxoethyl)urea

Oxalyl chloride (4.84 g, 0.038 mol) was added dropwise to a stirred solution of DMSO (5.9 g, 0.0763 mol) and dichloromethane (100 mL) at −78° C. After 15 min at the same temperature, 1-[3-(4-cyanophenyl)propyl]-1-(2-hydroxyethyl)-3,3-dimethylurea (7 g, 0.0254 mol) in dichloromethane was added and stirring continued for 3 h under a nitrogen atmosphere. Triethylamine (12.8 g, 0.127 mol) was added (dropwise), and the reaction mixture was then warmed slowly to −30° C. The reaction mixture was quenched with 10% citric acid (aq.) and extracted with dichloromethane. The organic layer was washed with water and brine, dried over sodium sulfate and concentrated to yield 6.5 g of the crude title compound, which was used without further purification.

Preparation L

1-[3-(4-Cyanophenyl)propyl]-3,3-dimethyl-1-[2-(9-oxa-3,7diazabicyclo-[3.3.1]non-3-yl)ethyl]urea, hydrogen chloride salt 7-(2-{1-[3-(4-Cyanophenyl)propyl]-3,3-dimethylureido}ethyl)-9-oxa-3,7-di-azabicyclo[3.3.1] nonane-3-carboxylic acid tert-butyl ester (7.5 g; see Example 7 below) was taken in dioxane (20 mL, saturated with HCl gas) and stirred for 2 h. The organic layer was decanted and the residue was washed with dry diethyl ether and dried under vacuum to yield 3 g the title compound as a pale yellow solid.

Preparation M

N-{2-[7-(4-Cyanobenzyl)-9-oxa-3,7-diazabicyclo [3.3.1]non-3-yl]ethyl}-methanesulfonamide (i) 7-(4-Cyanobenzyl)-9-oxa-3,7-diazabicyclo[3.3.1] nonane-3-carboxylic acid tert-butyl ester 4-Cyanobenzyl bromide (2 g, 0.01 mol), 9-oxa-3,7-diazabicyclo[3.3.1]nonane-3-carboxylic acid tert-butyl ester (2.33 g, 0.01 mol; see WO 01/28992) and potassium carbonate (3.52 g, 0.026 mol) were taken in dry acetonitrile (25 mL) and stirred at 60° C. overnight under a nitrogen atmosphere. The reaction mixture was cooled to rt, filtered and the filtrate concentrated under reduced pressure. The residue obtained thereby was purified by column chromatography (using 5% ethyl acetate in petroleum ether) to yield 2.6 g of the sub-title compound as a white solid.

(ii) 4-(9-Oxa-3,7-diazabicyclo[3.3.1]non-3-ylmethyl)benzonitrile, hydrogen chloride salt 7-(4-Cyanobenzyl)-9-oxa-3,7-diazabicyclo[3.3.1] nonane-3-carboxylic acid tert-butyl ester (2.2 g) was taken in dioxane (25 mL, saturated with HCl gas) and the reaction mixture stirred at room temperature for 3 h. The dioxane was decanted off the solid product, which was then washed with diethyl ether and dried under vacuum to yield 1.82 g of the sub-title compound as a white solid.

(iii) N-(2-Bromoethyl)methanesulfonamide

A suspension of 2-bromoethylamine hydrobromide salt (15 g, 0.0724 mol) in dichloromethane (220 mL) was treated with triethylamine (18.31 g, 0.181 mol) for 30 min. Into the resulting mixture was added, dropwise at 0° C., methanesulfonyl chloride (9.11 g, 0.0796 mol). The reaction mixture was then stirred at room temperature for 3 h before being quenched with water. The organic layer was washed with water and then brine before being dried over sodium sulfate. Solvent evaporation under reduced pressure followed by column chromatography over silica gel (using 2% ethyl acetate in petroleum ether as eluent) gave 4.5 g of the sub-title compound as a pale yellow oil.

(iv) N-{2-[7-(4-Cyanobenzyl)-9-oxa-3,7-diazabicyclo[3.3.1]non-3-yl]-ethyl}methanesulfonamide 4-(9-Oxa-3,7-diazabicyclo[3.3.1]non-3-ylmethyl)benzonitrile, hydrogen chloride salt (1 g, 3.1 mmol; see step (ii) above), N-(2-bromoethyl)methane-sulfonamide (0.75 g, 3.72 mmol; see step (iii) above) and potassium carbonate (1.07 g, 7.75 mmol) were taken in dry acetonitrile (20 mL) and stirred for 15 min at rt under a nitrogen atmosphere. The reaction mixture was concentrated under reduced pressure and the residue obtained thereby was partitioned between water and dichloromethane. The organic layer washed with water followed by brine and was then dried over sodium sulfate. Evaporation of the solvent followed by vacuum drying of the residue gave 0.9 g of the title compound as a brown solid.

Preparation N

N-Benzyl-N-[2-(9-oxa-3,7-diaza-bicyclo[3.3.1]non-3-yl)-ethyl]-methanesulfonamide hydrochloride (i) N-benzyl ethanolamine A mixture of benzyl bromide (15 g, 0.0872 mol) and ethanol amine (26.5 g, 0.436 mol) was stirred at 120° C. for 3 h. The reaction mixture was diluted with brine and extracted with dichloromethane. The organic layer was washed with water and brine and dried over sodium sulfate. Solvent evaporated under reduced pressure and the residue was purified by column chromatography over silica gel using 4% methanol in dichloromethane as eluent to give N-benzyl ethanolamine (12 g) as a liquid.

(ii) Methanesulfonic acid 2-(benzyl-methanesulfonyl-amino)-ethyl ester

Methanesulfonyl chloride (18.9 g, 0.1655 mol) was added dropwise at 0° C. to a solution of N-benzyl ethanolamine (10 g, 0.0662 mol, from step (i) above) and triethylamine (27.6 ml, 0.1987 mol) in dichloromethane (100 ml). The reaction mixture was stirred at RT for 3 h under nitrogen atmosphere and partitioned between water and dichloromethane. The organic layer was separated, washed with water and brine and dried over sodium sulfate. Thes solvent was evaporated under reduced pressure and the residue was purified by column chromatography over silica gel using 3% methanol in dichloromethane, as eluent to give the sub-title compound (12 g) as a solid.

(iii) 7-[2-(Benzyl-methanesulfonyl-amino)-ethyl]-9-oxa-3,7-diaza-bicyclo[3.3.1]nonane-3-carboxylic acid tert-butyl ester A suspension of methanesulfonic acid 2-(benzyl-methanesulfonyl-amino)-ethyl ester (4 g, 0.0130 mol; from step (ii) above), 9-oxa-3,7-diaza-bicyclo[3.3.1]nonane-3-carboxylic acid tert-butyl ester (3 g, 0.013 mol; see WO 01/28992)), dry $K_2CO_3$ (3.6 g, 0.026 mol) and lithium bromide (2.2 g, 0.026 mol) in dry acetonitrile (50 ml) was stirred at 60° C. overnight under $N_2$. The reaction mixture was filtered and filtrate was concentrated under reduced pressure. The residue was purified by column chromatography over silica gel using 4% methanol in dichloromethane as eluent to yield (5 g) of the sub-title compound as a solid.

(iv) N-Benzyl-N-[2-(9-oxa-3,7-diaza-bicyclo[3.3.1]non-3-yl)-ethyl]-methanesulfonamide hydrochloride 7-[2-(Benzyl-methanesulfonyl-amino)-ethyl]-9-oxa-3,7-diaza-bicyclo[3.3.1]nonane-3-carboxylic acid tert-butyl ester (5 g, 0.011 mol, from step (iii) above) was taken in 20 ml of dioxane (saturated with HCl gas) and stirred for 30 min at room temperature. The precipitated solid was filtered, washed with dry ether and dried under vacuum to yield (3 g) of the title compound as an off white solid.

Preparation O

Methanesulfonic acid 2-(methanesulfonyl-phenethyl-amino)-ethyl ester

(i) 2-Phenethylamino-ethanol

A mixture of ethanolamine (10 g, 0.162 mol) and 1-phenylethyl bromide (5 g, 0.027 mol) was stirred at 120° C. for 3 h. The reaction mixture was partitioned between water and dichloromethane. Organic layer was washed with water and brine, dried over sodium sulfate and concentrated. The residue was purified by column chromatography over silica gel using 3% methanol in dichloromethane to afford (2.5 g) of desired product as a solid.

(ii) Methanesulfonic acid 2-(methanesulfonyl-phenethyl-amino)-ethyl ester

Methanesulfonyl chloride (4.3 g, 0.037 mol) was added dropwise at 0° C. to a well stirred solution of 2-phenethylamino-ethanol (2.5 g, 0.015 mol, from step (i) above) and triethylamine (4.6 g, 0.045 mol) in dry dichloromethane (50 ml). The reaction mixture was stirred at room temperature for 3 h and quenched with water. The reaction mixture was extracted with dichloromethane. The organic layer was washed with water and brine, dried over sodium sulfate and concentrated. The residue was purified by column chromatography over silica gel using 3% methanol in dichloromethane as eluent to yield (3 g) of compound as a solid.

Preparation P

Methanesulfonic acid 2-[methanesulfonyl-(2-phenoxy-ethyl)-amino]-ethyl ester

(i) (2-Bromo-ethoxy)-benzene

A suspension of phenol (5 g, 0.053 mol), 1,2-dibromethane (60 g, 0.319 mol) and $K_2CO_3$ (22 g, 0.16 mol) in dry acetonitrile (100 ml) was stirred at 60° C. overnight under nitrogen atmosphere. The reaction mixture was filtered and the solvent concentrated under reduced pressure. The residue was purified by column chromatography over silica gel using 10% ethyl acetate in petroleum ether as eluent to yield (10 g) of the sub-title compound as a solid.

(ii) 2-(2-Phenoxy-ethylamino)-ethanol

A mixture of ethanolamine (18.2 g, 0.298 mol) and (2-Bromoethoxy)-benzene (10 g, 0.0497 mol, from step (i) above) was stirred at 120° C. for 3 h. The reaction mixture was partitioned between water and dichloromethane. Organic layer was washed with water and brine, dried over sodium sulfate and concentrated. Residue was purified by column chromatography over silica gel using 4% methanol in dichloromethane to afford (3.8 g) of the sub-title compound as a solid.

(iii) Methanesulfonic acid 2-[methanesulfonyl-(2-phenoxy-ethyl)-amino]-ethyl ester Methanesulfonyl chloride (5.5 g, 0.058 mol) was added dropwise by at 0° C. to a well stirred solution of 2-(2-phenoxy-ethylamino)-ethanol (3.5 g, 0.0193 mol, from step (ii) above) and triethylamine (5.85 g, 0.058 mol) in dry dichloromethane (50 ml). The reaction mixture was stirred at room temperature for 3 h and quenched with water. The compound was extracted with dichloromethane. The organic layer was washed with water and brine, dried over sodium sulfate and concentrated. The residue was purified by column chromatography over silica gel using 2% methanol in dichloromethane as eluent to yield (4 g) of the title compound as a yellow solid.

Preparation Q

Trifluoro-methanesulfonic acid 2-(benzyl-trifluoromethanesulfonyl-amino)-ethyl ester (i): Triflic anhydride (11.18 g, 6.5 ml, 39 mmol) dissolved in 90 ml of DCM was added drop by drop to a well stirred solution of N-benzyl ethanol amine (2 g, 13.2 mmol) and diisopropylethyl amine (5.1 g, 6.9 ml, 39.7 mmol) in dichloromethane (160 ml) at 0° C. and stirred at room temperature for 1 h under nitrogen atmosphere. The reaction mixture was quenched with water and extracted with dichloromethane. Organic layer was washed with water and dried under sodium sulfate. Solvent evaporation under reduced pressure afforded 500 mg of the title compound as a an oil Preparation R

Toluene-4-sulfonic acid 2-(1-benzyl-3-methyl-ureido)-ethyl ester

(i) 1-Benzyl-1-(2-hydroxy-ethyl)-3-methyl-urea

A mixture of N-benzyl ethanolamine (3 g, 0.0198 mol) and N,N'-dimethyl urea was stirred at 130° C. overnight. The reaction mixture was cooled to RT and the crude product was purified by column chromatography over silica gel using 3% methanol in dichloromethane as eluent to yield 3.5 g of the sub-title compound as a liquid.

(ii) Toluene-4-sulfonic acid 2-(1-benzyl-3-methyl-ureido)-ethyl ester nBuLi (2.8 N, 1.01 g, 0.0157 mol) was added at −78° C. to a solution of 1-benzyl-1-(2-hydroxy-ethyl)-3-methyl-urea (3 g, 0.0143 mol, from (i) above) in 30 ml of dry TBF and stirred at same temperature for 30 min under nitrogen atmosphere. P-Toluenesulfonyl chloride (3 g, 0.0157 mol) in 20 ml of dry THF was added dropwise at −78° C. and stirred for 3 h under nitrogen atmosphere. The reaction was quenched with methanol and solvent evaporated under reduced pressure. The crude was purified by column chromatography over silica gel using 12% methanol in dichloromethane as eluent to yield 2.5 g of the title compound as a solid.

Preparation S

Ethanesulfonic acid 2-(benzyl-ethanesulfonyl-amino)-ethyl ester

Ethanesulfonyl chloride (2.1 g, 16.6 mmol) was added dropwise at 0° C. to a well-stirred solution of N-benzyl ethanolamine (1 g, 6.6 mmol) and triethylamine (2.8 ml. 19 mmol) in dry dichloromethane (100 ml). The reaction mixture was stirred at room temperature for 1 h and quenched with water. The compound was extracted with dichloromethane, the organic layer was washed with water, brine and dried over sodium sulfate. Solvent evaporation under reduced pressure, followed by column chromatography over silica gel using 2% methanol in chloroform as eluent afforded (0.8 g) of the title compound as a liquid.

EXAMPLES

Example 1

N-[2-(7-Benzyl-9-oxa-3,7-diazabicyclo[3.3.1]non-3-yl)ethyl]-N-[2-(4-cyanophenoxy)ethyl]urea 3-Benzyl-9-oxa-3,7-diaza-bicyclo[3.3.1]nonane (0.18 g, 0.82 mmol; see WO 01/28992) and toluene-4-sulfonic acid 2-{1-[2-(4-cyanophenoxy)ethyl]-ureido}ethyl ester (0.50 g, 1.24 mmol; see Preparation D above) were mixed in dry acetonitrile (15 mL) and stirred at 60° C. overnight. DCM (10 mL) was added, together with 0.5 g of PS—NCO (polymer-supported isocyanate). The mixture was stirred for 2 h, then filtered and evaporated. The crude product was put on a SCX-II (cation exchanger)-plug, which plug was then eluted with DCM:MeOH ($NH_3$-saturated), 80:20. The product was further purified on a Horizon prep. column (40 g, A: DCM(1% MeOH), B: DCM/MeOH($NH_3$-sat.), 80:20. Gradient 0-30% B over 1080 mL). The product was then further purified by prep. HPLC and finally extracted with DCM/$Na_2CO_3$ (aq.) to give 193 mg (51.9%) of the title compound.
$^{13}C$ NMR (100.6 MHz, $CDCl_3$) δ 162.2, 161.5, 136.2, 134.3, 129.9, 128.6, 127.7, 119.3, 115.3, 104.4, 68.6, 67.9, 64.2, 61.4, 57.3, 56.1, 49.2, 48.7

Example 2

N-[2-(7-Benzyl-9-oxa-3,7-diazabicyclo[3.3.1]non-3-yl)ethyl]-N-[2-(4-cyanophenoxy)ethyl]methane-sulfonamide, tartaric acid salt Methanesulfonic acid 2-{[2-(4-cyanophenoxy)ethyl] methanesulfonyl-amino}ethyl ester (0.60 g, 1.65 mmol; see Preparation C(iii) above) and 3-benzyl-9-oxa-3,7-diaza-bicyclo[3.3.1]nonane (0.36 g, 1.65 mmol; see WO 01/28992) were mixed in acetonitrile (12 mL). The resulting solution was divided into 3 equal parts, which were put in microwave vessels. $K_2CO_3$ (0.11 g, 0.46 mmol) was added to each vessel and the reaction was run in the microwave reactor for 10 minutes at 160° C. The reaction mixtures were filtered, combined and then put on a 5 g SCX-plug. The plug was washed with DCM, acetonitrile and DCM:MeOH (80:20) until all (relatively) apolar material had been eluted. The product was then eluted with DCM:MeOH($NH_3$-satd.) 80:20. Analysis by $^1H$ NMR showed residual oxabispidine starting material, and so the product was dissolved in DCM (30 mL) and 300 mg of polymer-supported isocyanate was added. The resulting mixture was then stirred overnight. Filtration and evaporation gave 450 mg of the pure, free base product. This product was then dissolved in ethanol, to which was added 1 equivalent (148.6 mg) of tartaric acid. The resulting mixture was evaporated and dissolved in water. Freeze-drying overnight then gave 623 mg (59%) of the title compound as a colourless powder.
$^{13}C$ NMR (free base, 100.6 MHz, $CDCl_3$) δ 161.7, 137.7, 134.3, 129.3, 128.5, 127.3, 119.2, 115.3, 104.8, 68.6, 67.6, 63.8, 59.0, 56.6, 56.4, 47.0, 44.9, 39.3

Example 3

N-[2-(4-Cyanophenoxy)ethyl]-N-{2-[7-(4-fluorobenzyl)-9-oxa-3,7-diaza-bicyclo[3.3.1]non-3-yl] ethyl}methanesulfonamide (i) 7-(2-{[2-(4-Cyanophenoxy)ethyl] methanesulfonylamino}ethyl)-9-oxa-3,7-diazabicyclo[3.3.1]nonane-3-carboxylic acid tert-butyl ester To a suspension of N-(2-bromoethyl)-N-[2-(4-cyanophenoxy)ethyl]methane-sulfonamide (6 g, 0.019 mol; see Preparation C above) and anhydrous potassium carbonate (3.6 g, 0.026 mol) in dry acetonitrile (100 mL) was added 9-oxa-3,7-diaza-bicyclo[3.3.1]nonane-3-carboxylic acid tert-butyl ester (4.35 g, 0.019 mol; see WO 01/28992), and the resultant mixture was then stirred at 50-55° C. overnight. After completion of the reaction (as determined by TLC), the mixture was filtered and concentrated. The crude product was further purified by column chromatography (silica gel: 60-120 mesh, eluent: chloroform-methanol, 99:1). Yield: 4.2 g (46%).

(ii) N-[2-(4-Cyanophenoxy)ethyl]-N-[2-(9-oxa-3,7-diazabicyclo[3.3.1]non-3-yl)ethyl]methanesulfonamide To a saturated solution of $HCl_{(g)}$ in dioxane (100 mL) was added 7-(2-{[2-(4-cyanophenoxy)ethyl] methanesulfonylamino}ethyl)-9-oxa-3,7-diaza-bicyclo [3.3.1]nonane-3-carboxylic acid tert-butyl ester (3.5 g, 0.0070 mol; see step (i) above), after which the reaction was stirred for 1 h. On completion of the reaction (as determined by TLC), dioxane was decanted and product (semi-solid) dissolved in methanol (25 mL). After concentrating the methanol, dry ether (50 mL) was added and the solvent was again concentrated. This was repeated twice and finally the product was dried under high vacuum. Yield: 3.0 g (99%).

(iii) N-[2-(4-Cyanophenoxy)ethyl]-N-{2-[7-(4-fluorobenzyl)-9-oxa-3,7-di-azabicyclo[3.3.1]non-3-yl] ethyl}methanesulfonamide N-[2-(4-Cyanophenoxy)ethyl]-N-[2-(9-oxa-3,7-diazabicyclo[3.3.1]non-3-yl)ethyl]methanesulfonamide (0.079 g, 0.2 mmol; see step (ii) above) and 1-bromomethyl-4-fluorobenzene (0.040 g, 0.21 mmol) and $K_2CO_3$ (0.041 g, 0.3 mmol) were was mixed in a microwave vessel and then heated in the microwave reactor for 15 min at 160° C. The mixture was filtered and put on a SCX-II plug. The plug was washed with DCM, acetonitrile, DCM/MeOH (80:20), after which the product was eluted with DCM:MeOH($NH_3$-satd.), 80:20. The product was purified on a 9 g Horizon prep. chromatography column (A:DCM(1% MeOH), B:DCM/MeOH($NH_3$-satd.), 80:20. Gradient 0-25% B, 270 mL (9 mL fractions)), which gave 63 mg (62.7%) of the title compound.

$^{13}$C NMR (125.7 MHz, CDCl$_3$) δ 160.5, 159.1, 158.6, 131.8, 130.9, 128.1, 128.0, 116.6, 112.8, 112.7, 112.6, 102.3, 65.9, 65.0, 60.3, 56.3, 54.0, 53.7, 44.4, 42.6, 36.6

Example 4

N-[2-(4-Cyanophenoxy)ethyl]-N-{2-[7-(pyridin-3-ylmethyl)-9-oxa-3,7-di-azabicyclo[3.3.1]non-3-yl]ethyl}methanesulfonamide N-[2-(4-Cyanophenoxy)ethyl]-N-[2-(9-oxa-3,7-diazabicyclo[3.3.1]non-3-yl]ethyl]methanesulfonamide (79 mg, 0.2 mmol; see Example 3(ii) above) and pyridine-3-carbaldehyde (36 mg, 0.34 mmol) were dissolved in DCM (4 mL) and shaken for 1.5 h. Sodium triacetoxyborohydride (144 mg, 0.68 mmol) was added and the mixture was shaken overnight. The reaction was quenched with 1 M K$_2$CO$_3$ (2 mL) and was then phase-separated. The aqueous layer was washed with DCM (3×3 mL) and the organic layers were combined and evaporated. The residue was purified by chromatography on silica, which gave 66 mg (68%) of the title compound.

$^{13}$C NMR (125.7 MHz, CDCl$_3$) δ 161.7, 150.6, 148.7, 136.7, 134.4, 133.4, 123.5, 119.2, 115.35, 104.8, 68.5, 67.6, 60.9, 58.8, 58.5, 56.9, 56.6, 56.3, 47.1, 45.4, 39.1

Example 5

7-(2-{1-[2-(4-Cyanophenoxy)ethyl]-3,3-dimethylureido}ethyl)-9-oxa-3,7-di-azabicyclo[3.3.1]nonane-3-carboxylic acid tert-butyl ester 1-[2-(4-Cyanophenoxy)ethyl]-3,3-dimethyl-1-(2-oxoethyl)urea (4.5 g; see Preparation G above) was taken in dichloromethane (100 mL). 9-Oxa-3,7-diazabicyclo[3.3.1]nonane-3-carboxylic acid tert-butyl ester (2.9 g, 0.013 mol; see WO 01/28992), followed by glacial acetic acid (1.47 g, 0.0245 mol), was added, and reaction mixture was stirred for 1 h. NaBH$_3$CN (1.54 g, 0.024 mol) was added at 0° C., and stirring was continued overnight at room temperature. The reaction mixture was diluted with water and extracted with dichloromethane. The organic layer was washed with water and brine and then dried over sodium sulfate. Solvent evaporation, followed by purification by column chromatography, yielded the title compound (6.5 g).

$^1$H NMR (CDCl$_3$, 300 MHz), δ 7.59 (d, 2H), 6.95 (d, 2H), 4.14-4.08 (m, 4 H), 3.82-3.77(m, 2H), 3.58-3.49 (3 H, m), 3.30-3.27 (m, 4 H), 2.92-2.80 (m, 7 H), 2.6-2.3(m, 4H), 1.45 (s, 9H)

Example 6

7-(2-{1-[2-(4-Cyanophenoxy)ethyl]-3-methylureido}ethyl)-9-oxa-3,7-diaza-bicyclo[3.3.1]nonane-3-carboxylic acid tert-butyl ester A mixture of toluene-4-sulfonic acid 2-{1-[2-(4-cyanophenoxy)ethyl]-3-methylureido}ethyl ester (1.35 g, 3.233 mmol; see Preparation I above), 9-oxa-3,7-diazabicyclo[3.3.1]nonane-3-carboxylic acid tert-butyl ester (1.48 g, 6.466 mmol; see WO 01/28992) and potassium carbonate (1.34 g, 9.7 mmol) in dry acetonitrile (15 mL) was stirred at 45° C. for 24 h. The reaction mixture was diluted with 20 mL water and extracted with ethyl acetate. The organic layer was washed with water, brine and dried over sodium sulfate. Solvent evaporation under reduced pressure followed by column chromatography over silica gel (using 2-2.5% methanol in dichloromethane) and further purification by preparative HPLC yielded 920 mg of the title compound as a white solid.

MS: 474 (M$^+$+H): calculated for C$_{24}$H$_{35}$N$_5$O$_5$ (M$^+$+H) 474.

Example 7

7-(2-{1-[3-(4-Cyanophenyl)propyl]-3,3-dimethylureidolethyl)-9-oxa-3,7-di-azabicyclo[3.3.1]nonane-3-carboxylic acid tert-butyl ester 1-[3-(4-Cyanophenyl)propyl]-3,3-dimethyl-1-(2-oxoethyl)urea (6.5 g; see Preparation K above) was taken in dichloromethane (100 mL), to which was added 9-oxa-3,7-diaza-bicyclo[3.3.1]nonane-3-carboxylic acid tert-butyl ester (4.36 g, 0.019 mol; see WO 01/28992), followed by glacial acetic acid (2.14 g, 0.0357 mol). The reaction mixture was stirred for 1 h before NaBH$_3$CN (2.24 g, 0.0357 mol) was added at 0° C. Stirring was continued overnight at room temperature. The reaction mixture was quenched with water and extracted with dichloromethane. The organic layer was washed with water and brine and dried over sodium sulfate. Solvent evaporation, followed by purification by column chromatography over silica gel (using 2% methanol in dichloromethane) yielded 7.5 g of the title compound as a yellow, gummy liquid.

$^1$H NMR (CDCl$_3$, 300 MHz); δ 7.57 (d, 2H), 7.28 (d, 2H), 4.09-3.9 (m, 2H), 3.80-3.74 (m, 2 H), 3.23-3.1 (m, 6 H), 2.88-2.78 (m, 4 H), 2.75 (s, 6H), 2.63 (t, 2H), 2.52 (t, 2H), 2.3-2.1 (m, 2 H), 1.83 (t, 2H), 1.44 S, 9 H)

Example 8

N-Benzyl-N-{2-[7-(4-cyanobenzyl)-9-oxa-3,7-diazabicyclo[3.3.1]non-3-yl]-ethyl}methanesulfonamide To a suspension of NaH (60% in oil, 0.039 g, 1.64 mmol) in dry DMF (10 mL) was added N-{2-[7-(4-cyanobenzyl)-9-oxa-3,7-diazabicyclo[3.3.1]-non-3-yl]ethyl}methanesulfonamide (0.3 g, 0.82 mmol; see Preparation M above) at 0° C. The reaction mixture was stirred for 1 h at room temperature. Benzyl bromide (0.155 g, 0.9 mmol) was added at 0° C. and the reaction mixture stirred at rt for 2 h. The reaction quenched with water, extracted with dichloromethane, washed with water, brine and then dried over sodium sulfate. Solvent evaporation under reduced pressure, followed by column chromatography of the residue over silica gel (using 5% methanol in chloroform as eluent) gave 160 mg of the title compound as a pale yellow solid.

$^{13}$C NMR (75 MHz, CDCl$_3$): δ 143.76, 136.07, 132.059, 129.30, 128.74, 128.14, 128.04, 118.83, 110.74, 68.17, 62.60, 57.70, 56.24, 55.94, 53.32, 51.38, 43.89, 39.18.

Example 9

N-(2-{7-[3-(4-Cyano-phenoxy)-propyl]-9-oxa-3,7-diaza-bicyclo[3.3.1]non-3-yl}-ethyl)-N-(2-phenoxyethyl)-methanesulfonamide (i) A suspension of 4-[3-(9-oxa-3,7-diaza-bicyclo[3.3.1]non-3-yl)-propoxy]-benzonitrile (1.5 g, 5.5 mmol, see WO 01/28992), methanesulfonic acid 2-[methanesulfonyl-(2-phenoxy-ethyl)-amino]-ethyl ester (1.51 g, 4.5 mmol, preparation P above) and dry K$_2$CO$_3$ (1.69 g, 12.3 mmol) in dry acetonitrile (100 ml) was stirred at 60° C. overnight under nitrogen atmosphere. The reaction mixture was filtered and solvent concentrated under reduced pressure. The residue was purified by column chromatography over silica gel using 3% methanol in dichloromethane as eluent to give the title compound (1.4 g) as a liquid.

$^1$H NMR (400 MHz, CD$_3$Cl$_3$) δ 7.57(2 H, d), 7.30 (2 H, d), 7.03-6.89 (5 H, m), 4.22-4.12 (8 H, m), 4.03-4.00 (3 H, bt), 3.79-3.71 (4 H, m), 3.37 (2 H, m), 3.12 (2 H, m), 3.00 (3 H, s) 2.85 (2 H, m), 2.83-2.76 (2 H, m), 2.50 (2 H, bs)

Example 10

N-Benzyl-N-{2-[7-(4-cyano-benzyl)-9-oxa-3,7-diaza-bicyclo[3.3.1]non-3-yl]-ethyl}-benzene-sulfonamide (i) Benzenesulfonic acid 2-(benzenesulfonyl-benzyl-amino)-ethyl ester Benzenesulfonyl chloride (2.2 ml, 0.0175 mol) was added dropwise at 0° C. to a well-stirred solution of N-benzyl ethanolamine (1 g, 0.7 mmol) and triethylamine (2.4 ml. 0.0175 mol) in dry dichloromethane (10 ml). The reaction mixture was stirred at room temperature for 1 h and quenched with water. The compound was extracted with dichloromethane, organic layer was washed with water, brine and dried over sodium sulfate. Solvent evaporation under reduced pressure afforded 0.6 g of the desired product as a solid. This was directly taken for next step without further purification.

(ii) N-Benzyl-N-{2-[7-(4-cyano-benzyl)-9-oxa-3,7-diaza-bicyclo[3.3.1]non-3-yl]-ethyl}-benzene-sulfonamide A suspension of benzenesulfonic acid 2-(benzenesulfo-nyl-benzyl-amino)-ethyl ester (0.33 g, 1.04 mmol, from step (i) above), 4-(9-Oxa-3,7-diazabicyclo[3.3.1]non-3-ylm-ethyl)benzonitrile, hydrogen chloride salt (0.5 g, 1.16 mmol, from prep M (ii) above) and potassium carbonate (0.64 g, 4.64 mmol) in dry acetonitrile (10 ml) was stirred at 60° C. overnight under nitrogen atmosphere. The reaction mixture was filtered and the filtrate was concentrated under reduced pressure. The residue was purified by column chromatography over silica gel using 10% methanol in dichloromethane as eluent to yield 80 mg of the title compound as a liquid.

$^1$H NMR (400 MHz, CDCl$_3$) δ 7.67-7.63(1 H, m), 7.58-7.50 (6 H, m), 7.30-7.27 (5 H, m), 4.45(2 H, s), 3.85 (2 H, bt), 3.72-3.64 (2 H, bm), 3.37 (2 H, m), 3.0-2.89 (4 H, bm), 2.75-2.16 (6H, bm)

Example 11

N-{2-[7-(2-Cyano-benzyl)-9-oxa-3,7-diaza-bicyclo[3.3.1]non-3-yl]-ethyl}-N-[2-(4-cyano-phenoxy)-ethyl]-methanesulfonamide To N-[2-(4-cyano-phenoxy)-ethyl]-N-[2-(9-oxa-3,7-diaza-bicyclo[3.3.1]-non-3-yl)-ethyl]-methanesulfonamide (0.079 g, 0.20 mmol), 2-bromo-methyl-benzonitrile (0.041 g, 0.21 mmol) and anhydrous potassium carbonate (0.042 g, 0.30 mmol) was added dry acetonitrile (4 mL). The mixture was heated by microwave irradiation (15 minutes, 160° C.) and was then filtered. The filtrate was loaded onto a cation exchange column (SCX-2, Isolute™, 2 g). The column was washed with dichloromethane, acetonitrile and dichloromethane/methanol 80:20 before eluting the crude product with 20% methanol saturated with ammonia in dichloromethane. The filtrate was concentrated in vacuo and the crude product was purified by chromatography on silica gel using methanol saturated with ammonia in dichloromethane as eluent, which afforded 57 mg (55.9%) of the title compound.

$^{13}$C NMR (125.7 MHz, CDCl$_3$) δ 159.06, 139.57, 131.78, 130.64, 130.24, 127.71, 125.27, 116.56, 115.58, 112.75, 110.56, 102.33, 65.84, 64.92, 58.67, 55.85, 53.80, 53.58, 44.66, 43.17, 36.36

Example 12

N-(4-Cyano-benzyl)-N-{2-[7-(4-cyano-benzyl)-9-oxa-3,7-diaza-bicyclo[3.3.1]non-3-yl]-ethyl}-meth-anesulfonamide To a suspension of sodium hydride (0.013 g of a 60% suspension in mineral oil, washed with pentane) in anhydrous N,N-dimethylformamide (4 mL) was added N-{2-[7-(4-Cyano-benzyl)-9-oxa-3,7-diaza-bicyclo[3.3.1]non-3-yl]-ethyl}-methanesulfonamide (0.109 g, 0.30 mmol) at 0° C. The mixture was stirred for 2 hours while the temperature was allowed to warm to room temperature. At 0° C., 4-bromomethyl-benzonitrile (0.065 g, 0.33 mmol) was added. The mixture was stirred for 2 hours at room temperature, whereupon water (5 mL) was added. The aqueous layer was extracted with dichloromethane (3×5 mL) and the combined organic layers were dried over Na$_2$SO$_4$ and concentrated in vacuo. The crude product was purified by chromatography on silica gel using methanol saturated with ammonia dichloromethane as eluent, which afforded 79 mg (54.9%) of the title compound.

$^{13}$C NMR (125.7 MHz, CDCl$_3$) δ 143.69, 142.72, 132.69, 132.46, 129.68, 128.63, 119.13, 118.74, 112.01, 111.11, 68.40, 63.27, 57.99, 56.38, 51.57, 44.95, 39.06

Example 13

N-benzyl-N-{2-[7-(4-cyanobenzyl)-9-oxa-3,7-diaz-abicyclo[3.3.1]non-3-yl]ethyl}-N',N'-dimethylurea (i) 1-Benzyl-1-(2-hydroxy-ethyl)-3,3-dimethyl-urea N,N-dimethyl carbamoyl chloride (2.55 g, 0.0238 mol) was added drop by drop at 0° C. to a solution of N-benzyl ethanol amine (3 g, 0.0198 mol) and triethylamine (3 g, 0.0298 mol) in 25 ml of DCM (dry) and stirred at RT for 3 h under nitrogen atmosphere. The reaction was quenched with water, extracted with dichloromethane, washed with water, brine and dried over sodium sulfate. Solvent evaporation under reduced pressure followed by column chromatography over silica gel using 3.5% methanol in dichloromethane as eluent afforded 4 g of the sub-title compound as a liquid.

(ii) N-benzyl-N-{2-[7-(4-cyanobenzyl)-9-oxa-3,7-diazabicyclo[3.3.1]non-3-yl]ethyl}-N',N'-dimethy-lurea Oxalyl chloride (1.14 g, 9 mmol) was added at −78° C. to a solution of DMSO (1.05 g, 13.5 mmol) in dry dichloromethane (10 ml) and stirred for 30 min. 1-Benzyl-1-(2-hydroxy-ethyl)-3,3-dimethyl-urea (1.05 g, 13.5 mmol; from step (i) above) in dry dichloromethane (10 ml). (1 g, 4.5 mmol) was added dropwise at same temperature and stirring continued for 3 h at the same temperature. Triethylamine (1.8 ml, 12.9 mmol) was added at −78° C. and the reaction mixture was warmed to −30° C. Reaction mixture was quenched with 10% aq. citric acid (10 ml) and extracted with dichloromethane. The organic layer was washed with brine and dried over sodium sulfate. Solvent evaporation under reduced pressure yielded 0.79 g of crude aldehyde as a liquid.

This (0.75 g, 3.4 mmol) was then taken in DCM (25 ml), 4-(9-Oxa-3,7-di-azabicyclo[3.3.1]non-3-ylmethyl)benzonitrile (960 mg, 3.4 mmol) was added at 0° C. The reaction mixture was stirred at RT overnight, quenched with water and extracted with dichloromethane. Organic layer was washed with water and brine and dried over sodium sulfate. Solvent evaporation under reduced pressure followed by purification by column chromatography over silica gel using 6.5% methanol in dichloromethane as eluent yielded 0.5 g of the desired product. This was further purified by prep HPLC to give 0.3 g of the title compound as off white solid.
API-MS: (M+1)=448

Example 14

N-benzyl-N-{2-[7-(4-cyanobenzyl)-9-oxa-3,7-diazabicyclo[3.3.1]non-3-yl]ethyl}acetamide (i) N-Benzyl-N-(2-hydroxy-ethyl)-acetamide Acetyl chloride (0.858 g, 10.8 mmol) was added drop by drop to a solution of N-benzyl ethanol amine (1.5 g, 9.9 mmol) and triethylamine (1.5 g, 14.9 mmol) in dry dichloromethane (20 ml) at 0° C. under nitrogen atmosphere and stirred at room temperature overnight. The reaction was quenched with water and extracted with dichloromethane. The organic layer was washed with water, 10% aq. $NaHCO_3$, brine and dried over sodium sulfate. Solvent evaporation under reduced pressure, followed by column chromatography over silica gel using 5% methanol in dichloromethane as eluent afforded 0.68 g of the desired product as an oil.

(ii) N-benzyl-N-{2-[7-(4-cyanobenzyl)-9-oxa-3,7-diazabicyclo[3.3.1]non-3-yl]ethyl}acetamide Oxalyl chloride (0.57 g, 4.5 mmol) was added at −78° C. to a solution of DMSO (0.63 ml, 9 mmol) in dry dichloromethane (5 ml) and stirred for 15 min. N-Benzyl-N-(2-hydroxy-ethyl)-acetamide (0.58 g, 3 mmol; from step (i) above) dissolved in dry dichloromethane (5 ml) was added dropwise at the same temperature and stirring continued for 3 h at the same temperature. Triethylamine (2.1 ml, 15 mmol) was added at −78° C. and the reaction mixture was warmed to −30° C. Reaction mixture was quenched with 10% aq. citric acid (10 ml) and extracted with dichloromethane. The organic layer was washed with brine and dried over sodium sulfate. Solvent evaporation under reduced pressure yielded 0.51 g of crude aldehyde. This (0.51 g, 2.6 mmol) was then taken in DCM (10 ml), 4-(9-Oxa-3,7-diazabi-cyclo[3.3.1]non-3-ylmethyl)benzonitrile, hydrogen chloride salt (0.57 g, 2.6 mmol; from step M (ii) above) and molecular sieves (500 mg) and stirred for 1 h at room temperature. $NaBH_3CN$ (0.24 g, 3.9 mmol) was added at 0° C. and stirring continued overnight under nitrogen atmosphere. The reaction was quenched with water and extracted with dichloromethane. The organic layer was washed with water and brine and dried over sodium sulfate. Solvent evaporation under reduced pressure followed by purification by column chromatography (two times) over silica gel using 3% methanol in dichloromethane as eluent yielded 430 mg desired product. This (430 mg) was again purified by prep HPLC using 1% acetic acid in acetonitrile as eluent. Acetonitrile was then evaporated under reduced pressure and the residue was partitioned between 10% $NaHCO_3$ and DCM. Organic layer was then washed with water and brine and dried over sodium sulfate. Solvent evaporation under reduced pressure afforded (150 mg) of the title compound as a liquid.
API-MS: (M+1)=419

Example 15

N-benzyl-N-{2-[7-(4-cyanobenzyl)-9-oxa-3,7-diazabicyclo[3.3.1]non-3-yl]ethyl}propane-2-sulfonamide (i) Benzyl-(2-hydroxy-ethyl)-carbamic acid tert-butyl ester $(Boc)_2O$ (7.9 g, 0.036 mol) was added drop by drop at 0° C. to a solution of N-benzyl ethanol amine (5 g, 0.033 mol) in dry dichloro methane (50 ml) and stirred at room temperature overnight under nitrogen atmosphere. The reaction was quenched with water, extracted with dichloromethane, washed with brine and dried over sodium sulfate. Solvent evaporation under reduced pressure followed by purification over silica gel using 10% ethyl acetate in petroleum ether as eluent afforded the sub-title compound (3.2 g) as an oil.

(ii) Benzyl-{2-[7-(4-cyano-benzyl)-9-oxa-3,7-diazabicyclo[3.3.1]non-3-yl]-ethyl}-carbamic acid tert-butyl ester Dry DMSO (1.8 g, 0.0237 mol) was added to a solution of oxalyl chloride (1.5 g, 0.01185 mol) in dry dichloro methane (25 ml) at −78° C. and stirred for 10 min. Benzyl-(2-hydroxy-ethyl)-carbamic acid tert-butyl ester (2 g, 0.0079 mol; from (i) above) in 15 ml of DCM was added dropwise at the same temperature and stirring continued at same temperature for 3 h. Triethylamine (5.5 ml) was added, the reaction mixture was warmed to −30° C. and quenched with 10% aq. citric acid. The compound was extracted with dichloromethane, washed with water and brine and dried over sodium sulfate. Solvent evaporation under reduced pressure afforded the desired aldehyde (2.5 g) as an liquid. This (2.5 g, 10 mmol) was then added to a mixture of 4-(9-oxa-3,7-diazabicyclo[3.3.1]non-3-ylmethyl)benzonitrile, hydrogen chloride salt (1.98 g, 8 mmol, from. M(i) above) and $MgSO_4$ (2 g) in dry dichloromethane (10 ml) and stirred for 4 h under nitrogen atmosphere. Methanol (10 ml), followed by $NaBH_3CN$ (0.76 g, 12 mmol) was added and the reaction mixture was stirred overnight. The reaction was quenched with water, extracted with dichloromethane, washed with brine and dried over sodium sulfate. Solvent evaporation under reduced pressure followed by purification over silica gel using 3% methanol in chloroform as eluent afforded the desired product (1.1 g) as an off white solid.

(iii) 4-[7-(2-Benzylamino-ethyl)-9-oxa-3,7-diazabicyclo[3.3.1]non-3-ylmethyl]-benzonitrile Dioxane saturated with HCl gas (10 ml) was added to a solution of benzyl-{2-[7-(4-cyano-benzyl)-9-oxa-3,7-diazabicyclo[3.3.1 ]non-3-yl]-ethyl}-carbamic acid tert-butyl ester (0.65 g, from step (ii) above in 5 ml of dioxane and stirred for 1 h at RT under nitrogen atmosphere. The reaction mixture was diluted with dry diethylether, and the solvent was decanted. Precipitated solid was washed with dry diethylether (4 times) and dried under vacuum to give HCl salt of the sub-title compound (0.5 g) as a powder.

(iv) N-benzyl-N-{2-[7-(4-cyanobenzyl)-9-oxa-3,7-diazabicyclo[3.3.1]non-3-yl]ethyl}propane-2-sulfonamide 4-[7-(2-Benzylamino-ethyl)-9-oxa-3,7-diaza-bicyclo[3.3.1]non-3-ylmethyl]-benzonitrile (0.5 g, 1.33 mmol, from step (iii) above) was taken in 30 ml of DCM/10% aq. NaHCO$_3$ (1:1) and stirred for 15 min. Isopropane sulfonyl chloride (0.28 g, 1.99 mmol) was added and stirring continued at RT for 1.5 h. The organic layer was separated, washed with brine and dried over sodium sulfate. Solvent evaporation under reduced pressure followed by purification over silica gel using 10% ethyl acetate in petroleum ether as eluent afforded the desired product (280 mg) as white solid. This was further purified by prep HPLC (0.1% TFA in acetonitrile), evaporated under reduced pressure, and the residue was partitioned between sat NaHCO$_3$ and DCM. The organic layer was washed with brine and dried over sodium sulfate. Solvent evaporation under reduced pressure afforded the title compound (140 mg) as an off-white solid.
API-MS: (M+1)=483

Example 16

The following compounds were prepared, from appropriate intermediates (such as those described hereinbefore), according to or by analogy with methods described herein:
(i) tert-butyl [2-(7-{2-[[2-(4-cyanophenoxy)ethyl](methylsulfonyl)-amino]ethyl}-9-oxa-3,7-diazabicyclo[3.3.1]non-3-yl)ethyl]-carbamate;
(ii) tert-butyl {2-[7-(2-{(aminocarbonyl)[2-(4-cyanophenoxy)ethyl]-amino}ethyl)-9-oxa-3,7-diazabicyclo[3.3.1]non-3-yl]ethyl}-carbamate;
(iii) N-[2-(4-cyanophenoxy)ethyl]-N-(2-{7-[2-(4-methoxyphenyl)-2-oxoethyl]-9-oxa-3,7-diazabicyclo[3.3.1]non-3-yl}ethyl)-methanesulfonamide;
(iv) N-[2-(4-cyanophenoxy)ethyl]-N-(2-{7-[2-(4-methoxyphenyl)-2-oxoethyl]-9-oxa-3,7-diazabicyclo[3.3.1]non-3-yl}ethyl)urea;
(v) 2-[7-(2-{(aminocarbonyl)[2-(4-cyanophenoxy)ethyl]amino}ethyl)-9-oxa-3,7-diazabicyclo[3.3.1]non-3-yl]-N-(tert-butyl)acetamide;
(vi) 2-[7-(2-{(aminocarbonyl)[2-(4-cyanophenoxy)ethyl]amino}ethyl)-9-oxa-3,7-diazabicyclo[3.3.1]non-3-yl]-N-benzylacetamide;
(vii) 2-[7-(2-{(aminocarbonyl)[2-(4-cyanophenoxy)ethyl]amino}ethyl)-9-oxa-3,7-diazabicyclo[3.3.1]non-3-yl]-N-(1-methyl-1-phenylethyl)acetamide;
(viii) N-(tert-butyl)-2-(7-{2-[[2-(4-cyanophenoxy)ethyl](methylsulfonyl)-amino]ethyl}-9-oxa-3,7-diazabicyclo[3.3.1]non-3-yl)acetamide;
(ix) N-benzyl-2-(7-{2-[[2-(4-cyanophenoxy)ethyl](methylsulfonyl)-amino]ethyl}-9-oxa-3,7-diazabicyclo[3.3.1]non-3-yl)acetamide;
(x) 2-(7-{2-[[2-(4-cyanophenoxy)ethyl](methylsulfonyl)amino]ethyl}-9-oxa-3,7-diazabicyclo[3.3.1]non-3-yl)-N-(1-methyl-1-phenyl-ethyl)acetamide;
(xi) tert-butyl [2-(7-{2-[[3-(4-cyanophenyl)propyl](methylsulfonyl)-amino]ethyl}-9-oxa-3,7-diazabicyclo[3.3.1]non-3-yl)ethyl]-carbamate;
(xii) N-(tert-butyl)-2-(7-{2-[[3-(4-cyanophenyl)propyl](methylsulfonyl)-amino]ethyl}-9-oxa-3,7-diazabicyclo[3.3.1]non-3-yl)acetamide;
(xiii) N-[2-(7-benzyl-9-oxa-3,7-diazabicyclo[3.3.1]non-3-yl)ethyl]-N-[3-(4-cyanophenyl)propyl]methanesulfonamide;
(xiv) N-[2-(4-cyanophenoxy)ethyl]-N-(2-{7-[2-(2,6-dimethylphenoxy)-ethyl]-9-oxa-3,7-diazabicyclo[3.3.1]non-3-yl}ethyl)urea;
(xv) N-[2-(4-cyanophenoxy)ethyl]-N-(2-{7-[2-(4-cyanophenyl)ethyl]-9-oxa-3,7-diazabicyclo[3.3.1]non-3-yl}ethyl)urea;
(xvi) N-[2-(4-cyanophenoxy)ethyl]-N-(2-{7-[2-(4-methoxyphenyl)ethyl]-9-oxa-3,7-diazabicyclo[3.3.1]non-3-yl}ethyl)urea;
(xvii) N-(2-{7-[2-(4-acetylphenyl)ethyl]-9-oxa-3,7-diazabicyclo-[3.3.1]non-3-yl}ethyl)-N-[2-(4-cyanophenoxy)ethyl]urea;
(xviii) N-[2-(4-cyanophenoxy)ethyl]-N-{2-[7-(2-phenylethyl)-9-oxa-3,7-diazabicyclo[3.3.1]non-3-yl]ethyl}urea;
(xix) N-[2-(4-cyanophenoxy)ethyl]-N-(2-{7-[2-(3-fluorophenyl)ethyl]-9-oxa-3,7-diazabicyclo[3.3.1]non-3-yl}ethyl)urea;
(xx) N-(2-{7-[(2-chloropyridin-3-yl)methyl]-9-oxa-3,7-diazabicyclo-[3.3.1]non-3-yl}ethyl)-N-[2-(4-cyanophenoxy)ethyl]methane-sulfonamide;
(xxi) N-[2-(4-cyanophenoxy)ethyl]-N-(2-{7-[(6-methoxypyridin-3-yl)methyl]-9-oxa-3,7-diazabicyclo[3.3.1]non-3-yl}ethyl)-methanesulfonamide;
(xxii) N-[2-(4-cyanophenoxy)ethyl]-N-(2-{7-[(4,5-dimethyl-2-furyl)-methyl]-9-oxa-3,7-diazabicyclo[3.3.1]non-3-yl}ethyl)-methanesulfonamide;
(xxiii) N-[2-(4-cyanophenoxy)ethyl]-N-(2-{7-[4-(trifluoromethyl)benzyl]-9-oxa-3,7-diazabicyclo[3.3.1]non-3-yl}ethyl)methanesulfonamide;
(xxiv) N-{2-[7-(4-chlorobenzyl)-9-oxa-3,7-diazabicyclo[3.3.1]non-3-yl]ethyl}-N-[2-(4-cyanophenoxy)ethyl]methanesulfonamide;
(xxv) N-[2-(4-cyanophenoxy)ethyl]-N-(2-{7-[4-(difluoromethoxy)-benzyl]-9-oxa-3,7-diazabicyclo[3.3.1]non-3-yl}ethyl)-methanesulfonamide;
(xxvi) N-[2-(4-cyanophenoxy)ethyl]-N-(2-{7-[4-(methylsulfonyl)benzyl]-9-oxa-3,7-diazabicyclo[3.3.1]non-3-yl}ethyl)methanesulfonamide;
(xxvii) N-[2-(4-cyanophenoxy)ethyl]-N-{2-[7-(2-fluorobenzyl)-9-oxa-3,7-diazabicyclo[3.3.1]non-3-yl]ethyl}methanesulfonamide;
(xxviii) N-[2-(4-cyanophenoxy)ethyl]-N-12-[7-(2,4-difluorobenzyl)-9-oxa-3,7-diazabicyclo[3.3.1]non-3-yl]ethyl}methanesulfonamide;
(xxix) N-[2-(4-cyanophenoxy)ethyl]-N-{2-[7-(2,5-dichlorobenzyl)-9-oxa-3,7-diazabicyclo[3.3.1]non-3-yl]ethyl}methanesulfonamide;
(xxx) N-[2-(4-cyanophenoxy)ethyl]-N-(2-{7-[3-(trifluoromethyl)benzyl]-9-oxa-3,7-diazabicyclo[3.3.1]non-3-yl}ethyl)methanesulfonamide;
(xxxi) N-{2-[7-(4-cyanobenzyl)-9-oxa-3,7-diazabicyclo[3.3.1]non-3-yl]ethyl}-N-[2-(4-cyanophenoxy)ethyl]methanesulfonamide;
(xxxii) N-[2-(4-cyanophenoxy)ethyl]-N-(2-{7-[(2,6-dichloropyridin-4-yl)methyl]-9-oxa-3,7-diazabicyclo[3.3.1]non-3-yl}ethyl)-methanesulfonamide;
(xxxiii) N-[2-(4-cyanophenoxy)ethyl]-N-{2-[7-(pyridin-4-ylmethyl)-9-oxa-3,7-diazabicyclo[3.3.1]non-3-yl]ethyl}methanesulfonamide;

(xxxiv) N-[2-(4-cyanophenoxy)ethyl]-N-(2-{7-[(3,5-dimethylisoxazol-4-yl)methyl]-9-oxa-3,7-diazabicyclo[3.3.1]non-3-yl}ethyl)-methanesulfonamide;

(xxxv) N-[2-(4-cyanophenoxy)ethyl]-N-(2-{7-[(2,4-dimethyl-1,3-thiazol-5-yl)methyl]-9-oxa-3,7-diazabicyclo[3.3.1]non-3-yl}ethyl)methane-sulfonamide;

(xxxvi) N-[2-(4-cyanophenoxy)ethyl]-N-(2-{7-[(1-methyl-1H-imidazol-2-yl)methyl]-9-oxa-3,7-diazabicyclo[3.3.1]non-3-yl}ethyl)-methanesulfonamide;

(xxxvii) N-[2-(4-cyanophenoxy)ethyl]-N-{2-[7-(3-phenylpropyl)-9-oxa-3,7-diazabicyclo[3.3.1]non-3-yl]ethyl}methanesulfonamide;

(xxxviii) N-[2-(4-cyanophenoxy)ethyl]-N-(2-{7-[3-(4-cyanophenyl)propyl]-9-oxa-3,7-diazabicyclo[3.3.1]non-3-yl}ethyl)methanesulfonamide;

(xxxix) N-[2-(4-cyanophenoxy)ethyl]-N-(2-{7-[3-(3-methoxyphenyl)-propyl]-9-oxa-3,7-diazabicyclo[3.3.1]non-3-yl}ethyl)methane-sulfonamide;

(xl) N-[2-(4-cyanophenoxy)ethyl]-N-{2-[7-(2,6-dimethylbenzyl)-9-oxa-3,7-diazabicyclo[3.3.1]non-3-yl]ethyl}methanesulfonamide;

(xli); N-{2-[7-(4-tert-butylbenzyl)-9-oxa-3,7-diazabicyclo[3.3.1]non-3-yl]ethyl}-N-[2-(4-cyanophenoxy)ethyl]methanesulfonamide;

(xlii) N-[2-(7-benzyl-9-oxa-3,7-diazabicyclo[3.3.1]non-3-yl)ethyl]-N-[2-(4-cyanophenoxy)ethyl]-N',N'-dimethylurea;

(xliii) N-{2-[7-(4-cyanobenzyl)-9-oxa-3,7-diazabicyclo[3.3.1]non-3-yl]ethyl}-N-[2-(4-cyanophenoxy)ethyl]-N',N'-dimethylurea;

(xliv) N-[2-(4-cyanophenoxy)ethyl]-N-(2-{7-[2-fluoro-4-(trifluoro-methyl)benzyl]-9-oxa-3,7-diazabicyclo[3.3.1]non-3-yl}ethyl)-N',N'-dimethylurea;

(xlv) N-[2-(4-cyanophenoxy)ethyl]-N-{2-[7-(4-fluorobenzyl)-9-oxa-3,7-diazabicyclo[3.3.1]non-3-yl]ethyl}-N',N'-dimethylurea;

(xlvi) N-[2-(4-cyanophenoxy)ethyl]-N-(2-{7-[4-(difluoromethoxy)-benzyl]-9-oxa-3,7-diazabicyclo[3.3.1]non-3-yl}ethyl)-N',N'-dimethylurea;

(xlvii) N-[2-(4-cyanophenoxy)ethyl]-N',N'-dimethyl-N-{2-[7-(2-phenyl-ethyl)-9-oxa-3,7-diazabicyclo[3.3.1]non-3-yl]ethyl}urea;

(xlviii) N-[2-(4-cyanophenoxy)ethyl]-N-(2-{7-[2-(4-cyanophenyl)ethyl]-9-oxa-3,7-diazabicyclo[3.3.1]non-3-yl}ethyl)-N',N'-dimethylurea;

(xlix) N-[2-(4-cyanophenoxy)ethyl]-N-(2-{7-[2-(3-fluorophenyl)ethyl]-9-oxa-3,7-diazabicyclo[3.3.1]non-3-yl}ethyl)-N',N'-dimethylurea;

(l) N-[2-(4-cyanophenoxy)ethyl]-N',N'-dimethyl-N-2-[7-(3-phenyl-propyl)-9-oxa-3,7-diazabicyclo[3.3.1]non-3-yl]ethyl}urea;

(li) N-[2-(4-cyanophenoxy)ethyl]-N-{2-[7-(2-phenylethyl)-9-oxa-3,7-diazabicyclo[3.3.1]non-3-yl]ethyl}methanesulfonamide;

(lii) N-[2-(4-cyanophenoxy)ethyl]-N-(2-{7-[2-(4-cyanophenyl)ethyl]-9-oxa-3,7-diazabicyclo[3.3.1]non-3-yl}ethyl)methanesulfonamide;

(liii) N-[2-(4-cyanophenoxy)ethyl]-N-(2-{7-[2-(4-fluorophenyl)ethyl]-9-oxa-3,7-diazabicyclo[3.3.1]non-3-yl}ethyl)methanesulfonamide;

(liv) N-benzyl-N-(2-{7-[2-(4-cyanophenoxy)ethyl]-9-oxa-3,7-diazabicyclo[3.3.1]non-3-yl}ethyl)methanesulfonamide;

(lv) N-(2-{7-[2-(4-cyanophenoxy)ethyl]-9-oxa-3,7-diazabicyclo-[3.3.1]non-3-yl}ethyl)-N-(2-phenylethyl)methanesulfonamide;

(lvi) N-(2-{7-[3-(4-cyanophenoxy)propyl]-9-oxa-3,7-diazabicyclo-[3.3.1]non-3-yl}ethyl)-N-(2-phenylethyl)methanesulfonamide;

(lvii) N-(2-{7-[2-(4-cyanophenoxy)ethyl]-9-oxa-3,7-diazabicyclo-[3.3.1]non-3-yl}ethyl)-N-(2-phenoxyethyl)methanesulfonamide;

(lviii) N-{2-[7-(4-cyanobenzyl)-9-oxa-3,7-diazabicyclo[3.3.1]non-3-yl]ethyl}-N-(2-phenoxyethyl)methanesulfonamide;

(lix) N-{2-[7-(4-cyanobenzyl)-9-oxa-3,7-diazabicyclo[3.3.1]non-3-yl]ethyl}-N-(2-phenylethyl)methanesulfonamide;

(lx) N-(2-{7-[3-(4-cyanophenoxy)propyl]-9-oxa-3,7-diazabicyclo-[3.3.1]non-3-yl}ethyl)-N-(2-phenoxyethyl)methanesulfonamide;

(lxi) N-benzyl-N-{2-[7-(4-fluorobenzyl)-9-oxa-3,7-diazabicyclo-[3.3.1]non-3-yl]ethyl}methanesulfonamide;

(lxii) N-benzyl-N-{2-[7-(4-chlorobenzyl)-9-oxa-3,7-diazabicyclo-[3.3.1]non-3-yl]ethyl}methanesulfonamide;

(lxiii) N-(2-cyanobenzyl)-N-{2-[7-(4-cyanobenzyl)-9-oxa-3,7-diazabicyclo[3.3.1]non-3-yl]ethyl}methanesulfonamide;

(lxiv) N-{2-[7-(4-cyanobenzyl)-9-oxa-3,7-diazabicyclo[3.3.1]non-3-yl]ethyl}-N-(4-fluorobenzyl)methanesulfonamide;

(lxv) N-{2-[7-(4-cyanobenzyl)-9-oxa-3,7-diazabicyclo[3.3.1]non-3-yl]ethyl}-N-(3-fluorobenzyl)methanesulfonamide;

(lxvi) N-{2-[7-(4-cyanobenzyl)-9-oxa-3,7-diazabicyclo[3.3.1]non-3-yl]ethyl}-N-[4-(difluoromethoxy)benzyl]methanesulfonamide;

(lxvii) N-(4-chlorobenzyl)-N-{2-[7-(4-cyanobenzyl)-9-oxa-3,7-diazabicyclo[3.3.1]non-3-yl]ethyl}methanesulfonamide;

(lxviii) N-benzyl-N-{2-[7-(4-cyanobenzyl)-9-oxa-3,7-diazabicyclo-[3.3.1]non-3-yl]ethyl}ethanesulfonamide;

(lxix) N-benzyl-N-{2-[7-(4-cyanobenzyl)-9-oxa-3,7-diazabicyclo-[3.3.1]non-3-yl]ethyl}-N'-methylurea;

(lxx) N-benzyl-N-(2-{7-[2-(4-cyanophenyl)ethyl]-9-oxa-3,7-diazabicyclo[3.3.1]non-3-yl}ethyl)methanesulfonamide;

(lxxi) N-benzyl-N-(2-{7-[2-(2,4-dicyanophenoxy)ethyl]-9-oxa-3,7-diaza-bicyclo[3.3.1]non-3-yl}ethyl)methanesulfonamide;

(lxxii) N-benzyl-N-(2-{7-[3-(4-cyanophenoxy)propyl]-9-oxa-3,7-diazabicyclo[3.3.1]non-3-yl}ethyl)methane-sulfonamide;

(lxxiii) N-benzyl-N-{2-[7-(4-cyanobenzyl)-9-oxa-3,7-diazabicyclo-[3.3.1]non-3-yl]ethyl}-1,1,1-trifluoromethanesulfonamide;

(lxxiv) N-benzyl-N-{2-[7-(4-cyanobenzyl)-9-oxa-3,7-diazabicyclo-[3.3.1]non-3-yl]ethyl}urea; and (lxxv) N-{2-[7-(4-cyanobenzyl)-9-oxa-3,7-diazabicyclo[3.3.1]non-3-yl]ethyl}-N-(4-fluorobenzyl)urea;

or a pharmaceutically acceptable derivative thereof.

Example 17

Title compounds of the above Examples were tested in Test A above and were found to exhibit $D_{10}$ values of more than 5.5.

Example 18

Title compounds of the above Examples were tested in Test B above and were found to exhibit $pIC_{50}$ values of greater than 4.5. Indeed the compounds of Examples 2, 3 and 9 (xlvi) were found to have $pIC_{50}$ values of 5.55, 5.8 and 5.38, respectively.

Abbreviations
Ac=acetyl
API=atmospheric pressure ionisation (in relation to MS)
aq.=aqueous
br=broad (in relation to NMR)
Bt=benzotriazole
t-BuOH=tert-butanol
CI=chemical ionisation (in relation to MS)
mCPBA=meta-chloroperoxybenzoic acid
d=doublet (in relation to NMR)
DBU=diazabicyclo[5.4.0]undec-7-ene
DCM=dichloromethane
dd=doublet of doublets (in relation to NMR)
DMAP=4-dimethylaminopyridine
DMF=N,N-dimethylformamide
DMSO=dimethylsulfoxide
EDC=1-[3-(dimethylamino)propyl]-3-ethylcarbodiimide
Et=ethyl
EtOAc=ethyl acetate
eq.=equivalents
ES=electrospray (in relation to MS)
FAB=fast atom bombardment (in relation to MS)
FBS=foetal bovine serum
h=hour(s)
HCl=hydrochloric acid
HEPES=4-(2-hydroxyethyl)-1-piperazineethanesulfonic acid
HPLC=high performance liquid chromatography
IMS=industrial methylated spirits
IPA=iso-propyl alcohol (propan-2-ol)
m=multiplet (in relation to NMR)
Me=methyl
MeCN=acetonitrile
MeOH=methanol
min.=minute(s)
m.p.=melting point
MS=mass spectroscopy
NADPH=nicotinamide adenine dinucleotide phosphate, reduced form
OAc=acetate
Pd/C=palladium on carbon
q=quartet (in relation to NMR)
rt=room temperature
s=singlet (in relation to NMR)
t=triplet (in relation to NMR)
TEA=triethylamine
THF=tetrahydrofuran
tlc=thin layer chromatography
Prefixes n-, s-, i-, t- and tert—have their usual meanings: normal, secondary, iso, and tertiary.

The invention claimed is:
1. A compound of formula I,

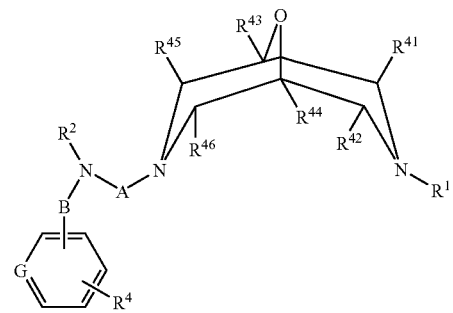

wherein
$R^1$ represents $C_{1-12}$ alkyl (which alkyl group is optionally substituted by one or more groups selected from halo, cyano, nitro, aryl, $Het^1$, —C(O)$R^{5a}$, —O$R^{5b}$, —N($R^6$)$R^{5c}$, —C(O)X$R^7$, —C(O)N($R^{8a}$)$R^{5d}$, —OC(O)N($R^{8b}$)$R^{5e}$, —S(O)$_2R^{9a}$, —S(O)$_2$N($R^{9b}$)$R^{9c}$ and —N($R^{9b}$)S(O)$_2R^{9d}$) or $R^1$ represents —C(O)X$R^7$, —C(O)N($R^{8a}$)$R^{5d}$ or —S(O)$_2R^{9a}$;

$R^{5a}$ to $R^{5e}$ independently represent, at each occurrence when used herein, H, $C_{1-6}$ alkyl (which latter group is optionally substituted by one or more substituents selected from —OH, halo, cyano, nitro, aryl, aryloxy, $Het^2$, —S(O)$_2$N($R^{9b}$)$R^{9c}$ and —N($R^{9b}$)S(O)$_2R^{9d}$), aryl or $Het^3$, or $R^{5d}$ or $R^{5e}$, together with, respectively, $R^{8a}$ or $R^{8b}$, may represent $C_{3-6}$ alkylene (which alkylene group is optionally interrupted by an O atom and/or is optionally substituted by one or more $C_{1-3}$ alkyl groups);

$R^6$ represents H, $C_{1-6}$ alkyl (optionally substituted by one or more substituents selected from —OH, halo, cyano, nitro, aryl, —S(O)$_2$N($R^{9b}$)$R^{9c}$ and —N($R^{9b}$)S(O)$_2R^{9d}$), aryl, —C(O)$R^{10a}$, —C(O)O$R^{10b}$, —C(O)N($R^{10c}$)$R^{10d}$ or —S(O)$_2R^{10e}$;

$R^{10a}$ to $R^{10e}$ independently represent $C_{1-6}$ alkyl (optionally substituted by one or more substituents selected from —OH, halo, cyano, nitro and aryl), aryl, or $R^{10a}$, $R^{10c}$ or $R^{10d}$ represents H;

$R^7$ represents, at each occurrence when used herein, $C_{1-12}$ alkyl (optionally substituted by one or more substituents selected from —OH, halo, cyano, nitro, aryl, $C_{1-6}$ alkoxy, $Het^4$, —S(O)$_2$N($R^{9b}$)$R^{9c}$ and —N($R^{9b}$)S(O)$_2R^{9d}$);

$R^{8a}$ and $R^{8b}$ independently represent H, $C_{1-12}$ alkyl, $C_{1-6}$ alkoxy (which latter two groups are optionally substituted by one or more substituents selected from —OH, halo, cyano, nitro, $C_{1-4}$ alkyl, $C_{1-4}$ alkoxy, —S(O)$_2$N($R^{9b}$)$R^{9c}$ and —N($R^{9b}$)S(O)$_2R^{9d}$, -D-aryl, -D-aryloxy, -D-$Het^5$, -D-N(H)C(O)$R^{11a}$, -D-S(O)$_2R^{12a}$, -D-C(O)$R^{11b}$, -D-C(O)O$R^{12b}$, -D-C(O)N($R^{11c}$)$R^{11d}$, or $R^{8a}$ or $R^{8b}$, together with, respectively, $R^{5d}$ or $R^{5c}$, may represent $C_{3-6}$ alkylene (which alkylene group is optionally interrupted by an O atom and/or is optionally substituted by one or more $C_{1-3}$ alkyl groups);

$R^{11a}$ to $R^{11d}$ independently represent H, $C_{1-6}$ alkyl (optionally substituted by one or more substituents selected from —OH, halo, cyano, nitro and aryl), aryl, or $R^{11c}$ and $R^{11d}$ together represent $C_{3-6}$ alkylene;

$R^{12a}$ and $R^{12b}$ independently represent $C_{1-6}$ alkyl (optionally substituted by one or more substituents selected from —OH, halo, cyano, nitro and aryl) or aryl;

D represents, at each occurrence when used herein, a direct bond or $C_{1-6}$ alkylene;

X represents O or S;

$R^{9a}$ represents, at each occurrence when used herein, $C_{1-6}$ alkyl (optionally substituted by one or more substituents selected from —OH, halo, cyano, nitro, aryl, —S(O)$_2$N(R$^{9b}$)R$^{9c}$ and —N(R$^{9b}$)S(O)$_2$R$^{9d}$) or aryl;

$R^{9b}$ represents, at each occurrence when used herein, H or $C_{1-6}$ alkyl;

$R^{9c}$ and $R^{9d}$ independently represent, at each occurrence when used herein, $C_{1-6}$ alkyl (optionally substituted by one or more substituents selected from —OH, halo, cyano, nitro, aryl and Het$^6$), aryl or Het$^7$, or $R^{9c}$ represents H;

$R^2$ represents —S(O)$_2$R$^{3a}$, —C(O)OR$^{3b}$, —C(O)R$^{3c}$, —C(O)N(R$^{3d}$)(R$^{3e}$) or —S(O)$_2$N(R$^{3f}$)(R$^{3g}$);

$R^{3a}$ to $R^{3g}$ independently represent $C_{1-6}$ alkyl (optionally substituted by one or more substituents selected from halo, -E-aryl, -E-Het$^8$, —C(O)R$^{16a}$, —C(O)OR$^{16b}$ and —C(O)N(R$^{16c}$)R$^{16d}$), aryl or Het$^9$, or $R^{3c}$ and $R^{3d}$ to $R^{3g}$ independently represent H;

$R^{16a}$ to $R^{16d}$ independently represent, at each occurrence when used herein, H, $C_{1-6}$ alkyl (optionally substituted by one or more substituents selected from halo, aryl and Het$^{10}$), aryl, Het$^{11}$, or $R^{16c}$ and $R^{16d}$ together represent $C_{3-6}$ alkylene, optionally interrupted by an O atom;

E represents, at each occurrence when used herein, a direct bond or $C_{1-4}$ alkylene;

Het$^1$ to Het$^{11}$ independently represent five- to twelve-membered heterocyclic groups containing one or more heteroatoms selected from oxygen, nitrogen and/or sulfur, which groups are optionally substituted by one or more substituents selected from —OH, oxo, halo, cyano, nitro, $C_{1-6}$ alkyl, $C_{1-6}$ alkoxy, aryl, aryloxy, —N(R$^{17a}$)R$^{17b}$, —C(O)R$^{17c}$, —C(O)OR$^{17d}$, —C(O)N(R$^{17e}$)R$^{17f}$, —N(R$^{17g}$)C(O)R$^{17h}$, —S(O)$_2$N(R$^{17i}$)R$^{17j}$ and —N(R$^{17k}$)S(O)$_2$R$^{17l}$;

$R^{17a}$ to $R^{17l}$ independently represent $C_{1-6}$ alkyl, aryl or $R^{17a}$ to $R^{17k}$ independently represent H;

A represents $C_{2-6}$ alkylene optionally interrupted by —S(O)$_2$N(R$^{18a}$)— or —N(R$^{18b}$)S(O)$_2$— and/or optionally substituted by one or more substituents selected from —OH, halo and amino;

B represents -Z$^1$-{[C(O)]$_a$C(H)(R$^{19a}$)}$_b$-, -Z$^2$[C(O)]$_c$N(R$^{19b}$)—, -Z$^2$-S(O)$_n$—, -Z$^2$-N(R$^{18c}$)S(O)$_2$—, -Z$^2$-S(O)$_2$N(R$^{18d}$)— or -Z$^2$-O— (in which six groups Z$^1$ or Z$^2$ is attached to the nitrogen atom bearing R$^2$);

Z$^1$ represents a direct bond or $C_{1-4}$ alkylene, optionally interrupted by —N(R$^{18e}$)S(O)$_2$— or —S(O)$_2$N(R$^{18f}$)—;

Z$^2$ represents, at each occurrence when used herein, $C_{2-4}$ alkylene, optionally interrupted by —N(R$^{18g}$)S(O)$_2$— or —S(O)$_2$N(R$^{18h}$)—;

a, b and c independently represent 0 or 1;

n represents 0, 1 or 2;

$R^{18a}$ to $R^{18h}$ independently represent H or $C_{1-6}$ alkyl;

$R^{19a}$ represents H or, together with a single $R^4$ substituent at a position on the phenyl or pyridyl group that is ortho- to the position at which the group B is attached, $R^{19a}$ represents $C_{2-4}$ alkylene optionally interrupted or terminated by O, S or N(R$^{20}$);

$R^{19b}$ represents H, $C_{1-6}$ alkyl or, together with a single $R^4$ substituent at a position on the phenyl or pyridyl group that is ortho- to the position at which the group B is attached, $R^{19b}$ represents $C_{2-4}$ alkylene;

$R^{20}$ represents H or $C_{1-6}$ alkyl;

G represents CH or N;

$R^4$ represents one or more optional substituents selected from —OH, cyano, halo, nitro, $C_{1-6}$ alkyl (optionally terminated by —N(H)C(O)OR$^{21a}$), $C_{1-6}$ alkoxy, —N(R$^{22a}$)R$^{22b}$, —C(O)R$^{22c}$, —C(O)OR$^{22d}$, —C(O)N(R$^{22e}$)R$^{22f}$, —N(R$^{22g}$)C(O)R$^{22h}$, —N(R$^{22i}$)C(O)N(R$^{22j}$)R$^{22k}$, —N(R$^{22m}$)S(O)$_2$R$^{21b}$, —S(O)$_2$N(R$^{22n}$)R$^{22o}$, —S(O)$_2$R$^{21c}$, —OS(O)$_2$R$^{21d}$ and aryl, and an $R^4$ substituent in a position on the phenyl or pyridyl group that is ortho- to the position at which the group B is attached may (i) together with $R^{19a}$, represent $C_{2-4}$ alkylene optionally interrupted or terminated by O, S or N(R$^{20}$), or (ii) together with $R^{19b}$, represent $C_{2-4}$ alkylene;

$R^{21a}$ to $R^{21d}$ independently represent $C_{1-6}$ alkyl;

$R^{22a}$ and $R^{22b}$ independently represent H, $C_{1-6}$ alkyl or together represent $C_{3-6}$ alkylene, resulting in a four- to seven-membered nitrogen-containing ring;

$R^{22c}$ to $R^{22o}$ independently represent H or $C_{1-6}$ alkyl; and $R^{41}$ to $R^{46}$ independently represent H or $C_{1-3}$ alkyl;

wherein each aryl and aryloxy group, unless otherwise specified, is optionally substituted;

or a pharmaceutically acceptable derivative thereof.

2. A compound as claimed in claim 1, wherein optional substituents on aryl and aryloxy groups are one or more substituents selected from —OH, halo, cyano, nitro, $C_{1-6}$ alkyl, $C_{1-6}$ alkoxy, —N(R$^{22a}$)R$^{22b}$, —C(O)R$^{22c}$, —C(O)OR$^{22d}$, —C(O)N(R$^{22e}$)R$^{22f}$, —N(R$^{22g}$)C(O)R$^{22h}$, —N(R$^{22m}$)S(O)$_2$R$^{21b}$, —S(O)$_2$N(R$^{22n}$)R$^{22o}$, —S(O)$_2$R$^{21c}$, and —OS(O)$_2$R$^{21d}$ (wherein R$^{21b}$ to R$^{21d}$ and R$^{22a}$ to R$^{22o}$ are as defined in claim 1).

3. A compound as claimed in claim 1, wherein $R^1$ represents $C_{1-8}$ alkyl (which alkyl group is optionally substituted by one or more groups selected from halo, aryl (which latter group is optionally substituted by one or more substituents selected from —OH, halo, cyano, nitro, $C_{1-5}$ alkyl, $C_{1-4}$ alkoxy (which latter two groups are optionally substituted by one or more halo atoms), —C(O)R$^{22c}$ and —S(O)$_2$R$^{21c}$), Het$^1$, —C(O)R$^{5a}$, —OR$^{5b}$, —N(R$^6$)R$^{5c}$, —C(O)N(R$^{8a}$)R$^{5d}$, —OC(O)N(R$^{8b}$)R$^{5e}$, —S(O)$_2$R$^{9a}$, —1S(O)$_2$N(H)R$^{9c}$ and —N(H)S(O)$_2$R$^{9d}$) or $R^1$ represents —C(O)OR$^7$, —C(O)N(R$^{8a}$)R$^{5d}$ or —S(O)$_2$R$^{9a}$.

4. A compound as claimed in claim 1, wherein R$^{5a}$ to R$^{5e}$ independently represent, at each occurrence when used herein, H, $C_{1-6}$ alkyl (which latter group is optionally substituted by one or more substituents selected from cyano, nitro, optionally substituted aryl and optionally substituted aryloxy), aryl (which latter group is optionally substituted by one or more substituents selected from —OH, halo, cyano, nitro, N(R$^{22a}$)R$^{22b}$ (in which latter group R$^{22a}$ and R$^{22b}$ together represent $C_{3-6}$ alkylene), $C_{1-5}$ alkyl and $C_{1-5}$ alkoxy (which latter two groups are optionally substituted by one or more halo atoms)), Het$^3$, or R$^{5d}$, together with R$^{8a}$, represents $C_{4-5}$ alkylene (which alkylene group is optionally interrupted by an O atom).

5. A compound as claimed in claim 1, wherein $R^6$ represents H, $C_{1-6}$ alkyl, optionally substituted aryl —C(O)R$^{10a}$, —C(O)OR$^{10b}$, —C(O)N(R$^{10c}$)R$^{10d}$ or —S(O)$_2$R$^{10e}$.

6. A compound as claimed in claim 1, wherein R$^{10a}$, R$^{10b}$ and R$^{10e}$ independently represent $C_{1-5}$ alkyl (optionally substituted by one or more substituents selected from halo and optionally substituted aryl) or optionally substituted aryl.

7. A compound as claimed in claim 1, wherein R$^{10c}$ and R$^{10d}$ independently represent H or $C_{1-4}$ alkyl.

8. A compound as claimed in claim 1, wherein $R^7$ represents $C_{1-6}$ alkyl (optionally substituted by one or more substituents selected from halo, optionally substituted aryl, $C_{1-4}$ alkoxy and Het$^4$).

9. A compound as claimed in claim 1, wherein $R^{8a}$ and $R^{8b}$ independently represent H, $C_{1-6}$ alkyl (which latter group is optionally substituted by one or more substituents selected from halo, cyano and nitro), -D-(optionally substituted aryl), -D-(optionally substituted aryloxy), -D-Het$^5$, -D-N(H)C(O)R$^{11a}$, -D-C(O)R$^{11b}$, or $R^{8a}$, together with $R^{5d}$ represents $C_{4-5}$ alkylene (which alkylene group is optionally interrupted by an O atom).

10. A compound as claimed in claim 1, wherein $R^{11a}$ and $R^{11d}$ independently represent $C_{1-4}$ alkyl (optionally substituted by one or more substituents selected from halo, cyano, nitro and optionally substituted aryl) or optionally substituted aryl.

11. A compound as claimed in claim 1, wherein D represents, at each occurrence when used herein, a direct bond or $C_{1-4}$ alkylene.

12. A compound as claimed in claim 1, wherein $R^{9a}$ represents, $C_{1-6}$ alkyl (optionally substituted by one or more halo groups) or optionally substituted aryl.

13. A compound as claimed in claim 1, wherein $R^{9c}$ and $R^{9d}$ independently represent, at each occurrence when used herein, $C_{1-5}$ alkyl (optionally substituted by one or more substituents selected from halo, optionally substituted aryl and Het$^6$), optionally substituted aryl or Het$^7$, or $R^{9c}$ represents H.

14. A compound as claimed in claim 1, wherein $R^2$ represents —S(O)$_2$R$^{3a}$, —C(O)OR$^{3b}$, —C(O)R$^{3c}$ or —C(O)N(R$^{3d}$)R$^{3e}$.

15. A compound as claimed in claim 1, wherein $R^{3a}$ to $R^{3e}$ independently represent $C_{1-5}$ alkyl (optionally substituted by one or more substituents selected from halo, optionally substituted aryl and Het$^8$), optionally substituted aryl or Het$^9$, or $R^{3d}$ represents H.

16. A compound as claimed in claim 1, wherein Het$^1$ and Het$^3$ to Het$^9$ independently represent four- to ten-membered heterocyclic groups containing one to four heteroatoms selected from oxygen, nitrogen and/or sulfur, which groups are optionally substituted by one or more substituents selected from —OH, oxo, halo, cyano, $C_{1-4}$ alkyl, $C_{1-4}$ alkoxy, phenyl, —N(H)R$^{17a}$, —C(O)R$^{17c}$, —N(H)C(O)R$^{17h}$ and —N(H)S(O)$_2$R$^{17j}$.

17. A compound as claimed in claim 1, wherein $R^{17a}$, $R^{17c}$, $R^{17h}$ and $R^{17j}$ independently represent $C_{1-4}$ alkyl or optionally substituted aryl or $R^{17a}$, $R^{17c}$ and $R^{17h}$ independently represent H.

18. A compound as claimed in claim 1, wherein A represents $C_{2-4}$ alkylene optionally substituted by one or more substituents selected from —OH and amino.

19. A compound as claimed in claim 1, wherein B represents -Z$^1$-, -Z$^2$-N(H)—, -Z$^2$-C(O)N(R$^{19b}$)—, -Z$^2$-S(O)$_2$—, -Z$^2$-N(H)S(O)$_2$—, -Z$^2$-S(O)$_2$N(H)— or -Z$^2$-O— (in which latter six groups, Z$^2$ is attached to the nitrogen atom bearing $R^2$).

20. A compound as claimed in claim 1, wherein $Z^1$ represents a direct bond or $C_{1-4}$ alkylene.

21. A compound as claimed in claim 1, wherein $Z^2$ represents $C_{2-4}$ alkylene.

22. A compound as claimed in claim 1, wherein $R^{19b}$ represents H, $C_{1-4}$ alkyl, or, together with a single $R^4$ substituent at a position on the phenyl or pyridyl group that is ortho- to the position at which the group B is attached, $R^{19b}$ represents $C_{2-4}$ alkylene.

23. A compound as claimed in claim 1, wherein when G represents N, G is in the ortho- or para-position relative to the point of attachment of B.

24. A compound as claimed in claim 1, wherein when G represents N, $R^4$ is absent or represents a single cyano group.

25. A compound as claimed in claim 1, wherein $R^4$ is absent or represents one or more substituents selected from —OH, cyano, halo, nitro, $C_{1-6}$ alkyl, $C_{1-6}$ alkoxy, —C(O)N(R$^{22e}$)R$^{22f}$, and —N(R$^{22m}$)S(O)$_2$—$C_{1-4}$ alkyl, or an $R^4$ substituent in a position on the phenyl or pyridyl group that is ortho- to the position at which the group B is attached may, together with $R^{19b}$, represent $C_{2-4}$ alkylene.

26. A compound as claimed in claim 1, wherein $R^{21c}$ represents $C_{1-4}$ alkyl and $R^{22c}$, $R^{22e}$, $R^{22f}$ and $R^{22m}$ independently represent H or $C_{1-4}$ alkyl.

27. A compound as claimed in claim 1, wherein $R^{41}$ to $R^{46}$ independently represent H.

28. A compound as claimed in claim 1, wherein optional substituents on aryl and aryloxy groups are, unless otherwise stated, one or more substituents selected from halo, cyano, nitro, $C_{1-4}$ alkyl and $C_{1-4}$ alkoxy (which latter two groups are optionally substituted by one or more halo atoms), —N(H)S(O)$_2$R$^{21b}$ and —S(O)$_2$N(H)R$^{22o}$.

29. A compound as claimed in claim 1, wherein alkyl groups and alkoxy groups may be, unless otherwise specified:
(i) straight- or branched-chain or cyclic or part cyclic/acyclic;
(ii) saturated or unsaturated;
(iii) interrupted by one or more oxygen atoms; and/or (iv) substituted by one or more fluoro or chloro atoms.

30. A compound as claimed in claim 1 which is:
(i) tert-butyl [2-(7-{2-[[2-(4-cyanophenoxy)ethyl](methylsulfonyl)amino]ethyl}-9-oxa-3,7-diazabicyclo[3.3.1]non-3-yl)ethyl]carbamate;
(ii) tert-butyl {2-[7-(2-{(aminocarbonyl)[2-(4-cyanophenoxy)ethyl]amino}ethyl)-9-oxa-3,7-diazabicyclo[3.3.1]non-3-yl]ethyl}carbamate;
(iii) N-[2-(4-cyanophenoxy)ethyl]-N-(2-{7-[2-(4-methoxyphenyl)-2-oxoethyl]-9-oxa-3,7-di-azabicyclo[3.3.1]non-3-yl}ethyl)methanesulfonamide;
(iv) N-[2-(4-cyanophenoxy)ethyl]-N-(2-{7-[2-(4-methoxyphenyl)-2-oxoethyl]-9-oxa-3,7-di-azabicyclo[3.3.1]non-3-yl}ethyl)urea;
(v) N-[2-(7-benzyl-9-oxa-3,7-diazabicyclo[3.3.1]non-3-yl)ethyl]-N-[2-(4-cyanophenoxy)ethyl]methanesulfonamide;
(vi) N-[2-(7-benzyl-9-oxa-3,7-diazabicyclo[3.3.1]non-3-yl)ethyl]-N-[2-(4-cyanophenoxy)ethyl]urea;
(vii) 2-[7-(2-{(aminocarbonyl)[2-(4-cyanophenoxy)ethyl]amino}ethyl)-9-oxa-3,7-diazabicyclo[3.3.1]non-3-yl]-N-(tert-butyl)acetamide;
(viii) 2-[7-(2-{(aminocarbonyl)[2-(4-cyanophenoxy)ethyl]amino}ethyl)-9-oxa-3,7-diazabicyclo[3.3.1]non-3-yl]-N-benzylacetamide;
(ix) 2-[7-(2-{(aminocarbonyl)[2-(4-cyanophenoxy)ethyl]amino}ethyl)-9-oxa-3,7-diazabicyclo[3.3.1]non-3-yl]-N-(1-methyl-1-phenylethyl)acetamide;
(x) N-(tert-butyl)-2-(7-{2-[[2-(4-cyanophenoxy)ethyl](methylsulfonyl)amino]ethyl}-9-oxa-3,7-diazabicyclo[3.3.1]non-3-yl)acetamide;
(xi) N-benzyl-2-(7-{2-[[2-(4-cyanophenoxy)ethyl](methylsulfonyl)amino]ethyl}-9-oxa-3,7-diazabicyclo[3.3.1]non-3-yl)acetamide;
(xii) 2-(7-{2-[[2-(4-cyanophenoxy)ethyl](methylsulfonyl)amino]ethyl}-9-oxa-3,7-diazabicyclo[3.3.1]non-3-yl)-N-(1-methyl-1-phenylethyl)acetamide;

(xiii) tert-butyl [2-(7-{2-[[3-(4-cyanophenyl)propyl](methylsulfonyl)amino]ethyl}-9-oxa-3,7-diazabicyclo[3.3.1]non-3-yl)ethyl]carbamate;

(xiv) N-(tert-butyl)-2-(7-{2-[[3-(4-cyanophenyl)propyl](methylsulfonyl)amino]ethyl}-9-oxa-3,7-diazabicyclo[3.3.1]non-3-yl)acetamide;

(xv) N-[2-(7-benzyl-9-oxa-3,7-diazabicyclo[3.3.1]non-3-yl)ethyl]-N-[3-(4-cyanophenyl)propyl]methanesulfonamide;

(xvi) N-[2-(4-cyanophenoxy)ethyl]-N-(2-{7-[2-(2,6-dimethylphenoxy)ethyl]-9-oxa-3,7-diazabicyclo[3.3.1]non-3-yl}ethyl)urea;

(xvii) N-[2-(4-cyanophenoxy)ethyl]-N-(2-{7-[2-(4-cyanophenyl)ethyl]-9-oxa-3,7-diazabicyclo[3.3.1]non-3-yl}ethyl)urea;

(xviii) N-[2-(4-cyanophenoxy)ethyl]-N-(2-{7-[2-(4-methoxyphenyl)ethyl]-9-oxa-3,7-diazabicyclo[3.3.1]non-3-yl}ethyl)urea;

(xix) N-(2-{7-[2-(4-acetylphenyl)ethyl]-9-oxa-3,7-diazabicyclo[3.3.1]non-3-yl}ethyl)-N-[2-(4-cyanophenoxy)ethyl]urea;

(xx) N-[2-(4-cyanophenoxy)ethyl]-N-{2-[7-(2-phenylethyl)-9-oxa-3,7-diazabicyclo-[3.3.1]non-3-yl]ethyl}urea;

(xxi) N-[2-(4-cyanophenoxy)ethyl]-N-(2-{7-[2-(3-fluorophenyl)ethyl]-9-oxa-3,7-diazabicyclo[3.3.1]non-3-yl}ethyl)urea;

(xxii) N-(2-{7-[(2-chloropyridin-3-yl)methyl]-9-oxa-3,7-diazabicyclo[3.3.1]non-3yl}ethyl)-N-[2-(4-cyanophenoxy)ethyl]methanesulfonamide;

(xxiii) N-[2-(4-cyanophenoxy)ethyl]-N-(2-{7-[(6-methoxypyridin-3-yl)methyl]-9-oxa-3,7-diazabicyclo[3.3.1]non-3-yl}ethyl)methanesulfonamide;

(xxiv) N-[2-(4-cyanophenoxy)ethyl]-N-(2-{7-[(4,5-dimethyl-2-furyl)methyl]-9-oxa-3,7-diazabicyclo[3.3.1]non-3-yl}ethyl)methanesulfonamide;

(xxv) N-[2-(4-cyanophenoxy)ethyl]-N-{2-[7-(4-fluorobenzyl)-9-oxa-3,7-diazabicyclo-[3.3.1]non-3-yl]ethyl}methanesulfonamide;

(xxvi) N-[2-(4-cyanophenoxy)ethyl]-N-(2-{7-[4-(trifluoromethyl)benzyl]-9-oxa-3,7-diazabicyclo[3.3.1]non-3-yl}ethyl)methanesulfonamide;

(xxvii) N-{2-[7-(4-chlorobenzyl)-9-oxa-3,7-diazabicyclo[3.3.1]non-3-yl]ethyl}-N-[2-(4-cyanophenoxy)ethyl]methanesulfonamide;

(xxviii) N-[2-(4-cyanophenoxy)ethyl]-N-(2-{7-[4-(difluoromethoxy)benzyl]-9-oxa-3,7-diazabicyclo[3.3.1]non-3-yl}ethyl)methanesulfonamide;

(xxix) N-[2-(4-cyanophenoxy)ethyl]-N-(2-{7-[4-(methylsulfonyl)benzyl]-9-oxa-3,7-diazabicyclo[3.3.1]non-3-yl}ethyl)methanesulfonamide;

(xxx) N-[2-(4-cyanophenoxy)ethyl]-N-{2-[7-(2-fluorobenzyl)-9-oxa-3,7-diazabicyclo[3.3.1]non-3-yl]ethyl}methanesulfonamide;

(xxxi) N-[2-(4-cyanophenoxy)ethyl]-N-{2-[7-(2,4-difluorobenzyl)-9-oxa-3,7-diazabicyclo-[3.3.1]non-3-yl]ethyl}methanesulfonamide;

(xxxii) N-[2-(4-cyanophenoxy)ethyl]-N-{2-[7-(2,5-dichlorobenzyl)-9-oxa-3,7-diazabicyclo-[3.3.1]non-3-yl]ethyl}methanesulfonamide;

(xxxiii) N-[2-(4-cyanophenoxy)ethyl]-N-(2-{7-[3-(trifluoromethyl)benzyl]-9-oxa-3,7-diazabicyclo[3.3.1]non-3-yl}ethyl)methanesulfonamide;

(xxxiv) N-{2-[7-(4-cyanobenzyl)-9-oxa-3,7-diazabicyclo[3.3.1]non-3-yl]ethyl}-N-[2-(4-cyanophenoxy)ethyl]methanesulfonamide;

(xxxv) N-{2-[7-(2-cyanobenzyl)-9-oxa-3,7-diazabicyclo[3.3.1]non-3-yl]ethyl}-N-[2-(4-cyanophenoxy)ethyl]methanesulfonamide;

(xxxvi) N-[2-(4-cyanophenoxy)ethyl]-N-(2-{7-[(2,6-dichloropyridin-4-yl)methyl]-9-oxa-3,7-diazabicyclo[3.3.1]non-3-yl}ethyl)methanesulfonamide;

(xxxvii) N-[2-(4-cyanophenoxy)ethyl]-N-{2-[7-(pyridin-4-ylmethyl)-9-oxa-3,7-diazabicyclo-[3.3.1]non-3-yl]ethyl}methanesulfonamide;

(xxxviii) N-[2-(4-cyanophenoxy)ethyl]-N-{2-[7-(pyridin-3-ylmethyl)-9-oxa-3,7-diazabicyclo-[3.3.1]non-3-yl]ethyl}methanesulfonamide;

(xxxix) N-[2-(4-cyanophenoxy)ethyl]-N-(2-{7-[(3,5-dimethylisoxazol-4-yl)methyl]-9-oxa-3,7-diazabicyclo[3.3.1]non-3-yl}ethyl)methanesulfonamide;

(xl) N-[2-(4-cyanophenoxy)ethyl]-N-(2-{7-[(2,4-dimethyl-1,3-thiazol-5-yl)methyl]-9-oxa-3,7-diazabicyclo[3.3.1]non-3-yl}ethyl)methanesulfonamide;

(xli) N-[2-(4-cyanophenoxy)ethyl]-N-(2-{7-[(1-methyl-1H-imidazol-2-yl)methyl]-9-oxa-3,7-diazabicyclo[3.3.1]non-3-yl}ethyl)methanesulfonamide;

(xlii) N-benzyl-N-{2-[7-(4-cyanobenzyl)-9-oxa-3,7-diazabicyclo[3.3.1]non-3-yl]ethyl}methanesulfonamide;

(xliii) N-[2-(4-cyanophenoxy)ethyl]-N-{2-[7-(3-phenylpropyl)-9-oxa-3,7-diazabicyclo-[3.3.1]non-3-yl]ethyl}methanesulfonamide;

(xliv) N-[2-(4-cyanophenoxy)ethyl]-N-(2-{7-[3-(4-cyanophenyl)propyl]-9-oxa-3,7-diazabicyclo[3.3.1]non-3-yl}ethyl)methanesulfonamide;

(xlv) N-[2-(4-cyanophenoxy)ethyl]-N-(2-{7-[3-(3-methoxyphenyl)propyl]-9-oxa-3,7-diazabicyclo[3.3.1]non-3-yl}ethyl)methanesulfonamide;

(xlvi) N-[2-(4-cyanophenoxy)ethyl]-N-{2-[7-(2,6-dimethylbenzyl)-9-oxa-3,7-diazabicyclo-[3.3.1]non-3-yl]ethyl}methanesulfonamide;

(xlvii) N-{2-[7-(4-tert-butylbenzyl)-9-oxa-3,7-diazabicyclo[3.3.1]non-3-yl]ethyl}-N-[2-(4-cyanophenoxy)ethyl]methanesulfonamide;

(xlviii) N-[2-(7-benzyl-9-oxa-3,7-diazabicyclo[3.3.1]non-3-yl)ethyl]-N-[2-(4-cyanophenoxy)ethyl]-N',N'-dimethylurea;

(xlix) N-{2-[7-(4-cyanobenzyl)-9-oxa-3,7-diazabicyclo[3.3.1]non-3-yl]ethyl}-N-[2-(4-cyanophenoxy)ethyl]-N',N'-dimethylurea;

(l) N-[2-(4-cyanophenoxy)ethyl]-N-(2-{7-[2-fluoro-4-(trifluoromethyl)benzyl]-9-oxa-3,7-diazabicyclo[3.3.1]non-3-yl}ethyl)-N',N'-dimethylurea;

(li) N-[2-(4-cyanophenoxy)ethyl]-N-{2-[7-(4-fluorobenzyl)-9-oxa-3,7-diazabicyclo-[3.3.1]non-3-yl]ethyl}-N',N'-dimethylurea;

(lii) N-[2-(4-cyanophenoxy)ethyl]-N-(2-{7-[4-(difluoromethoxy)benzyl]-9-oxa-3,7-diazabicyclo[3.3.1]non-3-yl}ethyl)-N',N'-dimethylurea;

(liii) N-[2-(4-cyanophenoxy)ethyl]-N',N'-dimethyl-N-{2-[7-(2-phenylethyl)-9-oxa-3,7-diazabicyclo[3.3.1]non-3-yl]ethyl}urea;

(liv) N-[2-(4-cyanophenoxy)ethyl]-N-(2-{7-[2-(4-cyanophenyl)ethyl]-9-oxa-3,7-diazabicyclo[3.3.1]non-3-yl}ethyl)-N',N'-dimethylurea;

(lv) N-[2-(4-cyanophenoxy)ethyl]-N-(2-{7-[2-(3-fluorophenyl)ethyl]-9-oxa-3,7-diazabicyclo[3.3.1]non-3-yl}ethyl)-N',N'-dimethylurea;

(lvi) N-[2-(4-cyanophenoxy)ethyl]-N',N'-dimethyl-N-{2-[7-(3-phenylpropyl)-9-oxa-3,7-diazabicyclo[3.3.1]non-3-yl]ethyl}urea;

(lvii) N-[2-(4-cyanophenoxy)ethyl]-N-{2-[7-(2-phenyl-ethyl)-9-oxa-3,7-diazabicyclo-[3.3.1]non-3-yl]ethyl}methanesulfonamide;

(lviii) N-[2-(4-cyanophenoxy)ethyl]-N-(2-{7-[2-(4-cyanophenyl)ethyl]-9-oxa-3,7-diazabicyclo[3.3.1]non-3-yl}ethyl)methanesulfonamide;

(lix) N-[2-(4-cyanophenoxy)ethyl]-N-(2-{7-[2-(4-fluorophenyl)ethyl]-9-oxa-3,7-diazabicyclo[3.3.1]non-3-yl}ethyl)methanesulfonamide;

(lx) N-benzyl-N-(2-{7-[2-(4-cyanophenoxy)ethyl]-9-oxa-3,7-diazabicyclo[3.3.1]non-3-yl}ethyl)methanesulfonamide;

(lxi) N-(2-{7-[2-(4-cyanophenoxy)ethyl]-9-oxa-3,7-diazabicyclo[3.3.1]non-3-yl}ethyl)-N-(2-phenylethyl)methanesulfonamide;

(lxii) N-(2-{7-[3-(4-cyanophenoxy)propyl]-9-oxa-3,7-diazabicyclo[3.3.1]non-3-yl}ethyl)-N-(2-phenylethyl)methanesulfonamide;

(lxiii) N-(2-{7-[2-(4-cyanophenoxy)ethyl]-9-oxa-3,7-diazabicyclo[3.3.1]non-3-yl}ethyl)-N-(2-phenoxyethyl)methanesulfonamide;

(lxiv) N-{2-[7-(4-cyanobenzyl)-9-oxa-3,7-diazabicyclo[3.3.1]non-3-yl]ethyl}-N-(2-phenoxyethyl)methanesulfonamide;

(lxv) N-{2-[7-(4-cyanobenzyl)-9-oxa-3,7-diazabicyclo[3.3.1]non-3-yl]ethyl}-N-(2-phenylethyl)methanesulfonamide;

(lxvi) N-(2-{7-[3-(4-cyanophenoxy)propyl]-9-oxa-3,7-diazabicyclo[3.3.1]non-3-yl}ethyl)-N-(2-phenoxyethyl)methanesulfonamide;

(lxvii) N-benzyl-N-{2-[7-(4-fluorobenzyl)-9-oxa-3,7-diazabicyclo[3.3.1]non-3-yl]ethyl}methanesulfonamide;

(lxviii) N-benzyl-N-{2-[7-(4-chlorobenzyl)-9-oxa-3,7-diazabicyclo[3.3.1]non-3-yl]ethyl}methanesulfonamide;

(lxix) N-benzyl-N-{2-[7-(4-cyanobenzyl)-9-oxa-3,7-diazabicyclo[3.3.1]non-3-yl]ethyl}benzenesulfonamide;

(lxx) N-(4-cyanobenzyl)-N-{2-[7-(4-cyanobenzyl)-9-oxa-3,7-diazabicyclo[3.3.1]non-3-yl]ethyl}methanesulfonamide;

(lxxi) N-(2-cyanobenzyl)-N-{2-[7-(4-cyanobenzyl)-9-oxa-3,7-diazabicyclo[3.3.1]non-3-yl]ethyl}methanesulfonamide;

(lxxii) N-{2-[7-(4-cyanobenzyl)-9-oxa-3,7-diazabicyclo[3.3.1]non-3-yl]ethyl}-N-(4-fluorobenzyl)methanesulfonamide;

(lxxiii) N-{2-[7-(4-cyanobenzyl)-9-oxa-3,7-diazabicyclo[3.3.1]non-3-yl]ethyl}-N-(3-fluorobenzyl)methanesulfonamide;

(lxxiv) N-{2-[7-(4-cyanobenzyl)-9-oxa-3,7-diazabicyclo[3.3.1]non-3-yl]ethyl}-N-[4-(difluoromethoxy)benzyl]methanesulfonamide;

(lxxv) N-(4-chlorobenzyl)-N-{2-[7-(4-cyanobenzyl)-9-oxa-3,7-diazabicyclo[3.3.1]non-3-yl]ethyl}methanesulfonamide;

(lxxvi) N-benzyl-N-{2-[7-(4-cyanobenzyl)-9-oxa-3,7-diazabicyclo[3.3.1]non-3-yl]ethyl}ethanesulfonamide;

(lxxvii) N-benzyl-N-{2-[7-(4-cyanobenzyl)-9-oxa-3,7-diazabicyclo[3.3.1]non-3-yl]ethyl}-N'-methylurea;

(lxxviii) N-benzyl-N-{2-[7-(4-cyanobenzyl)-9-oxa-3,7-diazabicyclo[3.3.1]non-3-yl]ethyl}-N',N'-dimethylurea;

(lxxix) N-benzyl-N-(2-{7-[2-(4-cyanophenyl)ethyl]-9-oxa-3,7-diazabicyclo[3.3.1]non-3-yl}ethyl)methanesulfonamide;

(lxxx) N-benzyl-N-(2-{7-[2-(2,4-dicyanophenoxy)ethyl]-9-oxa-3,7-diazabicyclo[3.3.1]non-3-yl}ethyl)methanesulfonamide;

(lxxxi) N-benzyl-N-(2-{7-[3-(4-cyanophenoxy)propyl]-9-oxa-3,7-diazabicyclo[3.3.1]non-3-yl}ethyl)methanesulfonamide;

(lxxxii) N-benzyl-N-{2-[7-(4-cyanobenzyl)-9-oxa-3,7-diazabicyclo[3.3.1]non-3-yl]ethyl}-1,1,1-trifluoromethanesulfonamide;

(lxxxiii) N-benzyl-N-{2-[7-(4-cyanobenzyl)-9-oxa-3,7-diazabicyclo[3.3.1]non-3-yl]ethyl}acetamide;

(lxxxiv) N-benzyl-N-{2-[7-(4-cyanobenzyl)-9-oxa-3,7-diazabicyclo[3.3.1]non-3-yl]ethyl}urea;

(lxxxv) N-benzyl-N-{2-[7-(4-cyanobenzyl)-9-oxa-3,7-diazabicyclo[3.3.1]non-3-yl]ethyl}propane-2-sulfonamide; or (lxxxvi) N-{2-[7-(4-cyanobenzyl)-9-oxa-3,7-diazabicyclo[3.3.1]non-3-yl]ethyl}-N-(4-fluorobenzyl)urea;

or a pharmaceutically acceptable derivative thereof.

31. A compound as claimed in claim 30 which is N-benzyl-N-{2-[7-(4-cyanobenzyl)-9-oxa-3,7-diazabicyclo[3.3.1]non-3-yl]ethyl}methane-sulfonamide, or a pharmaceutically acceptable derivative thereof.

32. A pharmaceutical formulation comprising a compound as of claim 1 in admixture with a pharmaceutically-acceptable adjuvant, diluent or carrier.

33. A process for the preparation of a compound of formula I as defined in claim 1, which process comprises:
(a) reaction of a compound of formula II,

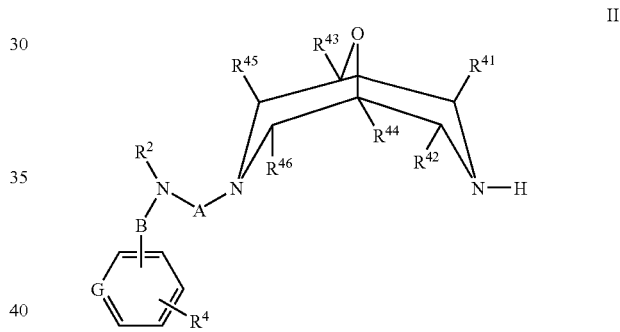

wherein $R^2$, $R^4$, $R^{41}$ to $R^{46}$, A, B and G are as defined in claim 1, with a compound of formula III, $R^1$-$L^1$       III wherein $L^1$ represents a leaving group and X, $R^1$ and $R^7$ are as defined in claim 1;

(b) for compounds of formula I in which $R^1$ represents —C(O)X$R^7$ or —C(O)N($R^{8a}$)$R^{5d}$, reaction of a compound of formula IV,

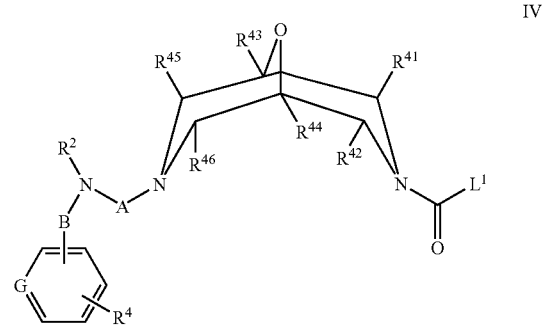

wherein $R^2$, $R^4$, $R^{41}$ to $R^{46}$, A, B, and G are as defined in claim 1, and $L^1$ is as defined above, with a compound of formula V, $$R^{24}\text{---}H \qquad\qquad V$$

wherein R represents $—XR^7$ or $—N(R^{8a})R^{5d}$ and $R^{5d}$, $R^7$, $R^{8a}$ and X are as defined in claim 1;

(c) for compounds in which $R^1$ represents $—C(O)N(H)R^{8a}$, reaction of a compound of formula II, as defined above, with a compound of formula VI, $$R^{8a}\text{---}N{=}C{=}O \qquad\qquad VI$$

wherein $R^{8a}$ is as defined in claim 1;

(d) reaction of a compound of formula VII,

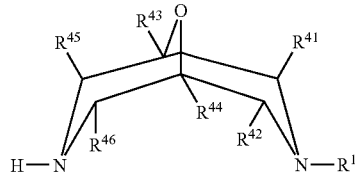

VII wherein $R^1$ and $R^{41}$ to $R^{46}$ are as defined in claim 1, with a compound of formula VIII,

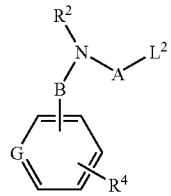

VIII wherein $L^2$ represents a leaving group and $R^2$, $R^4$, A, B and G are as defined in claim 1;

(e) for compounds of formula I in which A represents $C_{3-6}$ alkylene substituted in the 2-position (relative to the oxabispidine N-atom) by —OH or amino, reaction of a compound of formula VII, as defined above, with a compound of formula IX,

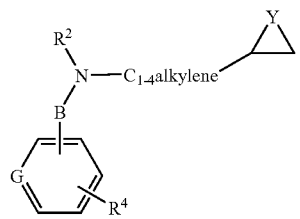

IX or a protected derivative thereof, wherein Y represents O or NH and $R^2$, $R^4$, B and G are as defined in claim 1;

(f) for compounds of formula I in which B represents $-Z^2$-O—, reaction of a compound of formula X,

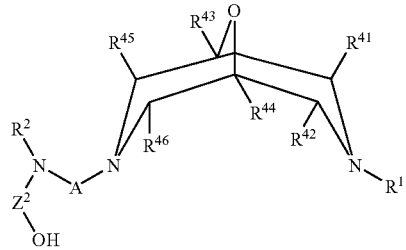

X wherein $R^1$, $R^2$, $R^{41}$ to $R^{46}$, A and $Z^2$ are as defined in claim 1, with a compound of formula XI,

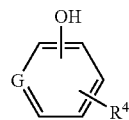

XI wherein $R^4$ and G are as defined in claim 1;

(g) for compounds of formula I in which G represents N and B represents $-Z^2$-O—, reaction of a compound of formula X, as defined above, with a compound of formula XII,

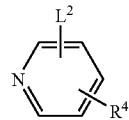

XII wherein $R^4$ is as defined in claim 1, and $L^2$ is as defined above;

(h) for compounds of formula I in which B is as defined in claim 1, except that it does not represent a direct bond, reaction of a compound of formula XIII,

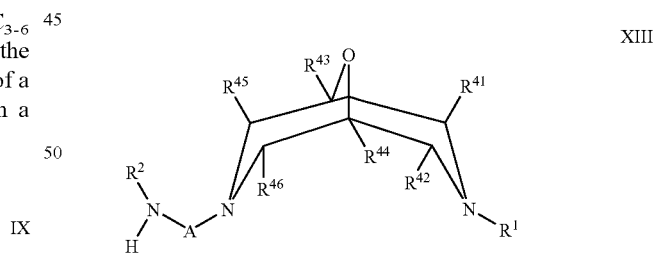

XIII wherein $R^1$, $R^2$, $R^{41}$ to $R^{46}$ and A are as defined in claim 1, with a compound of formula XIV,

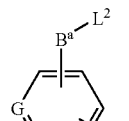

XIV wherein $B^a$ represents B as defined in claim 1, except that it does not represent a direct bond, and $R^4$ and G are as defined in claim 1 and $L^2$ is as defined above;

(i) reaction of a compound of formula XV,

XV wherein $R^1$, $R^4$, $R^{41}$ to $R^{46}$, A, B and G are as defined in claim 1, with a compound of formula XVI, $R^2$-$L^3$      XVI wherein $L^3$ represents a suitable leaving group and $R^2$ is as defined in claim 1;

(j) for compounds of formula I in which $R^2$ represents —C(O)N(H)$R^{3d}$, reaction of a compound of formula XV, as defined above, with a compound of formula XVII

O=C=N—R      XVII wherein R represents a monovalent metal cation or R represents $R^{3d}$ as defined in claim 1, except that it does not represent H;

(k) for compounds of formula I in which $R^1$ represents $C_{1-12}$ alkyl substituted by one or more substituents as defined in claim 1 in respect of $R^1$, which substituent(s) is/include a —N($R^{9b}$)S(O)$_2 R^{9d}$ group, reaction of a compound of formula XVIII,

XVIII wherein $R^{1a}$ represents $C_{1-12}$ alkylene, which group is optionally substituted by one or more substituents as defined in claim 1 in respect of $R^1$, and $R^2$, $R^4$, $R^{9b}$, $R^{41}$ to $R^{46}$, A, B and G are as defined in claim 1, with a compound of formula XIX, $L^2$-S(O)$_2 R^{9d}$      XIX wherein $R^{9d}$ is as defined in claim 1 and $L^2$ is as defined above;

(l) for compounds of formula I in which $R^1$ represents $C_{1-12}$ alkyl substituted by one or more substituents as defined in claim 1 in respect of $R^1$, which substituent(s) is/include a —S(O)$_2$N($R^{9b}$)$R^{9c}$ or —N($R^{9b}$)S(O)$_2 R^{9d}$ group, reaction of a compound of formula II, as defined above, with a compound of formula XIXA or XIXB, $L^1$-$R^{1a}$—SO$_2$—N($R^{9b}$)$R^{9c}$      XIXA $L^1$-$R^{1a}$—N($R^{9b}$)—SO$_2$—$R^{9d}$      XIXB wherein $L^1$ and $R^{1a}$ are as defined above and $R^{9b}$, $R^{9c}$ and $R^{9d}$ are as defined in claim 1;

(m) for compounds of formula I in which R represents —C(O)X$R^7$, —C(O)N($R^{8a}$)$R^{5d}$ or —S(O)$_2 R^{9a}$, reaction of a compound of formula XX,

XX wherein $R^{1a}$ represents —C(O)X$R^7$, —C(O)N($R^{8a}$)$R^{5d}$ or —S(O)$_2 R^{9a}$ and $R^{5d}$, $R^7$, $R^{8a}$, $R^{9a}$ and $R^{41}$ to $R^{46}$ are as defined in claim 1 and $L^2$ is as defined above, with a compound of formula XXI,

XXI wherein $R^2$, $R^4$, A, B and G are as defined in claim 1;

(n) for compounds of formula I which are oxabispidine-nitrogen N-oxide derivatives, oxidation of the corresponding oxabispidine nitrogen of a corresponding compound of formula I, in the presence an oxidising agent;

(o) for compounds of formula I which are $C_{1-4}$ alkyl quaternary ammonium salt derivatives, in which the alkyl group is attached to a oxabispidine nitrogen, reaction, at the oxabispidine nitrogen, of a corresponding compound of formula I with a compound of formula XXII, $R^{25}$-$L^4$      XXII wherein $R^{25}$ represents $C_{1-4}$ alkyl and $L^4$ is a leaving group;

(o) conversion of one $R^4$ substituent to another;

(p) introduction of one or more $R^4$ substituents to the aromatic ring;

(q) for compounds of formula I in wherein $R^1$ represents $C_{1-12}$ alkylene, which group is optionally substituted by one or more substituents as defined above in respect of $R^1$, reaction of a compound of formula II

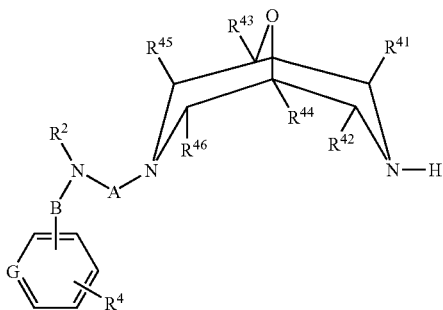

wherein $R^2$, $R^4$, $R^{41}$ to $R^{46}$, A, B and G are as hereinbefore defined, with the appropriate aldehyde, in the presence of a reducing agent and an appropriate solvent from 1,2-dichloroethane, dichloroethane, methanol, ethanol and mixtures thereof;

(r) reaction of a compound with formula VII

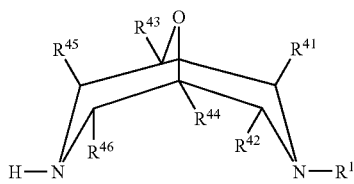

wherein $R^1$ and $R^{41}$ to $R^{46}$ are as hereinbefore defined, with a compound of formula XXIII

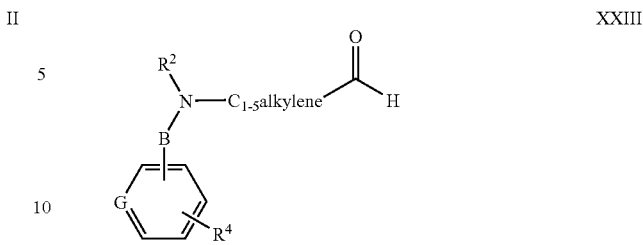

wherein $R^2$, $R^4$, B and G are as hereinbefore defined, in the presence of a reducing agent and an appropriate solvent form 1,2-dichloroethane, dichloroethane, methanol, ethanol and mixtures thereof; or (s) deprotection of a protected derivative of a compound of formula I as defined in claim 1.

34. The process of claim 33 wherein in (q):
 the compound of formula II is reacted with the aldehyde from 15 to 30° C.;
 the reducing agent is sodium cyanoborohydride or sodium triacetoxyborohydride; and
 the solvent is 1,2-dichloroethane, dichloroethane, methanol, ethanol, or any mixture thereof;

in (r):
 the compound of formula VII is reacted with a compound of formula XXIII from 15 to 30° C.;
 the reducing agent is sodium cyanoborohydride or sodium triacetoxyborohydride; and
 the solvent is 1,2-dichloroethane, dichloroethane, methanol, ethanol, or any mixture thereof).

* * * * *